(12) United States Patent
Sethuraman et al.

(10) Patent No.: US 10,889,577 B2
(45) Date of Patent: Jan. 12, 2021

(54) SOLID FORMS OF AN SGC STIMULATOR

(71) Applicant: Cyclerion Therapeutics, Inc., Cambridge, MA (US)

(72) Inventors: Vasu Sethuraman, Waltham, MA (US); Ahmad Hashash, Southborough, MA (US); Song Xue, Newton, MA (US); Robert C. Livingston, Arlington, MA (US); Kwame Wiredu Nti-Addae, Tewksbury, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/315,226

(22) PCT Filed: Jul. 6, 2017

(86) PCT No.: PCT/US2017/040827
§ 371 (c)(1),
(2) Date: Jan. 4, 2019

(87) PCT Pub. No.: WO2018/009609
PCT Pub. Date: Jan. 11, 2018

(65) Prior Publication Data
US 2019/0169179 A1 Jun. 6, 2019

Related U.S. Application Data

(60) Provisional application No. 62/359,466, filed on Jul. 7, 2016.

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
CPC .................. C07B 2200/13; C07D 413/14
See application file for complete search history.

(56) References Cited

U.S. PATENT DOCUMENTS

| | | | | |
|---|---|---|---|---|
| 4,432,987 A | * | 2/1984 | Barth | C07D 499/00 |
| | | | | 514/193 |
| 5,721,359 A | * | 2/1998 | Dunn | C07D 501/00 |
| | | | | 540/227 |
| 7,145,002 B2 | * | 12/2006 | Brands | C07D 477/20 |
| | | | | 540/350 |

FOREIGN PATENT DOCUMENTS

| | | | |
|---|---|---|---|
| WO | 2014/144100 A2 | | 9/2014 |
| WO | WO 2014/144100 | * | 9/2014 |
| WO | WO 2015/106268 | * | 6/2015 |
| WO | 2015/106268 A1 | | 7/2015 |

OTHER PUBLICATIONS

H Brittain, ed. Polymorphism in Pharmaceutical Solids (1999) p. 235-238.*

(Continued)

*Primary Examiner* — Valerie Rodriguez-Garcia
(74) *Attorney, Agent, or Firm* — McCarter & English, LLP; Steven G. Davis; Xin Zhang

(57) ABSTRACT

The present disclosure relates to crystalline solid forms of a stimulator of soluble guanylate cyclase (sGC), Compound I:

(Continued)

(56) References Cited

OTHER PUBLICATIONS

Bastin et al., Salt Selection and Optimisation Procedures for Pharmaceutical New Chemical Entities. Org Proc Res Dev. 2000;4(5):427-35.
Brittain et al., Spectral methods for the characterization of polymorphs and solvates. J Pharm Sci. Apr. 1997;86(4):405-12.
Brittain et al., X-ray Diffraction III: Pharmaceutical Applications of X-ray Powder Diffraction. Spectroscopy. Jul. 2001;16(7):14-7.
Byrn et al., Pharmaceutical solids: a strategic approach to regulatory considerations. Pharm Res. Jul. 1995;12(7):945-54.
Caira, Crystalline Polymorphism of Organic Compounds. Topics in Current Chemistry. 1998;198:163-208.
International Search Report and Written Opinion for Application No. PCT/US2017/040827, dated Oct. 10, 2017, 8 pages.
Balbach et al., Pharmaceutical evaluation of early development candidates "the 100 mg-approach". Int J Pharm. May 4, 2004;275(1-2):1-12.
Singhal et al., Drug polymorphism and dosage form design: a practical perspective. Adv Drug Deliv Rev. Feb. 23, 2004;56(3):335-47.

\* cited by examiner

Compound I

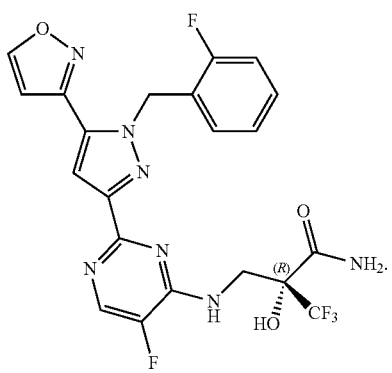

Also provided herein are methods for the preparation of these solid forms. The invention also relates to pharmaceutical formulations and dosage forms comprising these solid forms and their uses thereof, alone or in combination with one or more additional agents, for treating and/or preventing various diseases or disorders; these diseases or disorders are ones that may benefit from sGC stimulation or from an increase in the concentration of nitric oxide (NO) and/or cyclic guanosine monophosphate (cGMP).

24 Claims, 12 Drawing Sheets

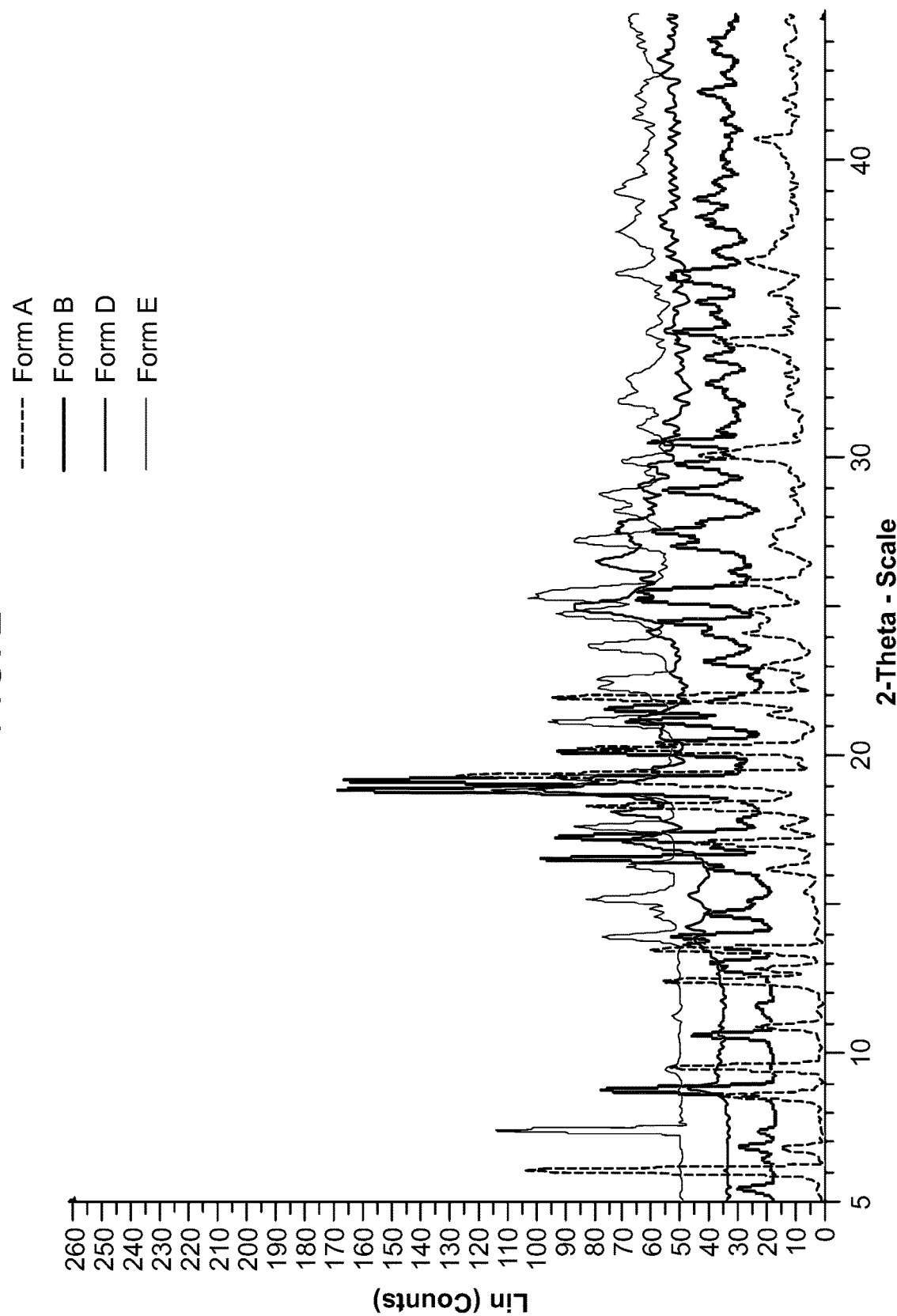

SUBSTITUTE SHEET (RULE 26)

Form D

— Form D, Initial
— Form D, 14 months at 40°C/75% RH

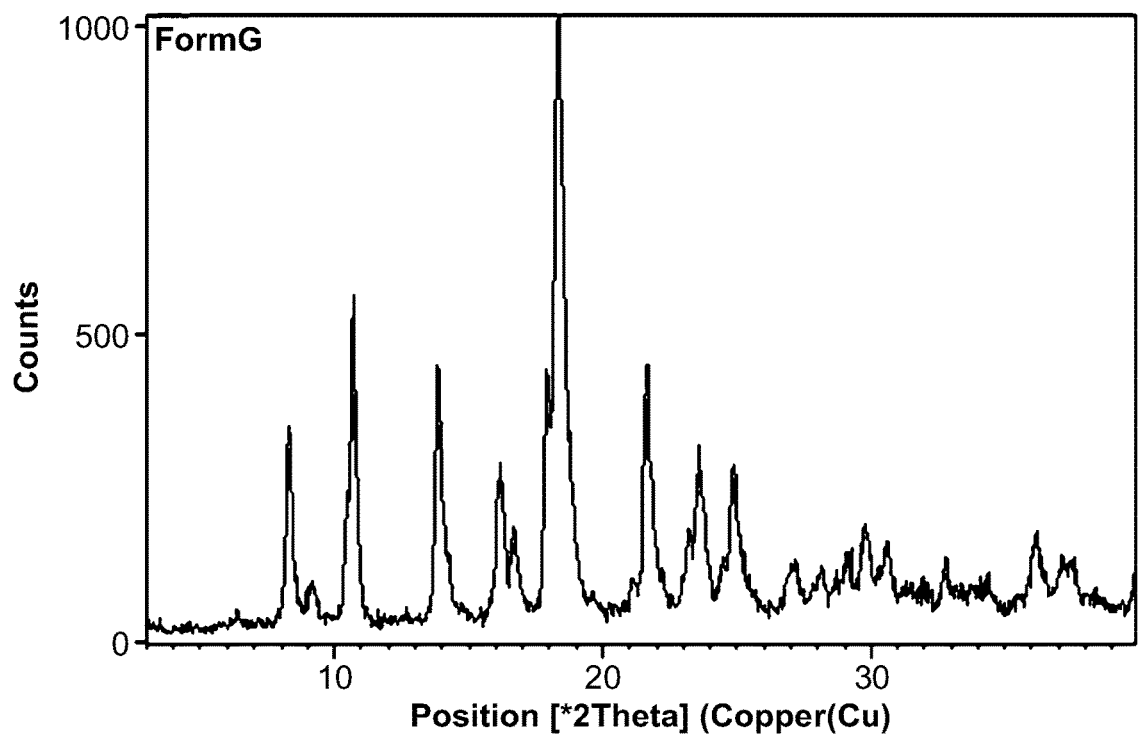
FIG. 9
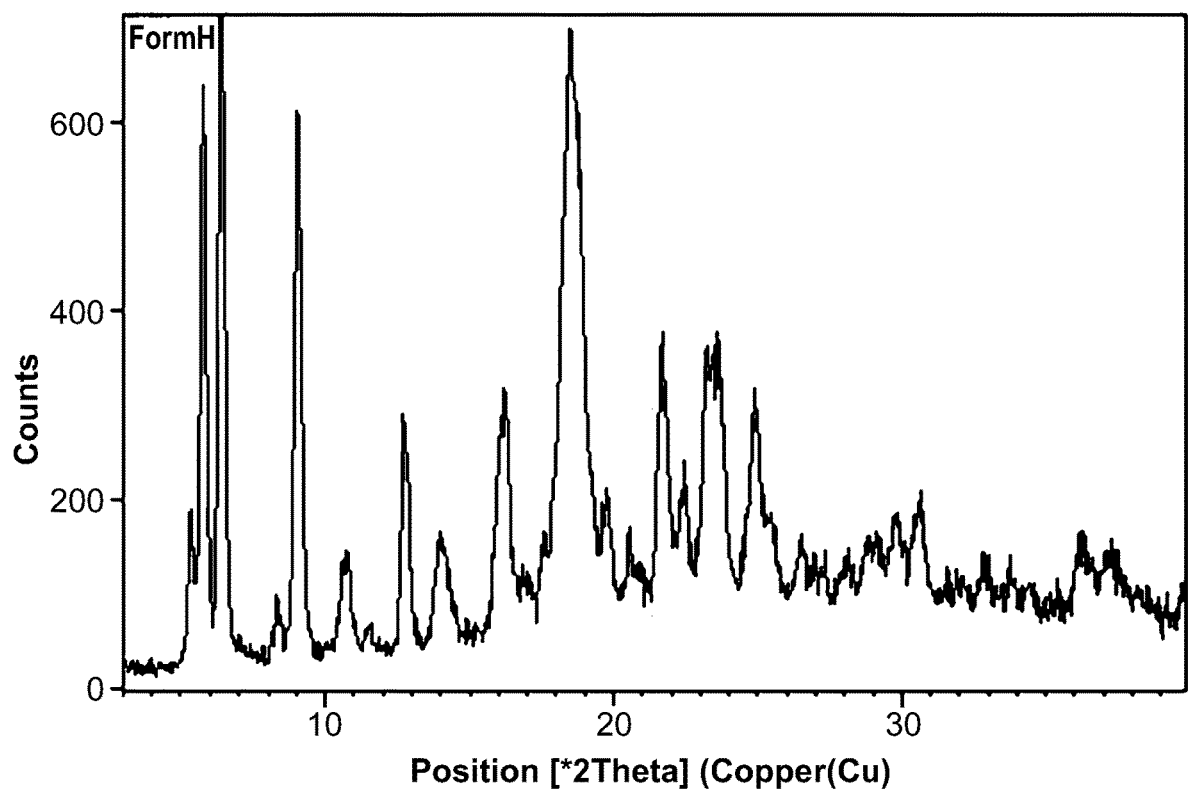

SOLID FORMS OF AN SGC STIMULATOR

CROSS-REFERENCE TO RELATED APPLICATIONS

This application is a 35 U.S.C. § 371 national stage filing of International Application No. PCT/US2017/040827, filed on Jul. 6, 2017, which claims the benefit of the filing date, under 35 U.S.C. § 119(e), of U.S. Provisional Application No. 62/359,466, filed on Jul. 7, 2016. The entire content of each of the foregoing applications is hereby incorporated by reference.

FIELD OF THE INVENTION

The present disclosure relates to solid forms of a stimulator of soluble guanylate cyclase (sGC). Also provided herein are methods for the preparation of these solid forms. The invention also relates to pharmaceutical formulations and dosage forms comprising these solid forms and their uses thereof, alone or in combination with one or more additional agents, for treating and/or preventing various diseases or disorders; these diseases or disorders are ones that may benefit from sGC stimulation or from an increase in the concentration of nitric oxide (NO) and/or cyclic guanosine monophosphate (cGMP).

BACKGROUND OF THE INVENTION sGC is the primary receptor for NO in vivo. sGC can be activated via both NO-dependent and NO-independent mechanisms. In response to this activation, sGC converts Guanosine-5'-triphosphate (GTP) into the secondary messenger cGMP. The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure. Experimental and clinical evidence indicates that reduced concentrations orbioavailability of NO and/or diminished responsiveness to endogenously produced NO contributes to the development of disease.

NO-independent, heme-dependent sGC stimulators, have shown several important differentiating characteristics, when compared to sGC activators, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed.

Compounds that stimulate sGC in an NO-independent manner offer considerable advantages over other current alternative therapies that target the aberrant NO pathway. There is a need to develop novel, well-characterized stimulators of sGC. Compound I is an sGC stimulator that has demonstrated efficacy for the treatment of a number of NO related disorders in preclinical models. Compound I was previously described in WO2014144100, Example 1, as a light orange solid. Compound I may be present in various crystalline forms and may also form several pharmaceutically acceptable salts.

The properties of a solid relevant to its efficacy as a drug can be dependent on the form of the solid. For example, in a drug substance, variation in the solid form can lead to differences in properties such as solubility and dissolution rate, surface properties (e.g., wettability), powder properties (flow, cohesion, bulk density, mixing behavior, compressibility, static, etc.), tablet properties (hardness, homogeneity, friability, disintegration, stability to heat and humidity, etc.), oral absorption, bioavailability, storage properties (caking, hygroscopicity), toxicology results and clinical trial results.

Characterization of polymorphs is useful in preventing certain problems from arising during clinical trials and/or commercialization of drugs, for instance, to avoid inconsistency of drug substance and products (e.g. inconsistencies from lot to lot), hydration or dehydration of hydrates, chemical degradation, amorphization or polymorphic transformation in drug product. A polymorph might also be preferred if it improves the solubility and/or bioavailability compared to another polymorph of the compound or to its amorphous form. It might also be preferred because it imparts increased physical or chemical stability, it provides a higher melting point (leading to improved mechanical properties), it has more acceptable taste or smell, or more neutral pH, and so on.

SUMMARY OF THE INVENTION

In one aspect, the invention relates to crystalline solid forms of Compound I, depicted below:

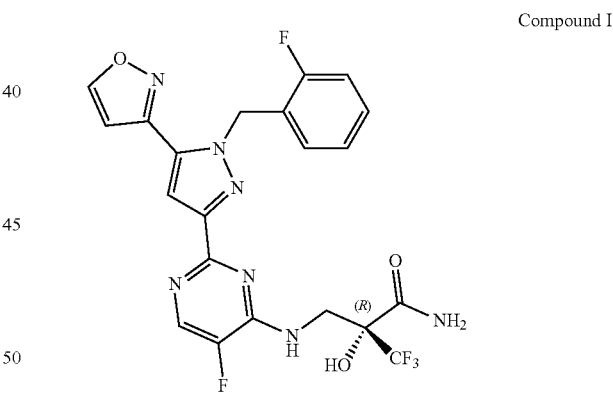

Compound I

For purposes of this disclosure, "Compound I," unless otherwise specifically indicated, refers to the free base or to the hydrochloric acid salt of the structure denoted above. Compound I, as its crystalline free base, is highly polymorphic and known to have seven crystalline forms (Forms A, B, D, E, F, G and H) as well as multiple solvates. Compound I was previously described in WO2014144100, Example 1, as a light orange solid.

In one embodiment, the crystalline solid forms of Compound I here disclosed are polymorphs of the free base. In another embodiment, a crystalline solid form of Compound I is the hydrochloric acid salt. In one embodiment, the polymorphs of Compound I are crystalline free base forms. In another embodiment, they are solvates.

In another aspect, also provided herein are methods for the preparation of the above described crystalline free forms and salts of Compound I.

In another aspect, the invention relates to pharmaceutical compositions comprising one or more of the polymorphs of Compound I herein disclosed, or the hydrochloric acid salt of Compound I, and at least one pharmaceutically acceptable excipient or carrier. In another embodiment, the invention relates to pharmaceutical dosage forms comprising said pharmaceutical compositions.

In another embodiment, the invention relates to a method of treating a disease, health condition or disorder in a subject in need thereof, comprising administering, alone or in combination therapy, a therapeutically effective amount of a polymorph of Compound I herein disclosed, or a mixture of polymorphs thereof, or its hydrochloric acid salt, to the subject; wherein the disease or disorder is one that may benefit from sGC stimulation or from an increase in the concentration of NO and/or cGMP.

DESCRIPTION OF THE FIGURES

FIG. 2: Shows superimposed XRPD patters of (from bottom to top, scaled, with offset) Form A, Form B, Form D and Form E in the 2-theta-scale range of 5 to 45.

FIG. 8: Shows XRPD pattern of Form G, in the 2-theta scale range of 3 to 40.

FIG. 9: Shows XRPD pattern of Form H, in the 2-theta scale range of 3 to 40.

Figure 1:
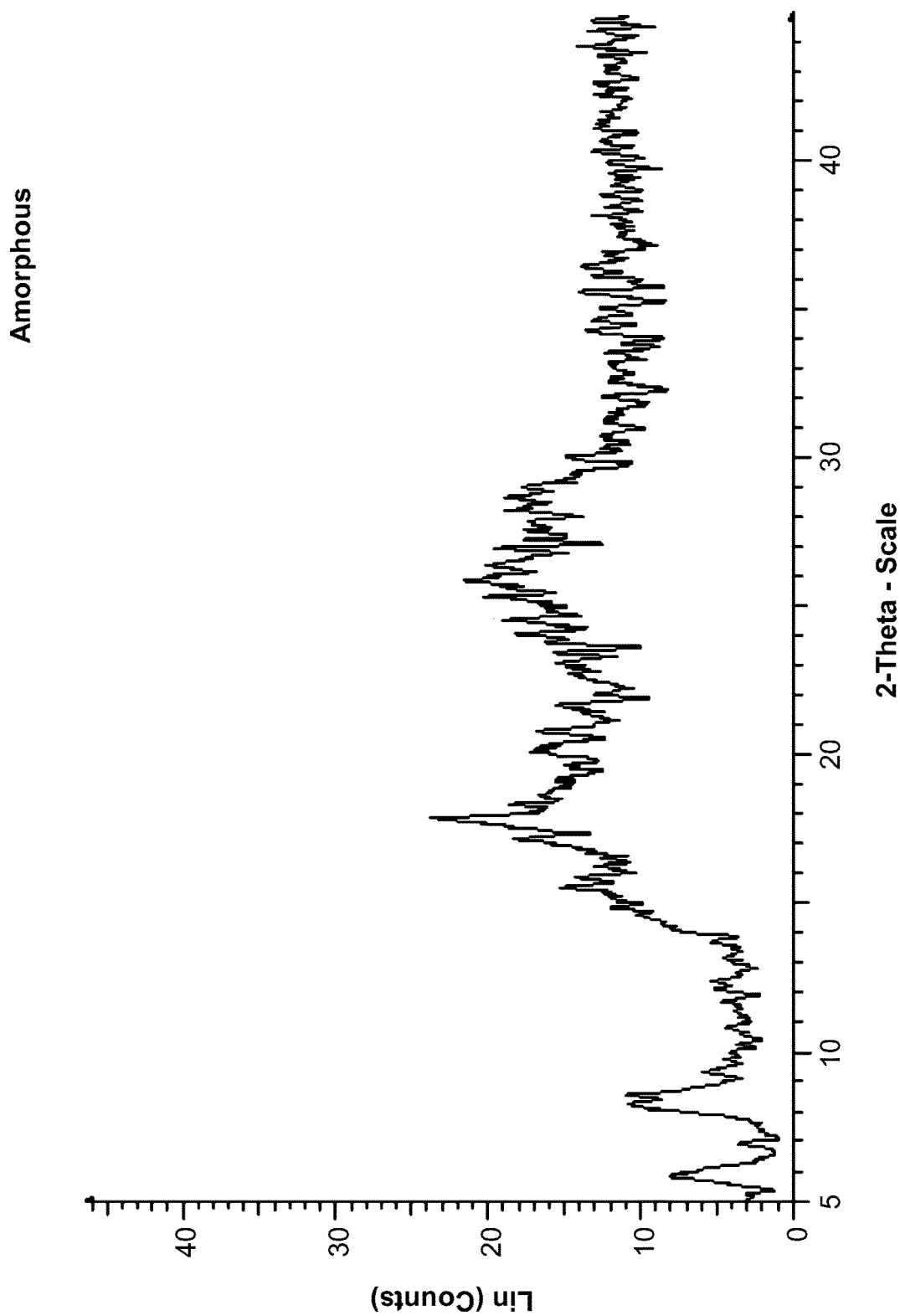
FIG. 1: Shows an XRPD pattern of the amorphous form of Compound I

The figures are provided by way of examples and are not intended to limit the scope of the present invention.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, $75^{th}$ Ed. 1994. Additionally, general principles of organic chemistry are described in "Organic Chemistry", Thomas Sorrell, University Science Books, Sausalito: 1999, and "March's Advanced Organic Chemistry", $5^{th}$ Ed., Smith, M. B. and March, J., eds. John Wiley & Sons, New York: 2001, which are herein incorporated by reference in their entirety.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

As used herein, a "solid form" of Compound I is characterized by or refers to a particular solid phase lattice structure (at the unit cell scale) of said compound.

A compound, such as Compound I, may be present in its "neat form" or "free base form" and the free base form can either be crystalline or amorphous. The free base form of a compound is formed only by molecules of said compound.

As used herein, "amorphous" or "amorphous form" is a solid form with no long-range molecular order that, therefore, lacks a distinctive X-ray powder diffraction pattern (XRPD).

A "crystal" or "crystalline form" is a homogenous solid which is formed by a repeating, three-dimensional pattern of atoms, ions, or molecules, having fixed distances between constituent parts. The term "crystal" can also be used to designate the unit cell of such a pattern.

As used herein "crystallization" is the process that leads to the formation of solid crystals from a solution, melt, vapor, a different solid phase or, more rarely, deposited directly from a gas. Crystallization can be a natural or an artificial process. Crystallization is also a chemical solid-liquid separation technique, in which mass transfer of a solute from the liquid solution to a pure solid crystalline phase occurs.

As used herein, "polymorphism" is the ability of a compound (e.g., Compound I) to exist in more than one crystalline form, or to crystallize with different crystal structures. A "polymorph" is each of the different crystal structures of the compound (e.g., Compound I). Polymorphs are crystal structures of the free form of the compound (i.e., crystalline free forms) or solvates thereof (i.e., "multi-component crystalline forms"), in which the compound, e.g., Compound I, crystallizes with a solvent. In some embodiments, when the solvent that crystallizes is water, solvates are hydrates.

As used herein, a "solvate" refers to an association or complex of one or more solvent molecules (molecules of a substance that is liquid at room temperature) with a compound (e.g., Compound I) in a crystalline form, giving rise to a new characteristic crystalline solid. This disclosure describes several "ansolvates" of the free base form of Compound I (i.e., solid forms of Compound I which are crystalline free forms and are not solvates).

There are other types of solid forms that may be formed. For example, when both compounds in a multi-component crystalline form would be independently solids when present at room temperature, the resulting solid form is referred to as a "co-crystal".

When one of the components in the solid form has clearly transferred a proton to the other component, and the resulting components of the multi-component crystalline form are ionic, the resulting solid form is referred to as a "salt".

In co-crystals, no ion transfer takes place between the different components of the solid form, so that the resulting components are present in non-ionic form. In co-crystals the two (or more) components of the multi-component crystalline form are solids and non-ionic when present independently of each other at room temperature.

Whether a salt or a co-crystal is formed when two substances are mixed will be determined by how large the difference between the pKas of the two components is.

The instant disclosure describes one solid form of Compound I that is a salt, (the hydrochloric acid salt).

There are many crystallization techniques available that allow a person skilled in the art to obtain crystalline materials. For crystallization to occur from a solution, the solution must be "supersaturated". This means that the solution has to contain more solute entities (molecules or ions) dissolved than it would contain under the thermodynamic equilibrium conditions ("saturated solution"). This can be achieved by various methods, for instance: 1) "cooling crystallization"; 2) addition of a second solvent to reduce the solubility of the solute (a technique known as "antisolvent crystallization"); 3) chemical reactions; 4) change in pH; and 5) slurry conversion in organic and/or aqueous solvent systems are the most common methods used in industrial practice. Other methods, such as "solvent evaporation crystallization", can also be used. As used herein, "supersaturation" is the difference between the concentration (C) of the solution and the concentration (C*) at equilibrium at the same temperature. It is measured in concentration units.

The term "chemically stable", to characterize a solid form of Compound I (e.g., a polymorph or a salt) indicates that it does not decompose into one or more new different chemical compounds when subjected to specified conditions, e.g., 40° C./75% relative humidity, for a specific period of time, e.g., 1 day, 2 days, 3 days, 1 week, 2 weeks, 1 month, 2 months, 3 months, 6 months, 12 months, 18 months, 24 months, or longer. In some embodiments, less than 25% of the polymorph of Compound I decomposes; in some embodiments, less than 20%, less than 15%, less than 10%, less than 5%, less than 3%, less than 1% or less than 0.5% of the polymorph of Compound I decomposes under the conditions specified. In some embodiments, no detectable amount of a given polymorph of Compound I decomposes under the specified conditions (as determined by the lowest detection limit of the analytical technique used) after a certain period of time.

The term "physically stable", to characterize a crystalline solid form of Compound I (e.g., a polymorph or a salt), means that the crystalline solid form does not change into one or more different crystalline solid forms of Compound I (e.g., a polymorph changing to a different polymorph of Compound I as measured by an analytical technique such as XRPD, etc.) or into the amorphous form, when subjected to specific conditions, e.g., 40° C./75% relative humidity, for a specific period of time. e.g., 1 day, 2 days, 3 days, 1 week, 2 weeks, 1 month, 2 months, 3 months, 6 months, 12 months, 18 months, 24 months, or longer. In some embodiments, less than 25% of the crystalline solid form of Compound I changes into one or more different solid forms (another crystalline solid form or the amorphous form) when subjected to specified conditions. In some embodiments, less than 20%, less than 15%, less than 10%, less than 5%, less than 3%, less than 1%, or less than 0.5% of the crystalline solid form of Compound I changes into one or more different crystalline solid forms of Compound I or the amorphous form when subjected to the specified conditions. In some embodiments, no detectable amount of a given solid form of Compound I changes into one or more different solid forms of Compound I under the specified conditions.

The term "substantially pure" when referring to a designated crystalline solid form of Compound I (e.g., a polymorph or salt of Compound I described herein) means that the designated crystalline solid form contains less than 20% (by weight) of residual components (such as alternate polymorph(s) of Compound I, or the amorphous formor additional solvent molecules or impurities). In other embodiments, a substantially pure crystalline solid form of Compound I contains less than 10% (by weight) of alternate polymorphs of Compound I, or the amorphous formor additional solvent molecules or impurities. In other embodiments, it contains less than 5% (by weight) of alternate polymorphs of Compound I, or the amorphous formor additional solvent molecules or impurities. In still other embodiments, it contains less than 1% (by weight) of alternate polymorphs of Compound I, or the amorphous form or additional solvent molecules or impurities.

The term "substantially similar" as used herein, when referring to a spectrum, trace, heat curve, etc., characteristic of a designated solid form of Compound I (e.g., a polymorph or salt of Compound I described herein) means that the spectrum, trace, heat curve, etc., being referred to contains fewer than 10% of peaks that are different from the peaks in the spectrum, trace or curve shown as a figure in this specification and assigned to a particular solid form of Compound I being discussed. In other embodiments, it contains fewer than 5% of peaks that are different. In still other embodiments, it contains fewer than 1% of peaks that are different.

When comparing XRPD spectra, a spectrum will be "substantially similar" to one shown in this disclosure for a particular solid form of Compound I, wherein the characteristic peaks in said spectrum are measured at the same values of °2θ as those shown in the figure of this disclosure, or within a range of + or –0.5 units of °2θ from those peaks shown in said figure. The XRPD of a solid form of Compound I will be considered to be "essentially unchanged" after a certain length of time under certain conditions, if the XRPD of said solid form before and after said certain length of time under said certain conditions is "substantially similar".

This disclosure often refers to evaluating a chemical, physical or biological parameter disclosed herein. One of skill in the art will understand that such parameters can be substituted with other chemical, physical or biological parameters which, though not disclosed herein, are essentially similar in terms of identifying the solid form.

EMBODIMENTS

In one aspect, the invention relates to crystalline solid forms of Compound I, depicted below:

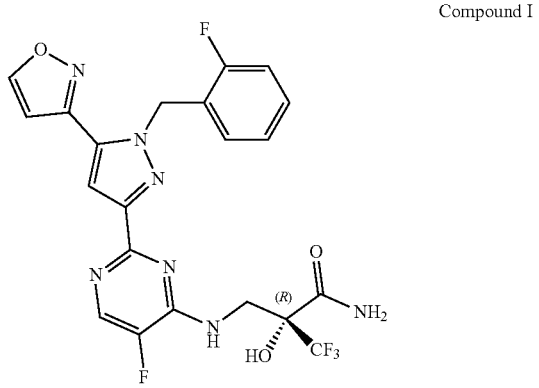

Compound I

Compound I is an sGC stimulator that has demonstrated efficacy for the treatment of a number of NO related disorders in preclinical models. Compound I may be present in various crystal forms or polymorphs. Some of these polymorphs are crystalline free base forms. Others are solvates. In some embodiments, a solvate is a hydrate. Compound I may also form several pharmaceutically acceptable salts, including its hydrochloric acid salt.

In one embodiment, the solid forms of Compound I here disclosed are polymorphs. In another embodiment, a solid form of Compound I is its hydrochloric acid salt. Compound I exists, at least, in seven neat polymorphs or crystalline free forms: Form A, Form B, Form D, Form E, Form F, Form G and Form H. Compound I was previously described in WO2014144100, Example 1, as a light orange solid.

In one embodiment, the crystalline solid form of Compound I is polymorph Form E. Form E is formed when crude Compound I, prepared as described in the Examples section, is dissolved in MeOH at >60° C. (e.g., >70° C.) to obtain a solution, followed by filtration, heating of the filtrate at >60° C., addition of water and cooling to room temperature (rt), followed by filtration and drying under vacuum at 80° C. over 72 hours.

In another embodiment, the crystalline solid form of Compound I is polymorph Form A. Form A is formed when Compound I is dissolved in ethyl acetate, at >70° C. to obtain a solution, followed by filtration, additional stirring of the filtrate at 20 to 25° C. over 16 hours to give a slurry, concentration of the slurry under vacuum, addition of heptane, further concentrating the resulting slurry, filtration, and drying under vacuum at 100° C. over 3 hours.

In another embodiment, polymorph Form A is formed when polymorph Form E is dissolved in ethyl acetate, at >70° C. to obtain a solution, followed by filtration, additional stirring of the filtrate at 20 to 25° C. over 16 hours to give a slurry, concentration of the slurry under vacuum, addition of heptane, further concentrating the resulting slurry, filtration, and drying under vacuum at 100° C. over 3 hours.

In another embodiment, polymorph Form A can be obtained directly from crude Compound I by heating in DMSO at higher than 60° C., followed by addition of water to form a slurry and filtration of the slurry.

In another embodiment, polymorph Form A is also isolated when the crude Compound I is slurried in a solvent at room temperature and allowed to stir for 14 to 30 hours. In some embodiments, the solvent is selected from heptane, isopropylacetate (IPAC), ethanol, ethyl acetate or decane, or a mixture thereof. The slurry is then filtered and dried under vacuum.

In another embodiment, the solid form of Compound I is polymorph Form D. Form D is formed when Form E, prepared as described above, is mixed with n-decane at 145-155° C. for 45 min to obtain a slurry, followed by cooling of the slurry to 20 to 30° C. over 1 hour, filtration and drying under vacuum at 80° C. over 72 hours.

In another embodiment, form D can be formed by heating any of the polymorph forms Form E, Form B, Form F, Form G or Form H, or mixtures thereof, neat (in the absence of solvent) at 180° C.

In another embodiment, the solid form of Compound I is polymorph Form B. Form B is formed when crude Compound I, prepared as described in the Examples section, is mixed with acetonitrile at 70-75° C. to form a solution, followed by filtration, additional heating of the filtrate at 70 to 75° C., addition of water, cooling to 52-62° C. to form a slurry, cooling of the slurry to 0-5° C. over more than 4 hours, filtration and drying under vacuum at 90-100° C. over a minimum of 30 h.

In another embodiment, the solid form of Compound I is polymorph Form F. Form F is obtained when Form A, prepared as described in the Examples section, is heated neat at 160° C.

In another embodiment, the solid form of Compound I is polymorph Form G. Form G is obtained when crude Compound I, prepared as described in the Examples section, is slurried in acetone at ambient temperatures for 2 hours, followed by filtration and drying under vacuum at 30 to 40° C. In another embodiment, polymorph Form G is obtained when polymorph Form H is stirred in acetone at rt (room temperature), followed by filtration and drying under vacuum at 30 to 40° C.

In another embodiment, the solid form of Compound I is polymorph Form H. Form H is obtained when crude compound I, prepared as described in the Examples section, is mixed with acetone at 45 to 50° C. to form a solution, followed by filtration, cooling to room temperature to form a slurry then stirring at room temperature for 5 hours, followed by filtration and drying under vacuum at 30 to 40° C.

In one aspect, the solid form of Compound I is polymorph Form A.

Figure 10:
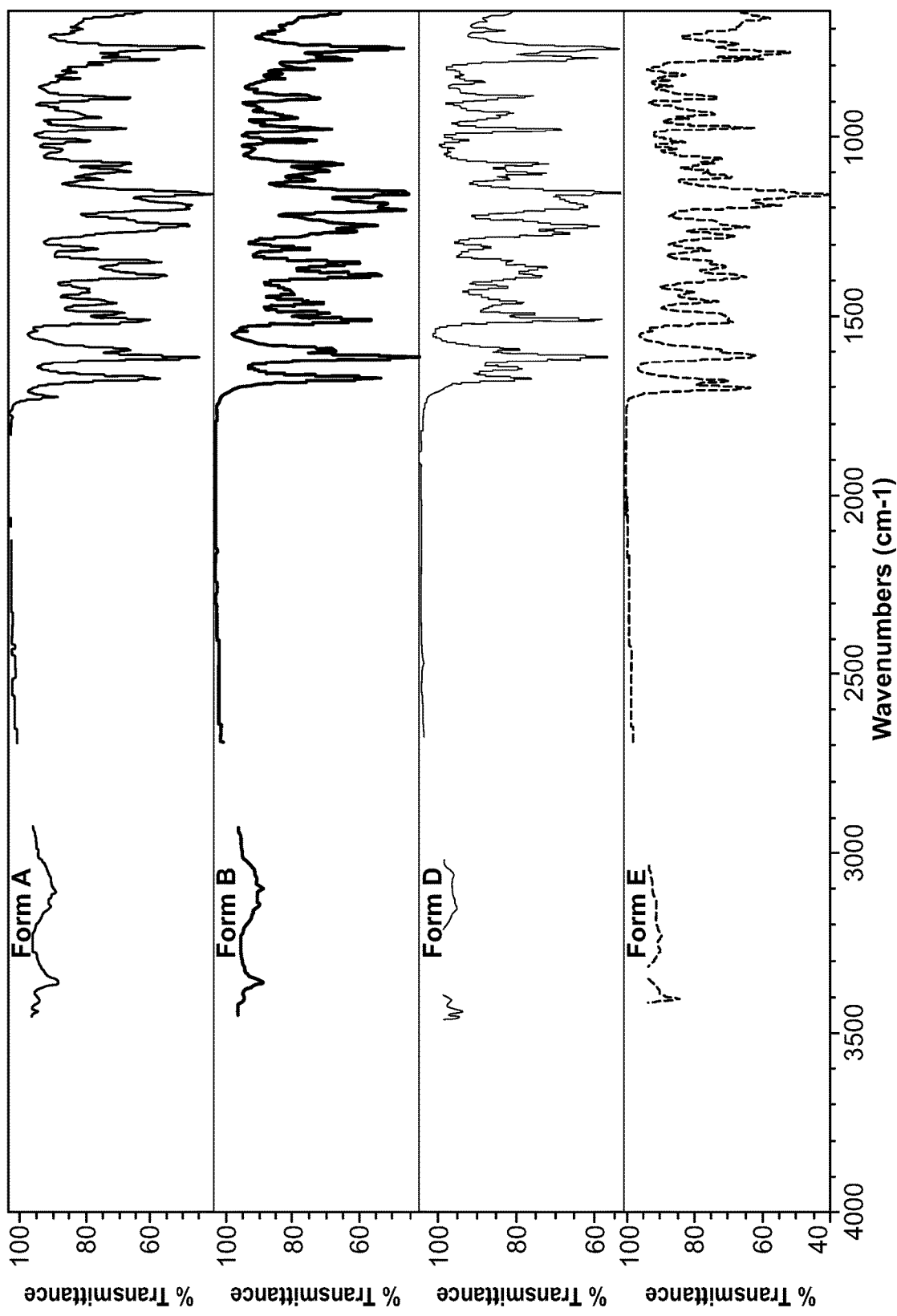
FIG. 10: Shows superimposed FT-Raman spectra of (from bottom to top, scaled, with offset) Form A, Form B, Form D and Form E in the wavenumber range from 1800 to 200 $cm^{-1}$.

In some embodiments, Form A is characterized by a FT-Raman spectrum substantially similar to that shown in FIG. 10.

In some embodiments, Form A is characterized in that its IR spectrum exhibits a band maximum at 1730 cm$^{-1}$.

Figure 3A:
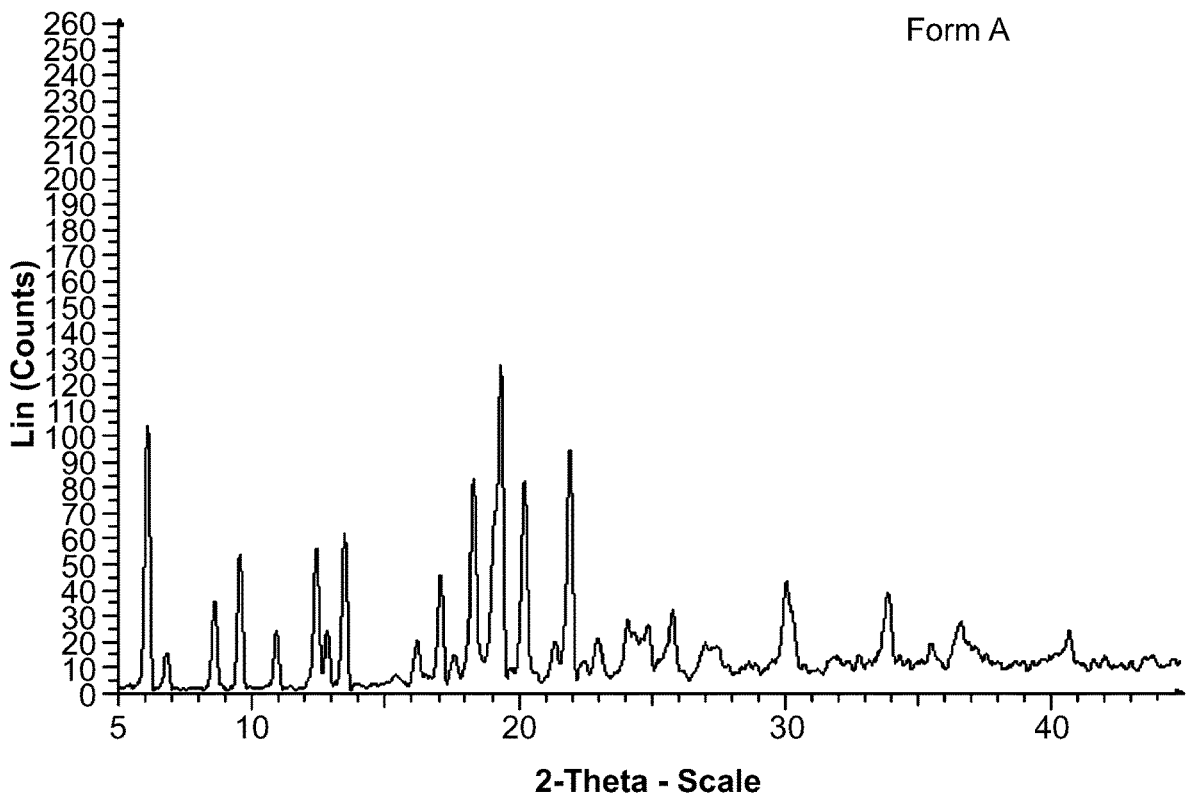
FIG. 3A: Shows XRPD pattern of Form A, in the 2-theta scale range of 5 to 45.

In some embodiments, Form A is characterized by an XRPD spectrum substantially similar to that shown in FIG. 2 or in FIG. 3A.

In other embodiments, Form A is characterized by one or more peaks in the XRPD spectrum selected from: 6.0, 18.3, 19.3, 20.2 and 22.0 °2θ.

In other embodiments, Form A is characterized by one or more peaks in the XRPD spectrum selected from: 6.0, 8.5, 9.5, 12.4-12.9, 13.4, 17.1, 18.3, 19.3, 20.2, 22.0, 30.1 and 34.1 °2θ.

In other embodiments, Form A is characterized by one or more peaks in the XRPD spectrum selected from: 6.0, 6.7, 8.5, 9.5, 10.9, 12.4-12.9, 13.4, 16.2, 17.1, 18.3, 19.3, 20.2, 22.0, 23.0, 24.1 to 24.8, 25.8, 30.1 and 34.1 °2θ.

Figure 3B:
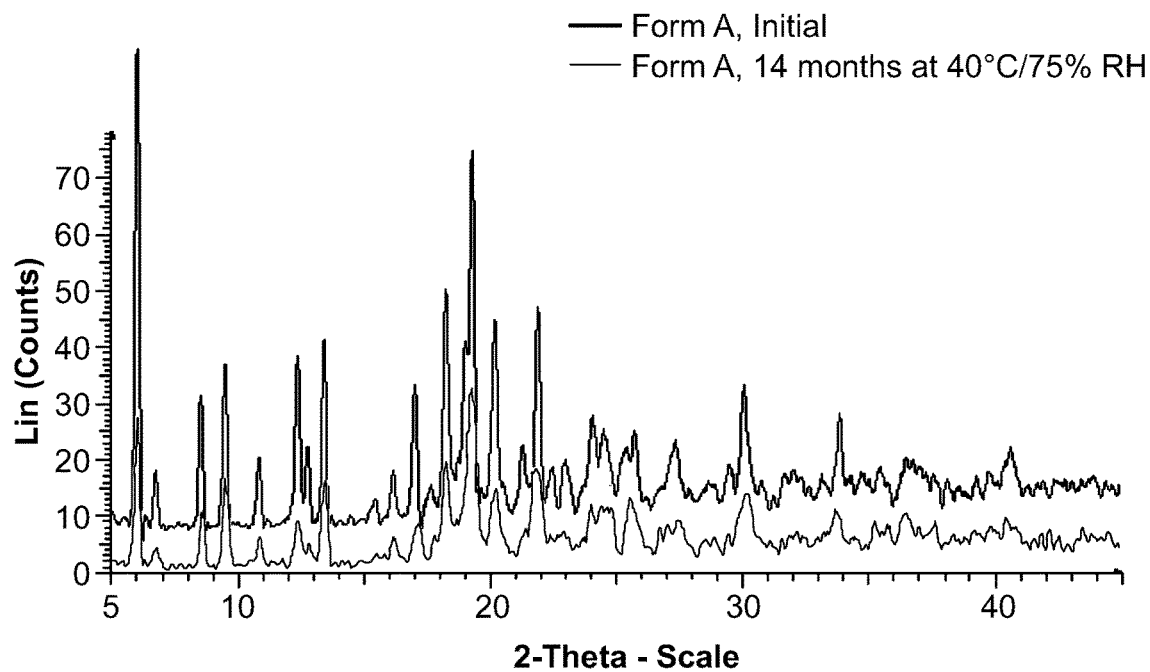
FIG. 3B: Shows XRPD pattern of Form A before and after storage for 14 months.
Figure 3C:
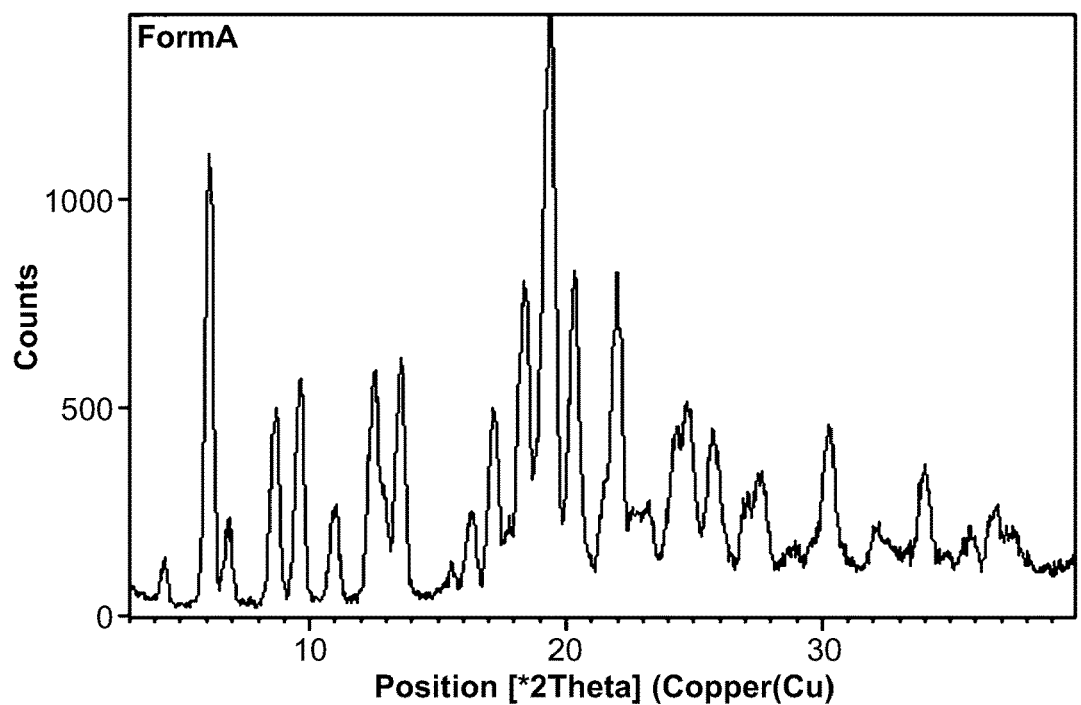
FIG. 3C: Shows XRPD pattern of Form A, in the 2-theta scale range of 3 to 40.

In some embodiments, Form A is characterized by an XRPD spectrum substantially similar to that shown in FIG. 3C.

In other embodiments, Form A is characterized by one or more peaks in the XRPD spectrum selected from: 6.1 (80.81% relative intensity or rel int), 18.4 (53.57%), 19.4 (100.00%), 20.3 (57.01%) and 22.0 (56.64) °2°.

In other embodiments, Form A is characterized by one or more peaks in the XRPD spectrum selected from: 6.1 (80.81% rel int), 9.6 (40.35%), 12.6 (41.26%), 13.6 (43.19%), 18.4 (53.57%), 19.4 (100.00%), 20.3 (57.01%) and 22.0 (56.64) °2θ.

In other embodiments, Form A is characterized by displaying an essentially unchanged XRPD trace when stored for 14 months under the stability conditions of 40° C. and 75% relative humidity. XRPD traces for Form A before and after storage under those conditions are shown in FIG. 3B.

In one aspect, the solid form of Compound I is polymorph Form B.

In some embodiments, Form B is characterized by a FT-Raman spectrum substantially similar to that shown in FIG. 10.

In some embodiments, Form B is characterized in that its IR spectrum exhibits a peak maximum at 1200 cm$^{-1}$.

Figure 4A:
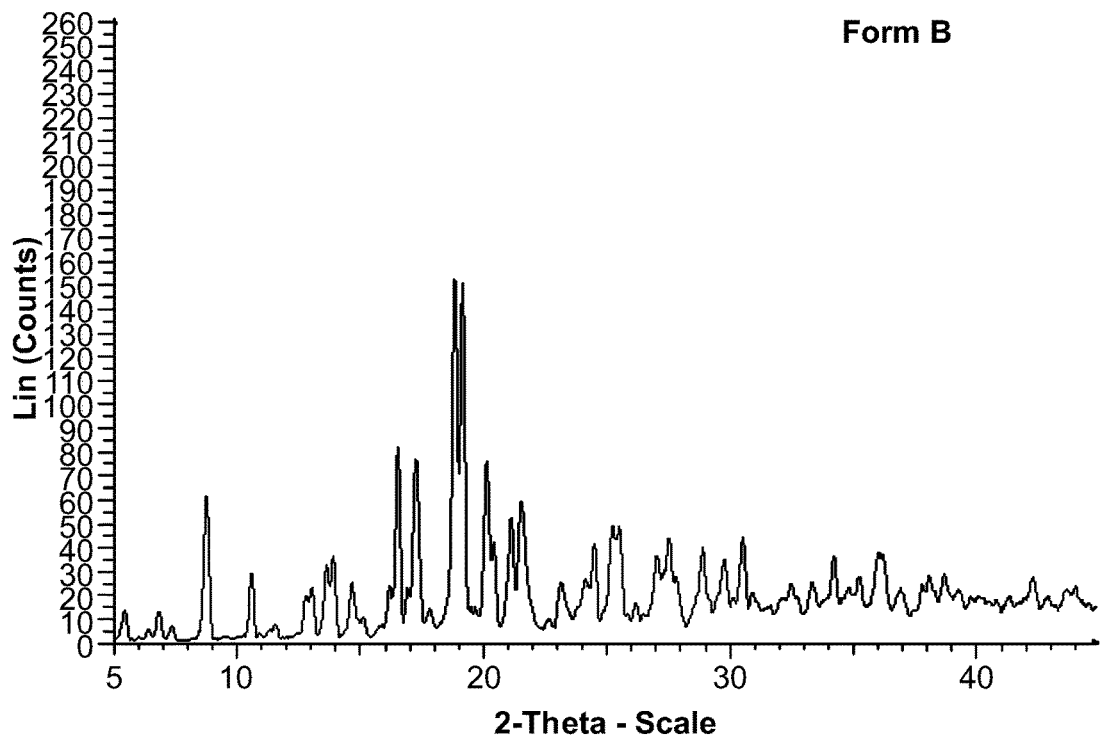
FIG. 4A: Shows XRPD pattern of Form B, in the 2-theta scale range of 5 to 45.

In some embodiments, Form B is characterized by an XRPD spectrum substantially similar to that shown in FIG. 2 or FIG. 4A.

In other embodiments, Form B is characterized by one or more peaks in the XRPD spectrum at 18.8 to 19.1 °2θ.

In another embodiment, Form B is characterized by one or more peaks in the XRPD spectrum selected from: 8.8, 16.4, 17.2, 18.8-19.1, 20.1, and 21.1-21.6 °2θ.

In another embodiment, Form B is characterized by one or more peaks in the XRPD spectrum selected from: 8.8, 10.6, 12.6-13.0, 14.6, 16.4, 17.2, 18.8-19.1, 20.1, 21.1-21.6, 24.5, 25.3, 27.0-27.5, 28.9, 29.8 and 30.5 °2θ.

Figure 4B:
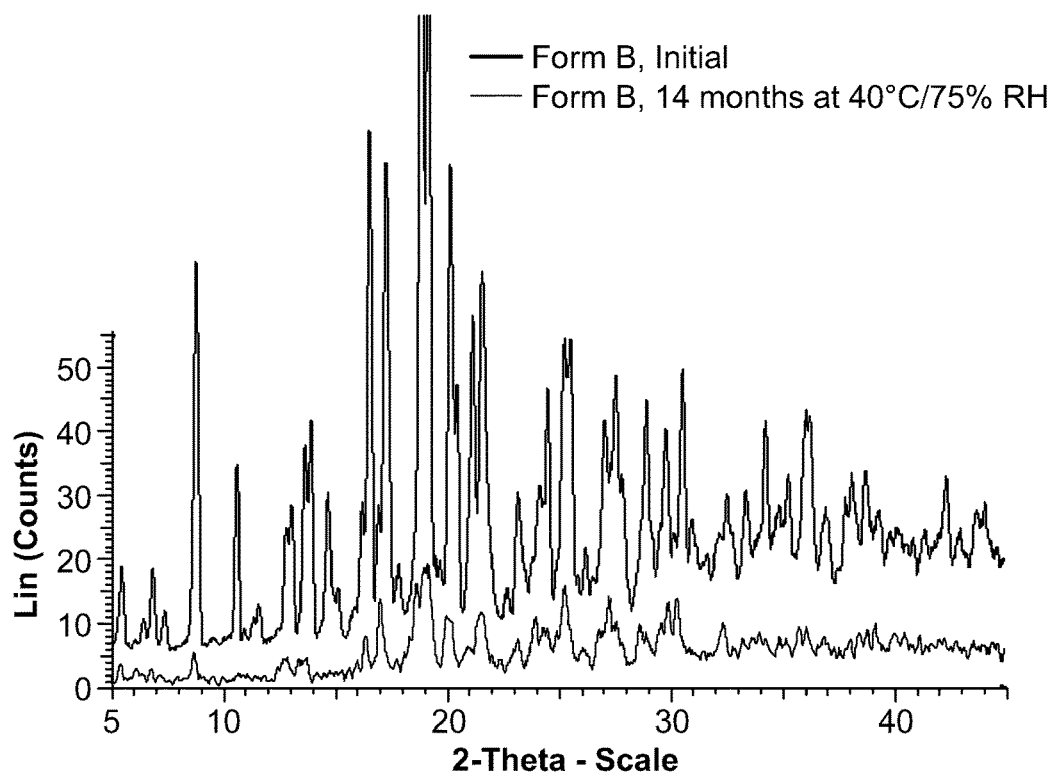
FIG. 4B: Shows XRPD pattern of Form B before and after storage for 14 months.
Figure 4C:
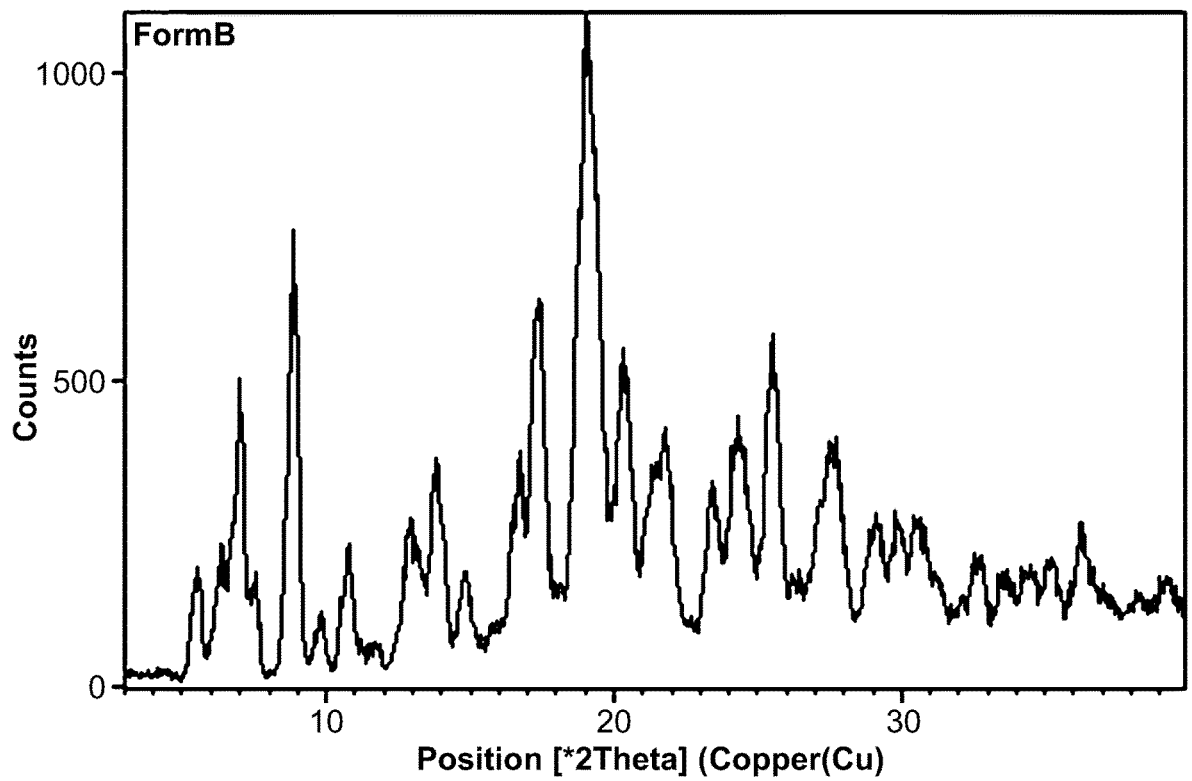
FIG. 4C: Shows XRPD pattern of Form B, in the 2-theta scale range of 3 to 40.

In some embodiments, Form B is characterized by an XRPD spectrum substantially similar to that shown in FIG. 4C.

In other embodiments, Form B is characterized by one or more peaks in the XRPD spectrum selected from: 8.9 (76.55% rel int), 17.4 (57.67%), 19.1 (100.00%), and 25.5 (52.26) °2θ.

In other embodiments, Form B is characterized by one or more peaks in the XRPD spectrum selected from: 7.0 (44.44% rel int), 8.9 (76.55%), 17.4 (57.67%), 19.1 (100.00%), 20.3 (49.78%), 21.8 (36.16%), and 25.5 (52.26) °2θ.

In other embodiments, Form B is characterized by displaying an essentially unchanged XRPD trace when stored for 14 months under the stability conditions of 40° C. and 75% relative humidity. XRPD traces for Form B before and after storage under those conditions are shown in FIG. 4B.

In one aspect, the solid form of Compound I is polymorph Form D.

In some embodiments, Form D is characterized by a FT-Raman spectrum substantially similar to that shown in FIG. 10.

In some embodiments Form D is characterized in that its IR spectrum exhibits band maxima at 1665, 1639 and 968 cm$^{-1}$. In some embodiments, Form D is characterized in that its IR spectrum exhibits a band maximum at 1665 cm$^{-1}$. In other embodiments, Form D is characterized in that its IR spectrum exhibits a band maximum at 1639 cm$^{-1}$. In other embodiments, Form D is characterized in that its IR spectrum exhibits a band maximum at 968 cm$^{-1}$.

Figure 5A:
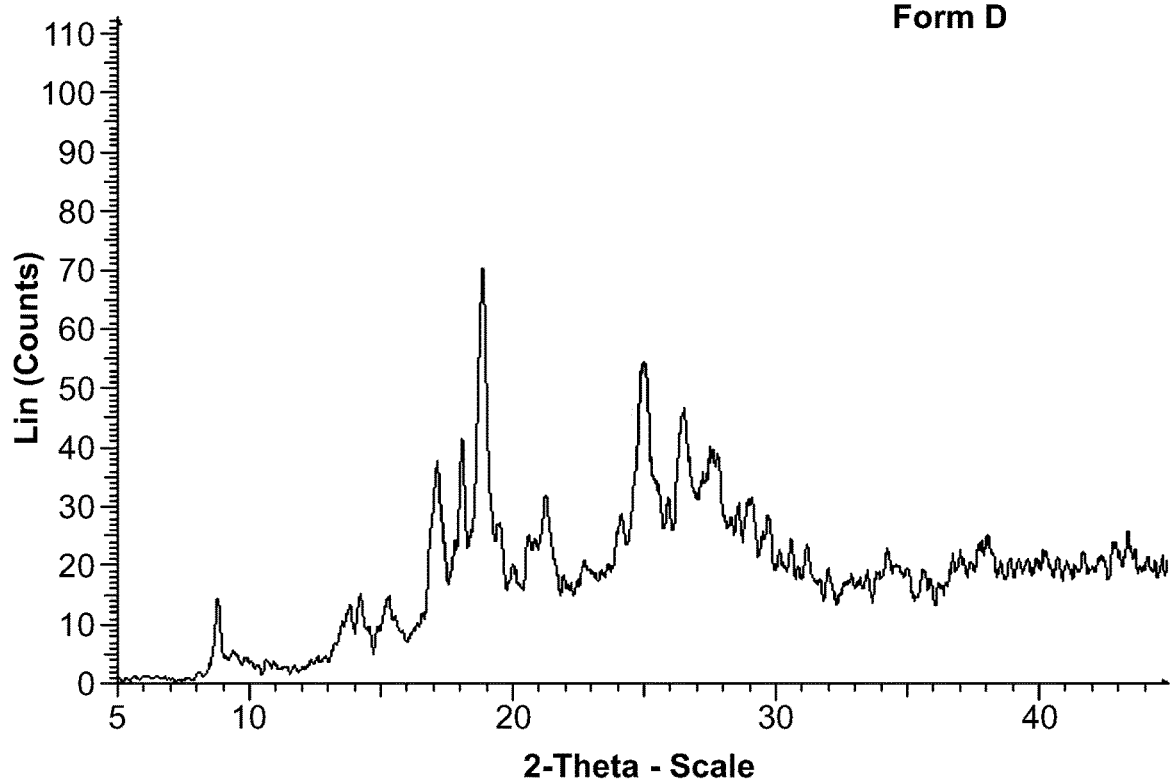
FIG. 5A: Shows XRPD pattern of Form D, in the 2-theta scale range of 5 to 45.

In some embodiments, Form D is characterized by an XRPD spectrum substantially similar to that shown in FIG. 2 or FIG. 5A.

Figure 5B:
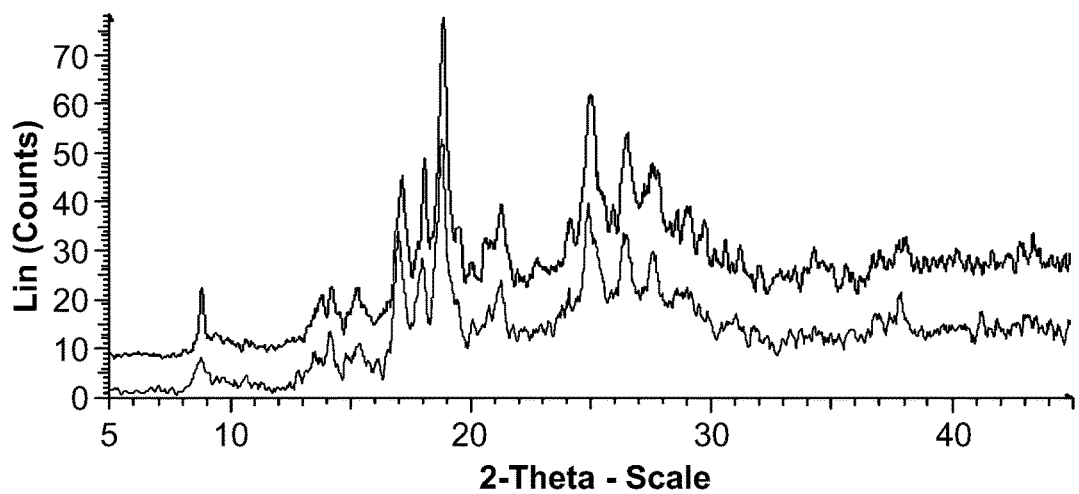
FIG. 5B: Shows XRPD pattern of Form D before and after storage for 14 months.

In other embodiments, Form D is characterized by displaying an essentially unchanged XRPD trace when stored for 14 months under the stability conditions of 40° C. and 75% relative humidity. XRPD traces for Form D before and after storage under those conditions are shown in FIG. 5B.

In other embodiments, Form D is characterized by a peak in the XRPD spectrum at 18.8 °2θ.

In another embodiment, Form D is characterized by one or more peaks in the XRPD spectrum selected from: 17.1, 18.1, 18.8 and 25.0 °2θ.

In another embodiment, Form D is characterized by one or more peaks in the XRPD spectrum selected from: 8.8, 17.1, 18.1, 18.8 and 25.0 °2θ.

Figure 5C:
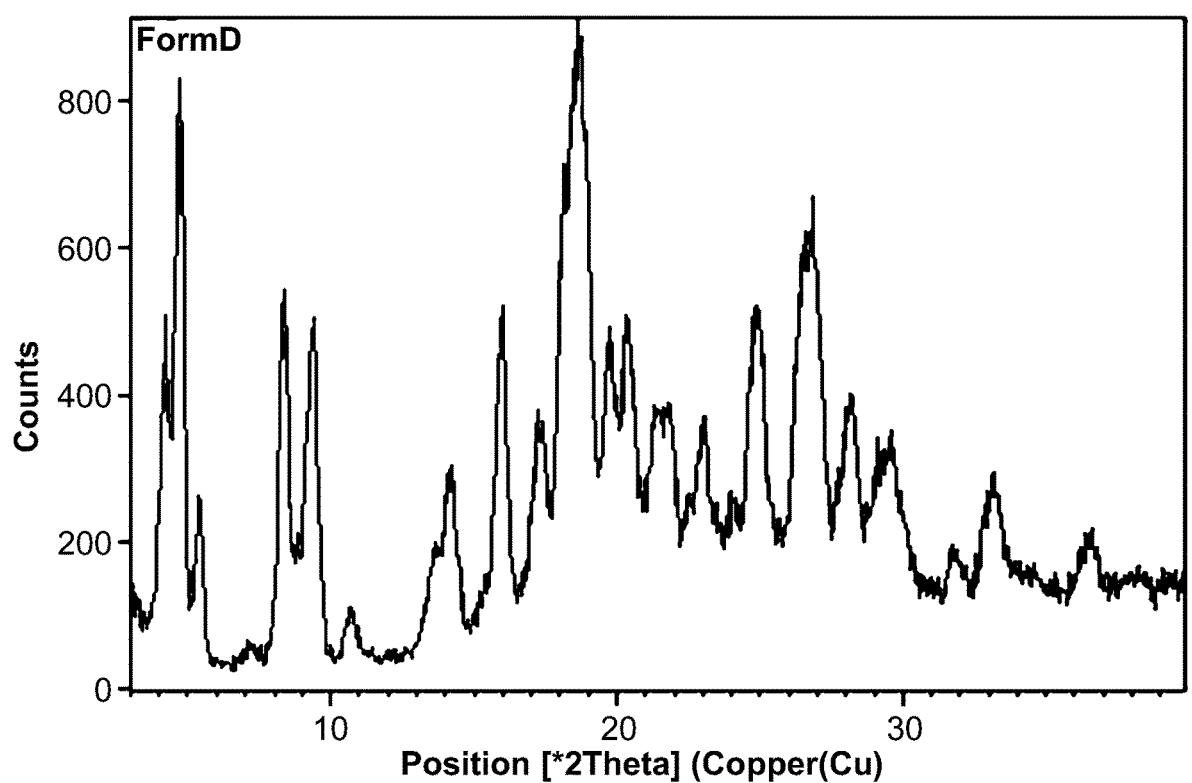
FIG. 5C: Shows XRPD pattern of Form D, in the 2-theta scale range of 3 to 40.

In some embodiments, Form D is characterized by an XRPD spectrum substantially similar to that shown in FIG. 5C.

In other embodiments, Form D is characterized by one or more peaks in the XRPD spectrum selected from: 4.7 (97.11% rel int), 18.1 (80.97%), 18.6 (100.00%), and 26.8 (65.25) °2θ.

In other embodiments, Form D is characterized by one or more peaks in the XRPD spectrum selected from: 4.7 (97.11% rel int), 8.3 (64.04%), 18.1 (80.97%), 18.6 (100.00%), and 26.8 (65.25) °2θ.

In one aspect, the solid form of Compound I is polymorph Form E.

In some embodiments, Form E is characterized by a FT-Raman spectrum substantially similar to that shown in FIG. 10.

In some embodiments Form E is characterized in that its IR spectrum exhibits band maxima at 1690 and 1515 cm$^{-1}$. In some embodiments Form E is characterized in that its IR spectrum exhibits a peak maximum at 1690 cm$^{-1}$. In some embodiments Form E is characterized in that its IR spectrum exhibits a peak maximum at 1515 cm$^{-1}$.

Figure 6:
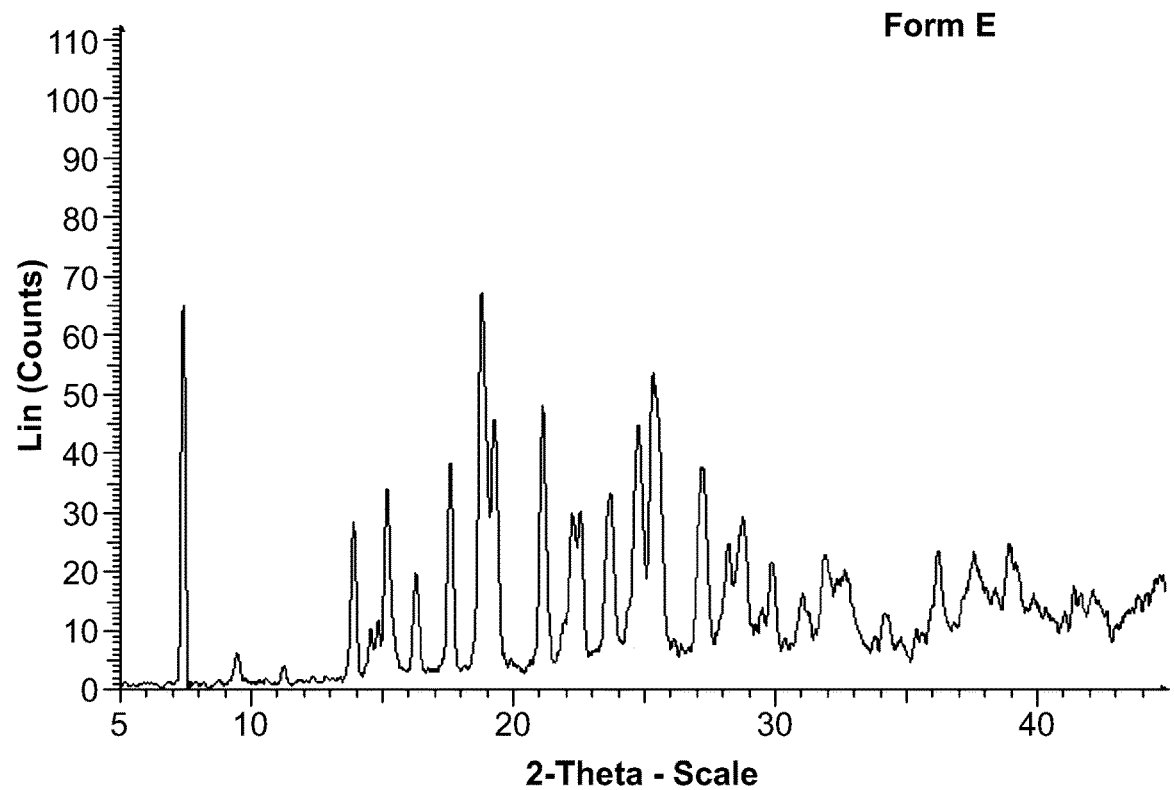
FIG. 6: Shows XRPD pattern of Form E, in the 2-theta scale range of 5 to 45.

In some embodiments, Form E is characterized by an XRPD spectrum substantially similar to that shown in FIG. 2 or FIG. 6.

In other embodiments, Form E is characterized by one or more peaks in the XRPD spectrum selected from: 7.4, 18.8-19.3, 21.1, 24.8 and 25.5 °2θ.

In other embodiments, Form E is characterized by one or more peaks in the XRPD spectrum selected from: 7.4, 13.9, 15.1, 16.3, 17.6, 18.8-19.3, 21.1, 22.3-22.5, 24.8, 25.5 and 27.1 °2θ.

In one aspect, the solid form of Compound I is polymorph Form F.

Figure 7:
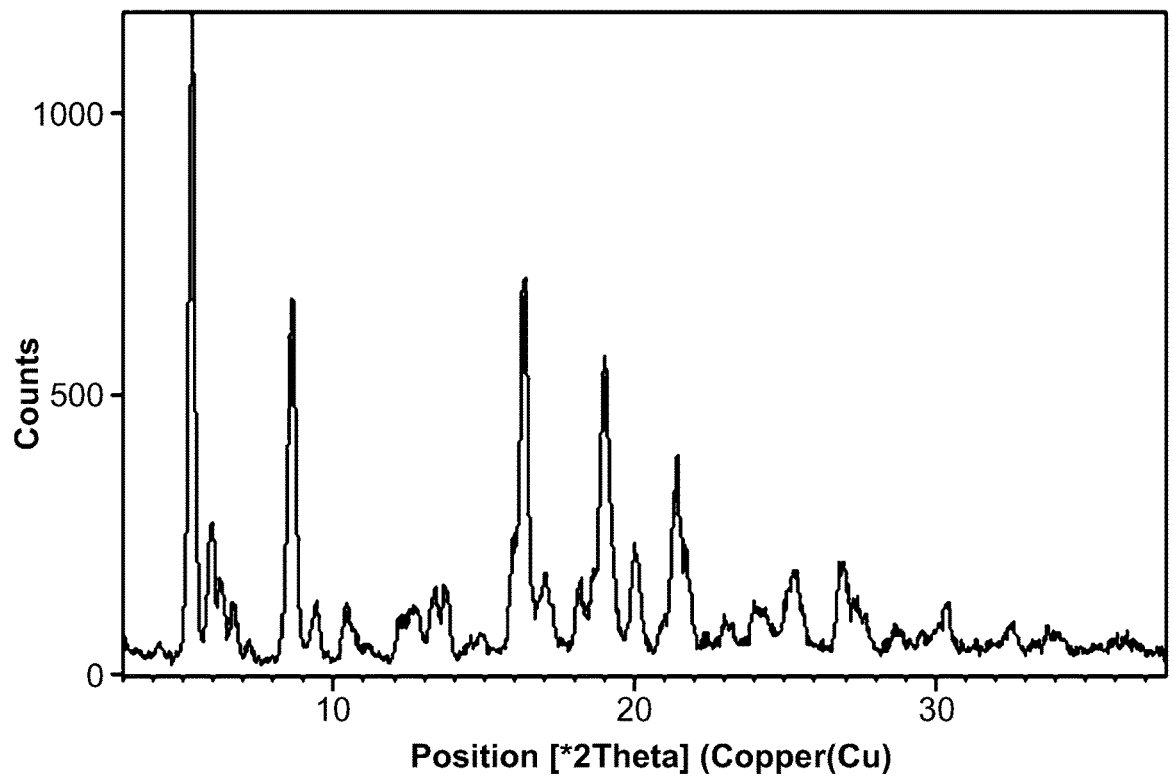
FIG. 7: Shows XRPD pattern of Form F, in the 2-theta scale range of 3 to 40.

In some embodiments, Form F is characterized by an XRPD spectrum substantially similar to that shown in FIG. 7.

In other embodiments, Form F is characterized by one or more peaks in the XRPD spectrum selected from: 5.3 (100.00% rel int), 8.6 (58.80%), and 16.4 (62.95%) °2θ.

In another embodiment, Form F is characterized by one or more peaks in the XRPD spectrum selected from: 5.3 (100.00% rel int), 8.6 (58.80%), 16.4 (62.95%), and 19.0 (48.51%) °2θ.

In one aspect, the solid form of Compound I is polymorph Form G.

In some embodiments, Form G is characterized by an XRPD spectrum substantially similar to that shown in FIG. 8.

In other embodiments, Form G is characterized by one or more peaks in the XRPD spectrum selected from: 10.7 (55.47% rel int) and 18.33 (100.00% %) °2θ.

In another embodiment, Form G is characterized by one or more peaks in the XRPD spectrum selected from: 10.7 (55.47% rel int), 13.9 (42.47%), 18.33 (100.00% %), and 21.6 (40.73%) °2θ.

In one aspect, the solid form of Compound I is polymorph Form H.

In some embodiments, Form H is characterized by an XRPD spectrum substantially similar to that shown in FIG. 9.

In other embodiments, Form H is characterized by one or more peaks in the XRPD spectrum selected from: 5.77 (89.22% rel int), 6.39 (100.00% %), 9.1 (84.17%), and 18.5 (67.04%) °2θ.

In another embodiment, Form H is characterized by one or more peaks in the XRPD spectrum selected from: 5.77 (89.22% rel int), 6.39 (100.00% %), 9.1 (84.17%), 18.5 (67.04%), and 18.83 (67.04%) °2θ.

Pharmaceutically Acceptable Salts of the Invention.

The phrase "pharmaceutically acceptable salt," as used herein, refers to pharmaceutically acceptable organic or inorganic salts of Compound I. The pharmaceutically acceptable salts of Compound I can be used in medicine. Salts that are not pharmaceutically acceptable may, however, be useful as intermediates in the preparation of other solid forms of Compound I.

A pharmaceutically acceptable salt involves the inclusion of another atom or molecule acting as the counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. In some instances, the counter ions may be the same. In other instances, they may be different for each charged atom. Hence, a pharmaceutically acceptable salt can have one or more charged atoms and/or one or more counter ions.

The preparation of the pharmaceutically acceptable salts herein described and other typical pharmaceutically acceptable salts is more fully described by Berg et al., "Pharmaceutical Salts," J. Pharm. Sci., 1977:66:1-19, incorporated here by reference in its entirety.

In one embodiment, a pharmaceutically acceptable salt of Compound I is the hydrochloric acid salt of Compound I.

The hydrochloric acid salt of Compound I can be prepared by suspending Compound I in its polymorph Form D, prepared as described above, in 1M HCl, mixing it with i-PrOH, stirring with temperature cycling between 20 and 40° C. at a heating rate of 40° C./h and a cooling rate of 5° C./h.

The hydrochloric acid salt of Compound I is characterized by a melting point of 256° C.

The hydrochloric acid salt of Compound I is characterized by an aqueous solubility of 0.5 mg/mL at pH 1.4. Aqueous solubility was determined at the pH of the saturated solution. The salt was shaken in water for 24 hours at 25° C. After filtration, the concentration was determined by HPLC to be 0.5 mg/mL at a pH of 1.4.

Figure 11:
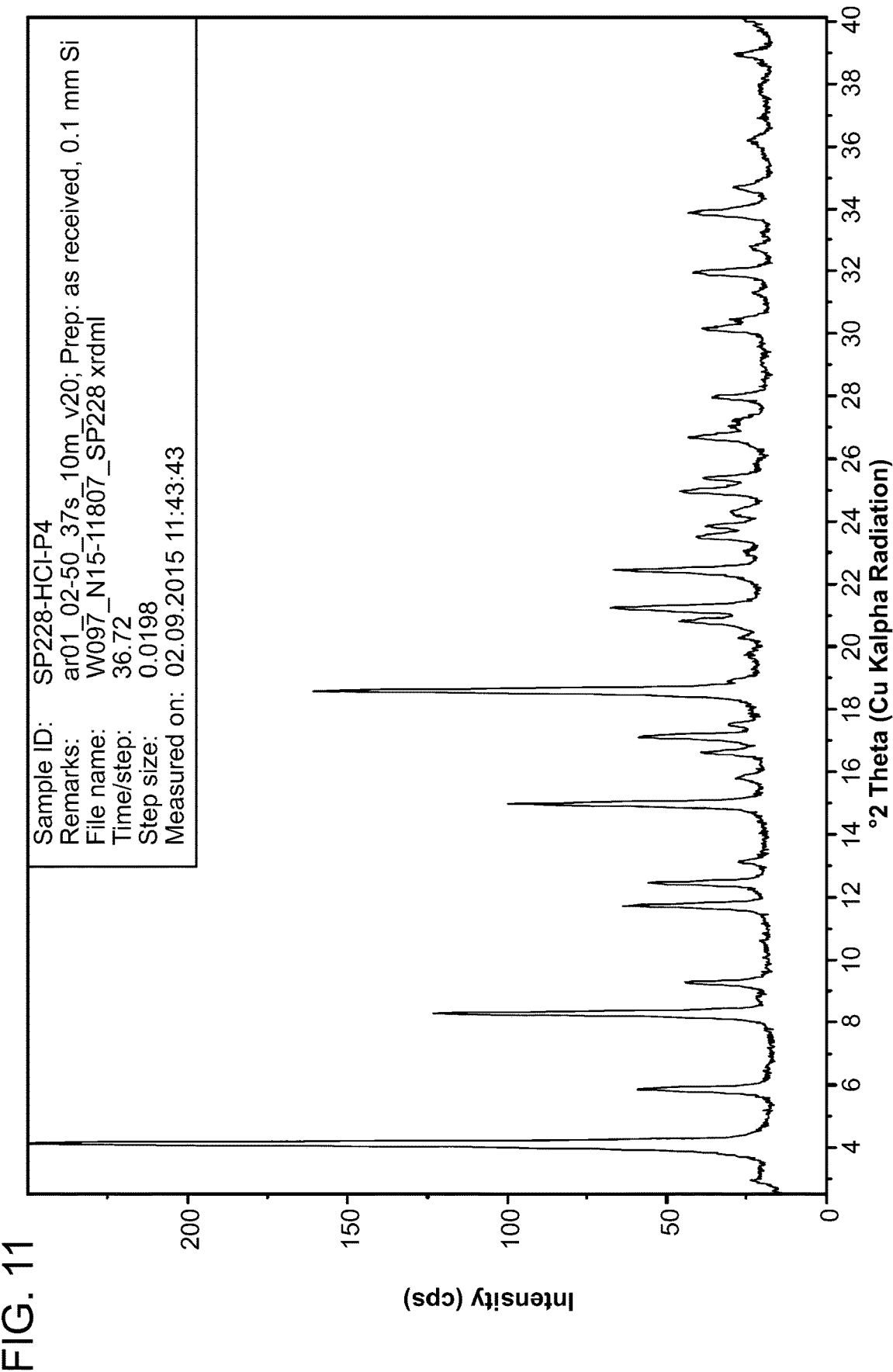
FIG. 11: Shows XRPD pattern of HCl salt of Compound I, in the 2-theta scale range of 0 to 40.

The hydrochloric acid salt of Compound I is characterized by an XRPD pattern substantially similar to that shown in FIG. 11.

Pharmaceutical Compositions and Methods of Administration.

The crystalline solid forms herein disclosed, may be formulated as pharmaceutical compositions or "formulations".

A typical formulation is prepared by mixing a crystalline solid form of Compound I and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a polymorph or pharmaceutically acceptable salt of Compound I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g., enteric or slow release) preservatives, antioxidants, opaquing agents, glidants, processing aids, colorants, sweeteners, perfuming agents, flavoring agents and other known additives to provide an elegant presentation of the drug or aid in the manufacturing of the pharmaceutical product (i.e., medicament).

The formulations may be prepared using conventional dissolution and mixing procedures. For example, the bulk drug substance (i.e., a polymorph or a pharmaceutically acceptable salt of Compound I) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the formulation described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

A polymorph or pharmaceutically acceptable salt of Compound I is typically formulated into pharmaceutical dosage forms to provide an easily controllable dosage of the drug and to enable patient compliance with the prescribed regimen. Pharmaceutical formulations of a polymorph or pharmaceutically acceptable salt of Compound I, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of a polymorph or pharmaceutically acceptable salt of Compound I, will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methyl methacrylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, $21^{st}$ Edition, University of the Sciences in Philadelphia, Eds., 2005 (hereafter "Remington's").

The terms "administer", "administering" or "administration" in reference to a solid form, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g., orally (e.g., using capsules, powders, solutions, suspensions, tablets, sublingual tablets and the like), by inhalation (e.g., with an aerosol, gas, inhaler, nebulizer or the like), to the ear (e.g., using ear drops), topically (e.g., using creams, gels, liniments, lotions, ointments, pastes, transdermal patches, etc.), ophthalmically (e.g., with eye drops, ophthalmic gels, ophthalmic ointments), rectally (e.g., using enemas or suppositories), nasally, buccally, vaginally (e.g., using douches, intrauterine devices, vaginal suppositories, vaginal rings or tablets, etc.), via an implanted reservoir or the like, or parenterally, depending on the severity and type of the disease being treated.

The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compound(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a polymorph of Compound I or a pharmaceutically acceptable salt of Compound I that are suitable for oral administration may be prepared as discrete units such as tablets, pills, troches, lozenges, aqueous or oil suspensions, dispersible powders or granules, emulsions, hard or soft capsules, e.g., gelatin capsules, syrups or elixirs. Formulations of a compound intended for oral use may be prepared according to any method known to the art for the manufacture of pharmaceutical compositions.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

The active solid forms can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g., for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol or PEG400. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a polymorph of Compound I or a pharmaceutically acceptable salt thereof, in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a polymorph of Compound I or a pharmaceutically acceptable salt of Compound I contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the solid forms described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the solid forms of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a polymorph of Compound I or a pharmaceutically acceptable salt of Compound I, may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a polymorph of Compound I or a pharmaceutically acceptable salt of Compound I, include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a polymorph of Compound I or a pharmaceutically acceptable salt of Compound I may be formulated in a veterinary composition comprising a veterinary carrier. Veterinary carriers are materials useful for the purpose of administering the composition and may be solid, liquid or gaseous materials which are otherwise inert or accepted in the veterinary art and are compatible with the active ingredient. These veterinary compositions may be administered parenterally, orally or by any other desired route.

Therapeutic Methods

In another aspect, the invention relates to the treatment of certain disorders by using the crystalline solid forms of Compound I herein disclosed, either alone or in combination, or pharmaceutical compositions comprising them, in a patient in need thereof.

The present disclosure relates to crystalline solid forms of Compound I, and pharmaceutical formulations thereof and their use, alone or in combination with one or more additional agents, for treating and/or preventing various diseases, wherein an increase in the concentration of NO or an increase in the concentration of cGMP is desirable.

Increased production of NO or increased concentration of cGMP in a tissue leads to vasodilation, inhibition of platelet aggregation and adhesion, anti-hypertensive effects, anti-remodeling effects, anti-fibrotic, anti-apoptotic effects, anti-inflammatory effects and neuronal signal transmission effects, among other effects.

In other embodiments, the crystalline solid forms of Compound I here disclosed are useful in the prevention and/or treatment of diseases and disorders characterized by undesirable reduced bioavailability of and/or sensitivity to NO in a biological system (e.g., in the human body), such as those associated with conditions of oxidative stress or nitrosative stress.

The term "cardiovascular disease" (or "cardiovascular disorder") as used herein, refers to a disease based on the abnormal symptoms of circulatory organs such as the heart, blood vessels (arteries, capillaries, and veins) or both. The term also includes any disease that affects the cardiovascular system in general, including cardiac disease, vascular diseases of the brain, vascular diseases of the kidney, liver and associated organs, or lung, and peripheral arterial disease, among others.

A "sGC-related cardiovascular disease" is one for which the NO/sGC/cGMP system is known or suspected to be involved and is a cardiovascular disease that can be treated or prevented by sGC activation/stimulation, by activation of a NO synthase, or by addition of NO or an NO-donor or an NO precursor such as L-Arginine or L-citruline, or by inhibition of a PDE (phosphodiesterase) enzyme responsible for the breakdown of cGMP, or a combination of the any of the above methods.

The term "vasodilation" as used herein, refers to the widening of blood vessels. It results from relaxation of smooth muscle cells within the vessel walls, in particular in the large veins, large arteries, and smaller arterioles. In essence, the process is the opposite of "vasoconstriction", which is the narrowing of blood vessels. When blood vessels dilate, the flow of blood is increased due to a decrease in vascular resistance. Therefore, dilation of arterial blood vessels (mainly the arterioles) decreases blood pressure. The response may be intrinsic (due to local processes in the surrounding tissue) or extrinsic (due to hormones or the nervous system). In addition, the response may be localized to a specific organ (depending on the metabolic needs of a particular tissue, as during strenuous exercise), or it may be systemic (seen throughout the entire systemic circulation).

The term "vasoconstriction" as used herein refers to the narrowing of a blood vessel due to muscle contraction. Vasoconstriction is one mechanism by which the body regulates and maintains mean arterial pressure (MAP). Generalized vasoconstriction usually results in an increase in systemic blood pressure, but it may also occur in specific tissues, causing a localized reduction in blood flow.

As used herein, the term "bronchoconstriction" is used to define the constriction of the airways in the lungs due to the tightening of surrounding smooth muscle, with consequent coughing, wheezing, and shortness of breath. The condition has a number of causes, the most common being asthma. Exercise and allergies can bring on the symptoms in an otherwise asymptomatic individual. Other conditions such as chronic obstructive pulmonary disease (COPD) can also present with bronchoconstriction.

Throughout this disclosure, the terms "hypertension", "arterial hypertension" or "high blood pressure (HBP)" are used interchangeably and refer to an extremely common and highly preventable chronic condition in which blood pressure (BP) in the arteries is higher than normal or desired. If not properly controlled, it represents a significant risk factor for several serious cardiovascular and renal conditions. Hypertension may be a primary disease, called "essential hypertension" or "idiopathic hypertension", or it may be caused by or related to other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension. Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

The term "coronary artery disease" refers to a condition in which the blood supply to the heart muscle is partially or completely blocked (ischemia of the heart muscle or myocardium). This reduced blood supply to the myocardium may result in a number of "acute myocardial syndromes": chest pain ("angina", also called "angina pectoris", stable or unstable) and different types of heart attacks ("myocardial infarction" or MI). One common cause of coronary artery disease is "atherosclerosis" which refers to hardening of the arteries, due to fatty deposits in the artery walls which then may progress through formation of atherosclerotic plaques, to narrowing and eventually blockage of blood flow to the in the artery. This process of atherosclerosis may affect other arteries as well, not just those of the heart. A blood clot is the most common cause of the blockage of the artery, as usually the artery is already partially blocked due to atherosclerotic plaque (atheroma); the atheroma may rupture or tear, leading to the formation of a clot. Occasionally, coronary artery disease is caused by spasm of a coronary artery, which can occur spontaneously or as a result of the use of certain drugs (e.g., cocaine, nicotine). Rarely, the cause of coronary artery disease is a birth defect, a viral infection (e.g., Kawasaki disease), systemic lupus erythematosus (lupus), inflammation of the arteries (arteritis), a blood clot that travelled from a heart chamber into one of the coronary arteries or physical damage (e.g., from injury or radiation therapy).

"Unstable angina", as used herein, refers to a change in the pattern of angina symptoms including prolonged or worsening angina and new onset of severe symptoms.

MI (myocardial infarction) can be classified into two types: "Non-ST-segment elevation" MI and "ST-segment elevation" MI. The complications of acute coronary syndromes depend on how much, how long, and where the coronary artery is blocked. If the blockage affects a large amount of heart muscle, the heart will not pump effectively. If the blockage shuts off blood flow to the electrical system of the heart, the heart rhythm may be affected. When a heart attack occurs, part of the myocardium dies. Dead tissue and the scar tissue that replaces it, does not contract. The scar tissue sometimes even expands or bulges when the rest of the heart tries to contract. Consequently, there is less muscle to pump blood. If enough muscle dies, the heart's pumping ability may be so reduced that the heart cannot meet the body's demands for oxygen and blood. Heart failure, low blood pressure or both then develop. If more than half of the myocardium is damaged or dies, the heart generally cannot function and severe disability or death is likely.

As used herein "Heart Failure" (HF) is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neuro-hormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness; edema of the feet, ankles and legs; rapid weight gain; or chronic cough, including that producing mucus or blood. Depending on its clinical presentation, heart failure is classified as de novo, transient, acute, post-acute or chronic. Acute heart failure, i.e., the rapid or gradual onset of symptoms requiring urgent therapy, may develop de novo or as a result of chronic heart failure becoming decompensated. The term "Heart failure" is often used to mean "chronic heart failure". The terms "congestive heart failure (CHF)" or "congestive cardiac failure (CCF)" are often used interchangeably with chronic heart failure. Common causes of heart failure include coronary artery disease including a previous myocardial infarction (heart attack), high blood pressure, atrial fibrillation, valvular heart disease, and cardiomyopathy. These cause heart failure, by changing either the structure or the functioning of the heart.

There are two main types of heart failure: "heart failure due to reduced ejection fraction (HFREF)", also known as "heart failure due to left ventricular systolic dysfunction" or "systolic heart failure", and "heart failure with preserved ejection fraction (HFPEF)", also known as "diastolic heart failure" or "heart failure with normal ejection fraction (HFNEF)". Ejection fraction is the proportion of blood in the heart pumped out of the heart during a single contraction. It is a percentage with normal being between 50 and 75%.

The term "acute" (as in "acute HF") is used to mean rapid onset, and "chronic" refers to long duration. Chronic heart failure is a long term situation, usually with stable treated symptomatology. "Acute decompensated" heart failure is worsening or decompensated heart failure, referring to episodes in which a person can be characterized as having a change in heart failure signs and symptoms resulting in a need for urgent therapy or hospitalization. Heart failure may also occur in situations of high output (then it is termed "high output cardiac failure") where the ventricular systolic function is normal but the heart cannot deal with an important augmentation of blood volume.

In cardiovascular physiology, the term "Ejection Fraction (EF)" is defined as the fraction of blood in the left and right ventricles that is pumped out with each heartbeat or cardiac cycle. In finite mathematics allowed by medical imaging, EF is applied to both the right ventricle, which ejects blood via the pulmonary valve into the pulmonary circulation, or the left ventricle, which ejects blood via the aortic valve into the cerebral and systemic circulation.

The term "heart failure with preserved ejection fraction (HFPEF)" is commonly understood to refer to a manifestation of signs and symptoms of heart failure with an ejection fraction greater than 55%. It is characterized by a decrease in left ventricular compliance, leading to increased pressure in the left ventricle. Increased left atrial size is often seen with HFPEF as a result of the poor left ventricular function. There is an increased risk for congestive heart failure, atrial fibrillation, and pulmonary hypertension. Risk factors are hypertension, hyperlipidemia, diabetes, smoking, and obstructive sleep apnea. In this type of heart failure, the heart muscle contracts well but the ventricle does not fill with blood well in the relaxation phase.

The term "heart failure with reduced ejection fraction (HFREF)" refers to heart failure in which the ejection fraction is less than 40%.

Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, non-voluntary loss of at least 6% of body weight over a period of six months.

The term "arrhythmias", as used herein, refers to abnormal heart rhythms that occur in more than 90% of people who have had a heart attack. Sometimes the problem is with the part of the heart that triggers the heartbeat and the heart rate may be too slow, other times the problems may cause the heart to beat too rapidly or irregularly. Sometimes the signal to beat is not conducted from one part of the heart to the other and the heartbeat may slow or stop. In addition, areas of the myocardium that have not died but have poor blood flow may be irritable. This causes heart rhythm problems such as ventricular tachycardia or ventricular fibrillation. This may lead to cardiac arrest if the heart stops pumping entirely.

The "pericardium" is the sack or membrane that surrounds the heart. "Pericarditis" or inflammation of this membrane may develop as a result of a heart attack and may result in fever, pericardial effusion, inflammation of the membranes covering the lungs (pleura), pleural effusion, and joint pain. Other complications after a heart attack may include malfunction of the mitral valve, rupture of the heart muscle, a bulge in the wall of the ventricle (ventricular aneurysm), blood clots, and low blood pressure.

The term "cardiomyopathy" refers to the progressive impairment of the structure and function of the muscular walls of the heart chambers. The main types of cardiomyopathies are dilated, hypertrophic and restrictive. Cardiomyopathies often cause symptoms of heart failure, and they may also cause chest pain, fainting and sudden death.

The terms "mitral valve regurgitation", "mitral regurgitation", "mitral insufficiency" or "mitral incompetence" refer to a situation in which the mitral valve of the heart doesn't close tightly, allowing blood to flow backward in the heart. As a result, blood can't move through the heart or to the rest of the body as efficiently, resulting in fatigue or shortness of breath.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertriglyceridemia" involves elevated levels of triglycerides). "Hyperlipoproteinemia" refers to elevated levels of lipoproteins (usually LDL unless otherwise specified).

The term "steatosis" refers to the abnormal retention of lipids within a cell. It usually reflects an impairment of the normal processes of synthesis and elimination of triglycerides. Excess fat accumulates in vesicles that displace the cytoplasm of the cell. In severe cases the cell may burst. Usually steatosis is observed in the liver as it is the organ mostly associated with fat metabolism. It can also be observed in the heart, kidneys and muscle tissue.

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or the brain. PVD can result from atherosclerosis, inflammatory processes leading to stenosis, an embolism, thrombus formation or other types of occlusions. It causes either acute or chronic "ischemia (lack of blood supply)". Often PVD is a term used to refer to atherosclerotic blockages found in the lower extremity. PVD also includes a subset of diseases classified as microvascular diseases resulting from episodic narrowing of the arteries (e.g., "Raynaud's phenomenon"), or widening thereof (erythromelalgia), i.e., vascular spasms. Peripheral arterial diseases include occlusive thrombotic vasculitis, peripheral arterial occlusive disease, Raynaud's disease, and Raynaud's syndrome. Common symptoms are cold leg or feet, intermittent claudication, lower limb pain and critical limb ischemia (lower limb ulcers and necrosis). Diagnosis and treatment guidelines for peripheral arterial disease can be found in Eur. J. Vasco Endovasc. Surg, 2007, 33(1), Sl.

The term "stenosis" as used herein refers to an abnormal narrowing in a blood vessel or other tubular organ or structure. It is also sometimes called a "stricture" (as in urethral stricture). The term "coarctation" is a synonym, but is commonly used only in the context of aortic coarctation. The term "restenosis" refers to the recurrence of stenosis after a procedure.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin. The material that forms the embolism can have a number of different origins: if the material is blood the "embolus" is termed a "thrombus"; the solid material could also comprise fat, bacterial remains, infected tissue, etc.

"Ischemia" is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism). If the "ischemia" takes place in the heart muscle (or "myocardium") the ischemia is termed myocardial ischemia. Other types of ischemia are for instance cerebral ischemia, critical limb ischemia and the like.

"Reperfusion" occurs when blood supply returns to the tissue after a period of ischemia. Upon restoration of circulation to the tissue, inflammatory and oxidative stress processes may develop. One example of this chain of events is ischemia-reperfusion associated with organ transplants.

"Reperfusion injury" is the tissue damage caused when blood supply returns to the tissue after a period of ischemia and inflammation and oxidative damage ensue rather than restoration of normal function. Reperfusion of ischemic issues is often associated with microvascular injury, particularly due to the increased permeability of capillaries and arterioles that lead to an increase in diffusion and fluid filtration across the tissues. The activated endothelial cells produce more reactive oxygen species but less NO following reperfusion, and the imbalance results in an inflammatory response. White blood cells, carried to the area by the newly returned blood flow, release a host of inflammatory factors and free radicals in response to tissue damage. The restored blood flow brings with it oxygen that damages cellular proteins, DNA and plasma membranes. This process of ischemia-reperfusion is also thought to be responsible for formation and failure to heal of chronic wounds, (e.g., pressure sores or diabetic ulcers).

The term "angiopathy" as used herein is the generic term for a disease of the blood vessels (arteries, veins, and capillaries). The most common and most prevalent angiopathy is "diabetic angiopathy", a common complication of chronic diabetes. Another common type of angiopathy is "cerebral amyloid angiopathy" (CAA), also known as congophilic angiopathy, wherein amyloid deposits form in the walls of the blood vessels of the central nervous system. The term congophilic is used because the presence of the abnormal aggregations of amyloid can be demonstrated by microscopic examination of brain tissue after application of a special stain called Congo red. The amyloid material is only found in the brain and as such the disease is not related to other forms of amyloidosis.

A "stroke", or cerebrovascular accident (CVA), is the rapid loss of brain function(s) due to disturbance in the blood supply to the brain. This can be due to "ischemia" (lack of blood flow with resultant insufficient oxygen and glucose supply to the tissue) caused by blockage (thrombosis, arterial embolism, fat accumulation or a spasm), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Vascular dementia" is the 2nd most common cause of dementia among the elderly. It is more common among men and usually begins after age 70. It occurs more often in people who have vascular risk factors (e.g., hypertension, diabetes mellitus, hyperlipidemia, smoking) and in those who have had several strokes. Many people have both vascular dementia and Alzheimer disease. Vascular dementia typically occurs when multiple small cerebral infarcts (or sometimes hemorrhages) cause enough neuronal or axonal loss to impair brain function. Vascular dementias include the following types: multiple lacunar infarction (wherein small blood vessels are affected and infarcts occur deep within hemispheric white and gray matter); multi-infarct dementia (wherein medium-sized blood vessels are affected); strategic single-infarct dementia (wherein a single infarct occurs in a crucial area of the brain such as the angular gyms or the thalamus; Binswanger dementia or subcortical arteriosclerotic encephalopathy (wherein small-vessel dementia is associated with severe, poorly controlled hypertension and systemic vascular disease and which causes diffuse and irregular loss of axons and myelin with widespread gliosis, tissue death due to an infarction, or loss of blood supply to the white matter of the brain).

The term "glioma" refers to a type of tumor that starts in the brain or spine. It is called a glioma because it arises from glial cells. The most common site of gliomas is the brain. Gliomas make up about 30% of all brain and central nervous system tumors and 80% of all malignant brain tumors.

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

In one embodiment, polymorphs and pharmaceutically acceptable salts of Compound I herein described are therefore useful in the prevention and/or treatment of the following types of cardiac, pulmonary, peripheral, hepatic, kidney, or cerebral vascular/endothelial disorders, conditions and diseases related to circulation:

disorders related to high blood pressure and decreased coronary blood flow; increased acute and chronic coronary blood pressure; arterial hypertension; vascular disorder resulting from cardiac and renal complications; vascular disorders resulting from heart disease, stroke, cerebral ischemia or renal failure; resistant hypertension; diabetic hypertension; essential hypertension; secondary hypertension; gestational hypertension; pre-eclampsia; portal hypertension; myocardial infarction;

heart failure, HFPEF, HFREF; acute and chronic HF; more specific forms of HF: acute decompensated HF, right ventricular failure, left ventricular failure, total HF, ischemic cardiomyopathy, dilated cardiomyopathy, congenital heart defects, HF with valvular defects, mitral valve stenosis, mitral valve insufficiency, aortic valve stenosis, aortic valve insufficiency, tricuspid stenosis, tricuspic insufficiency, pulmonary valve stenosis, pulmonary valve insufficiency, combined valvular defects; diabetic heart failure; alcoholic cardiomyopathy or storage cardiomyopathies; diastolic HF, systolic HF; acute phases of an existing chronic HF (worsening HF); diastolic or systolic dysfunction; coronary insufficiency; arrhythmias; reduction of ventricular preload; cardiac hypertrophy; heart failure/cardiorenal syndrome; portal hypertension; endothelial dysfunction or injury; disturbances of atrial and ventricular rhythm and conduction disturbances: atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia; Wolff-Parkinson-White syndrome or acute coronary syndrome; Boxer cardiomyopathy; premature ventricular contraction; cardiomyopathy; cancer-induced cardiomyopathy; chemotherapy-induced cardiotoxicity;

thromboembolic disorders and ischemias; myocardial ischemia; infarction; myocardial infarction; heart attack; myocardial insufficiency; endothelial dysfunction; stroke; transient ischemic attacks (TIAs); obstructive thromboanginitis; stable or unstable angina pectoris; coronary spasms or spasms of the peripheral arteries; variant angina; Prinzmetal's angina; cardiac hypertrophy; preeclampsia; thrombogenic disorders; ischemia-reperfusion damage; ischemia-reperfusion associated with organ transplant; ischemia-reperfusion associated with lung transplant, pulmonary transplant, cardiac transplant, venous graft failure; conserving blood substituents in trauma patients;

peripheral vascular disease; peripheral arterial disease; peripheral occlusive arterial disease; hypertonia; Raynaud's syndrome or phenomenon (primary and secondary); Raynaud's disease; critical limb ischemia; peripheral embolism; intermittent claudication; vaso-occlusive crisis; muscular dystrophy, Duchenne muscular dystrophy, Becker muscular dystrophy; microcirculation abnormalities; control of vascular leakage or permeability; lumbar spinal canal stenosis; occlusive thrombotic vasculitis; thrombotic vasculitis; peripheral perfusion disturbances; arterial and venous thrombosis; microalbuminuria; peripheral and autonomic neuropathies; diabetic neuropathic pain; diabetic microangiopathies; hepatic vaso-occlusive disorder; vaso-occlusive crisis in sickle cell disease; hypertensive crisis;

edema; renal edema due to heart failure;

Alzheimer's disease; Parkinson's disease; vascular dementias; vascular cognitive impairment; cerebral vasospasm; congenital myasthenic syndrome; subarachnoid hemorrhage; traumatic brain injury; improving perception, capacity for concentration, capacity for learning or memory performance after cognitive disturbances such as those occurring in mild cognitive impairment, age-related learning and memory disturbances, age-related memory loss, vascular dementia, head injury, stroke, post-stroke dementia, post-traumatic head injury, general disturbances of concentration and disturbances of concentration in children with learning and memory problems; Lewy body dementia; dementia with frontal lobe degeneration including Pick's syndrome; progressive nuclear palsy; dementia with corticobasal degeneration; Amyotrophic Lateral Sclerosis (ALS); Huntington's disease; demyelination; Multiple Sclerosis; thalamic degeneration; Creutzfeldt-Jakob dementia; HIV-dementia; schizophrenia with dementia or Korsakoff psychosis; Multiple System Atrophy and other forms of Parkinsonism Plus; movement disorders; neuroprotection; anxiety, tension and depression or post-traumatic stress disorder (PTSD); bipolar disorder; schizophrenia; CNS-related sexual dysfunction and sleep disturbances; pathological eating disorders and use of luxury foods and addictive drugs; controlling cerebral perfusion; migraines; prophylaxis and control of consequences of cerebral infarction (apoplexia cerebri); prophylaxis and control of consequences of stroke, cerebral ischemias and head injury; neuropathies associated to a CNS disease; neuropathic pain associated with MS; chemotherapy induced neuropathic pain; neuropathic pain associated with shingles; neuropathic pain associated with spine surgery;

shock; cardiogenic shock; sepsis; septic shock; anaphylactic shock; aneurysm; control of leukocyte activation; inhibition or modulation of platelet aggregation; multiple organ dysfunction syndrome (MODS); multiple organ failure (MOF);

pulmonary/respiratory conditions: pulmonary hypertension (PH); pulmonary arterial hypertension (PAH), and associated pulmonary vascular remodeling; vascular remodeling in the form of localized thrombosis and right heart hypertrophy; pulmonary hypertonia; primary pulmonary hypertension; secondary pulmonary hypertension; familial pulmonary hypertension; sporadic pulmonary hypertension; pre-capillary pulmonary hypertension; idiopathic pulmonary hypertension; other forms of PH; PH associated with left ventricular disease, HIV, SCD, thromboembolism (CTEPH), sarcoidosis, COPD, pulmonary fibrosis, acute respiratory distress syndrome (ARDS), acute lung injury, alpha-1-antitrypsin deficiency (AATD), pulmonary emphysema, smoking-induced emphysema and cystic fibrosis (CF); thrombotic pulmonary arteriopathy; plexogenic pulmonary arteriopathy; cystic fibrosis; bronchoconstriction or pulmonary bronchoconstriction; acute respiratory syndrome; lung fibrosis, lung transplant; asthmatic diseases;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary veno-occlusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism; pulmonary embolism due to tumor, parasites or foreign material; connective tissue disease, lupus, lupus nephritis, schistosomiasis, sarcoidosis, chronic obstructive pulmonary disease, asthma, emphysema, chronic bronchitis, pulmonary capillary hemangiomatosis, histiocytosis X, lymphangiomatosis, compressed pulmonary vessels; compressed pulmonary vessels due to adenopathy, tumor or fibrosing mediastinitis;

arterosclerotic diseases or conditions: atherosclerosis; atherosclerosis associated with endothelial injury, platelet and monocyte adhesion and aggregation, smooth muscle proliferation or migration; restenosis; restenosis developed after thrombolysis therapies, percutaneous transluminal angioplasties (PTAs), transluminal coronary angioplasties (PTCAs), heart transplant, bypass operations or inflammatory processes;

micro and macrovascular damage (vasculitis); increased levels of fibrinogen and low density DLD; increased concentration of plasminogen activator inhibitor 1 (PA-1);

metabolic syndrome; metabolic diseases or diseases associated with metabolic syndrome: obesity; excessive subcutaneous fat; excessive adiposity; diabetes; high blood pressure; lipid related disorders, hyperlipidemias, dyslipidemia, hypercholesterolemias, decreased high-density lipoprotein cholesterol (HDL-cholesterol), moderately elevated low-density lipoprotein cholesterol (LDL-cholesterol) levels, hypertriglyceridemias, hyperglyceridemia, hypolipoproteinanemias, sitosterolemia, fatty liver disease, alcoholic fatty liver disease (AFLD), non-alcoholic fatty liver disease (NAFLD), hepatitis; preeclampsia; polycystic kidney disease progression; liver steatosis or abnormal lipid accumulation in the liver, non-alcoholic steatohepatitis (NASH); steatosis of the heart, kidneys or muscle; alphabetalipoproteinemia; sitosterolemia; xanthomatosis; Tangier disease; hyperammonemia and related diseases; hepatic encephalopathies; other toxic encephalopathies; Reye syndrome;

sexual, gynecological and urological disorders of conditions: erectile dysfunction; impotence; premature ejaculation; female sexual dysfunction; female sexual arousal dysfunction; hypoactive sexual arousal disorder; vaginal atrophy; dyspaneuria; atrophic vaginitis; benign prostatic hyperplasia (BPH), prostatic hypertrophy, prostatic enlargement; bladder outlet obstruction; bladder pain syndrome (BPS); interstitial cystitis (IC); overactive bladder; neurogenic bladder and incontinence; diabetic nephropathy; primary and secondary dysmenorrhea; lower urinary tract syndromes (LUTS); endometriosis; pelvic pains; benign and malignant diseases of the organs of the male and female urogenital system;

chronic kidney disease; acute and chronic renal insufficiency; acute and chronic renal failure; lupus nephritis; underlying or related kidney diseases: hypoperfusion, intradialytic hypotension, obstructive uropathy, glomerulopathies, glomerulonephritis, acute glomerulonephritis, glomerulosclerosis, tubulointerstitial diseases, nephropathic diseases, primary and congenital kidney diseases, nephritis; diseases characterized by abnormally reduced creatinine and or water excretion; diseases characterized by abnormally increased blood concentrations of urea, nitrogen, potassium and/or creatinine; diseases characterized by altered activity of renal enzymes, diseases characterized by altered activity of glutamyl synthetase; diseases characterized by altered urine osmolarity or urine volume; diseases characterized by increased microalbuminuria, diseases characterized by macroalbuminuria; diseases characterized by lesions of glomeruli and arterioles, tubular dilatation, hyperphosphatemia and/or need for dialysis; sequelae of renal insufficiency; renal-insufficiency related pulmonary enema; renal-insufficiency related to HF; renal insufficiency related to uremia or anemia; electrolyte disturbances (herkalemia, hyponatremia); disturbances of bone and carbohydrate metabolism; acute kidney injury;

ocular diseases or disorders such as glaucoma, retinopathy and diabetic retinopathy.

The term "Inflammation" refers to the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even though the two are often correlated (the former often being a result of the latter). Inflammation can also occur in the absence of infection, although such types of inflammation are usually maladaptive (such as in atherosclerosis). Inflammation is a stereotyped response, and therefore it is considered as a mechanism of innate immunity, as compared to adaptive immunity, which is specific for each pathogen. Progressive destruction of tissue in the absence of inflammation would compromise the survival of the organism. On the other hand, chronic inflammation might lead to a host of diseases, such as hay fever, periodontitis, atherosclerosis, rheumatoid arthritis, and even cancer (e.g., gallbladder carcinoma). It is for that reason that inflammation is normally closely regulated by the body. Inflammation can be classified as either acute or chronic. "Acute inflammation" is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as "chronic inflammation", leads to a progressive shift in the type of cells present at the site of inflammation and is characterized by simultaneous destruction and healing of the tissue from the inflammatory process.

In another embodiment, polymorphs and pharmaceutically acceptable salts of Compound I herein described, are therefore useful in the prevention and/or treatment of the following types of cardiac, pulmonary, peripheral, hepatic, kidney, digestive or Central Nervous System disorders, conditions and diseases which may involve inflammation or an inflammatory process:

heart muscle inflammation (myocarditis); chronic myocarditis; acute myocarditis; viral myocarditis;
vasculitis; pancreatitis; peritonitis; rheumatoid diseases;
inflammatory disease of the kidney; immunological kidney diseases: kidney transplant rejection, immune complex-induced kidney disease, nephropathy induced by toxins, contrast medium-induced nephropathy; diabetic and non-diabetic nephropathy, pyelonephritis, renal cysts, nephrosclerosis, hypertensive nephrosclerosis and nephrotic syndrome;
chronic interstitial inflammations. inflammatory bowel diseases (IBD), Crohn's, Ulcerative Colitis (UC);
inflammatory skin diseases;
inflammatory diseases of the eye, blepharitis, dry eye syndrome, and Sjögren's Syndrome; eye fibrosis.

The term "wound healing" refers to the intricate process where the skin (or another organ or tissue) repairs itself after injury. For instance, in normal skin, the epidermis (outermost layer) and dermis (inner or deeper layer) exist in a steady-state equilibrium, forming a protective barrier against the external environment. Once the protective barrier is broken, the normal (physiologic) process of wound healing is immediately set in motion. The classic model of wound healing is divided into three or four sequential, yet overlapping, phases: (1) hemostasis (not considered a phase by some authors), (2) inflammation, (3) proliferation and (4) remodeling. Upon injury to the skin, a set of complex biochemical events takes place in a closely orchestrated cascade to repair the damage. Within the first few minutes after the injury, platelets adhere to the site of injury, become activated, and aggregate (join together), followed by activation of the coagulation cascade which forms a clot of aggregated platelets in a mesh of cross-linked fibrin protein. This clot stops active bleeding ("hemostasis"). During the inflammation phase, bacteria and cell debris are phagocytosed and removed from the wound by white blood cells. Platelet-derived growth factors (stored in the alpha granules of the platelets) are released into the wound that cause the migration and division of cells during the proliferative phase. The proliferation phase is characterized by angiogenesis, collagen deposition, granulation tissue formation, epithelialization, and wound contraction. In "angiogenesis", vascular endothelial cells form new blood vessels. In "fibroplasia" and granulation tissue formation, fibroblasts grow and form a new, provisional extracellular matrix (ECM) by excreting collagen and fibronectin. Concurrently, "re-epithelialization" of the epidermis occurs, in which epithelial cells proliferate and 'crawl' atop the wound bed, providing cover for the new tissue. During wound contraction, myofibroblasts decrease the size of the wound by gripping the wound edges and contracting using a mechanism that resembles that in smooth muscle cells. When the cells' roles are close to complete, unneeded cells undergo apoptosis. During maturation and remodeling, collagen is remodeled and realigned along tension lines, and cells that are no longer needed are removed by apoptosis. However, this process is not only complex but fragile, and is susceptible to interruption or failure leading to the formation of non-healing chronic wounds (one example includes diabetic wounds or ulcers, and, in particular, diabetic foot ulcers). Factors that contribute to non-healing chronic wounds are diabetes, venous or arterial disease, infection, and metabolic deficiencies of old age.

The terms "bone healing", or "fracture healing" refers to a proliferative physiological process in which the body facilitates the repair of a bone fracture. In the process of fracture healing, several phases of recovery facilitate the proliferation and protection of the areas surrounding fractures and dislocations. The length of the process depends on the extent of the injury, and usual margins of two to three weeks are given for the reparation of most upper bodily fractures; anywhere above four weeks given for lower bodily injury. The healing process is mainly determined by the "periosteum" (the connective tissue membrane covering the bone). The periosteum is one source of precursor cells which develop into "chondroblasts" and osteoblasts that are essential to the healing of bone. The bone marrow (when present), endosteum, small blood vessels, and fibroblasts are other sources of precursor cells.

In another embodiment, polymorphs and pharmaceutically acceptable salts of Compound I herein described, are therefore useful in the treatment of the following types of diseases, disorders or conditions in which stimulation of the processes of wound or bone healing would be desirable:

wound or ulcer healing in diabetics; microvascular perfusion improvement; microvascular perfusion improvement following injury or to counteract the inflammatory response in perioperative care; anal fissures; diabetic ulcers; diabetic foot ulcers); bone healing; osteoclastic bone resorption and remodeling; and new bone formation.

The term "connective tissue" (CT) refers to a kind of animal tissue that supports, connects, or separates different types of tissues and organs of the body. It is one of the four general classes of animal tissues, the others being epithelial, muscle, and nervous tissues. Connective tissue is found everywhere, including in the central nervous system. It is located in between other tissues. All CT has three main components—ground substances, fibers and cells—and all these components are immersed in the body fluids.

The term "connective tissue disorder or condition" refers to any condition that involves abnormalities in connective tissue in one or more parts of the body. Certain disorders are characterized by over-activity of the immune system with resulting inflammation and systemic damage to the tissues, usually with replacement of normal tissue (e.g., normal tissue of a certain organ) with connective tissue. Other disorders involve biochemical abnormalities or structural defects of the connective tissue itself. Some of these disorders are inherited, and some are of unknown etiology.

When connective tissue diseases are of autoimmune origin they are classified as "rheumatic disorders", "autoimmune rheumatic disorders" or "autoimmune collagen-vascular disorders".

In an "autoimmune disorder", antibodies or other cells produced by the body attack the body's own tissues. Many autoimmune disorders affect connective tissue in a variety of organs. In autoimmune disorders, inflammation and the immune response may result in connective tissue damage, around the joints and also in other tissues, including vital organs, such as the kidneys or organs of the gastrointestinal tract. The sac that surrounds the heart (pericardium), the membrane that covers the lungs (pleura), the mediastinum (an undelineated group of structures in the thorax, surrounded by loose connective tissue, containing the heart, the great vessels of the heart, the esophagus, the trachea, the phrenic nerve, the cardiac nerve, the thoracic duct, the thymus, and the lymph nodes of the central chest) and even the brain may be affected.

The term "fibrosis" as used herein refers to the accumulation of connective tissue or fibrous tissue (scar tissue, collagen) in a certain organ or part of the body. If fibrosis arises from a single cell line it is called a "fibroma". Fibrosis occurs as the body attempts to repair and replace damaged cells, and thus can be a reactive, benign or a pathological state. Physiological fibrosis is similar to the process of scarring. A pathological state develops when the tissue in question is repeatedly and continuously damaged. A single episode of injury, even if severe, does not usually cause fibrosis. If injury is repeated or continuous (for instance as it occurs in chronic hepatitis) the body attempts to repair the damage, but the attempts result instead in excessive accumulation of scar tissue. Scar tissue starts to replace regular tissue of the organ which performs certain functions that the scar tissue is not able to perform; it can also interfere with blood flow and limit blood supply to other cells. As a result, these other functional cells start to die and more scar tissue is formed. When this occurs in the liver, blood pressure in the vein that carries blood from the intestine to the liver (portal vein) increases, giving rise to the condition known as "portal hypertension".

The term "sclerosis" refers to the hardening or stiffening of tissue or a structure or organ that would normally be flexible, usually by replacement of normal organ specific tissue with connective tissue.

There are many types of fibroses or fibrotic diseases including but not limited to pulmonary fibrosis (idiopathic pulmonary fibrosis, cystic fibrosis), fibrosis of the liver (or "cirrhosis"), endomyocardial fibrosis, old myocardial infarction, atrial fibrosis, mediastinal fibrosis, myelofibrosis (affecting the bone marrow), retroperitoneal fibrosis, progressive massive fibrosis (affects the lungs), nephrogenic fibrosis (affecting the skin), Crohn's disease, arthrofibrosis, Peyronie's disease (affecting the penis), Dupuytren's contracture (affecting the hands and fingers), some forms of adhesive capsulitis (affecting the shoulders).

There are many types of scleroses or "sclerotic diseases" including but not limited to Amyotrophic Lateral Sclerosis (ALS); atherosclerosis; focal segmental glomerulosclerosis and nephrotic syndrome; hippocampal sclerosis (affecting the brain); lichen sclerosus (a disease that hardens connective tissue of the vagina and penis); liver sclerosis (cirrhosis); multiple sclerosis or focal sclerosis (diseases that affects coordination); osteosclerosis (a disease in which bone density is significantly reduced); otosclerosis (disease affecting the ears); tuberous sclerosis (rare genetic disease affecting multiple systems); primary sclerosing cholangitis (hardening of the bile duct); primary lateral sclerosis (progressive muscle weakness in the voluntary muscles); and keloids.

The term "scleroderma" or "systemic sclerosis" or "progressive systemic scleroderma" refers to a condition which involves scarring of the joints, skin and internal organs as well as blood vessel abnormalities. Systemic sclerosis can sometimes occur in limited forms, for examples sometimes affecting just the skin or mainly only certain parts of the skin or as CREST syndrome (wherein peripheral areas of the skin but not the trunk are involved). The usual initial symptom of systemic sclerosis is swelling, then thickening and tightening of the skin at the end of the fingers. "Raynaud's phenomenon", in which fingers suddenly and temporarily become very pale and tingle or become numb, painful or both, is common.

The term "polymyositis" refers to muscle inflammation. The term "dermatomyositis", refers to muscle inflammation that is accompanied by skin inflammation. The term "polychondritis" refers to cartilage inflammation.

The term "oesinophilic fasciitis" refers to a rare disorder in which oesinophilic immune cells are released and results in inflammation and hardening of the "fasciae" which is the layer of tough fibrous tissue beneath the skin, on top and between the muscles. The fasciae becomes painfully inflamed and swollen and gradually hardens in the arms and legs. As the skin of the arms and legs progressively hardens, they become difficult to move. Eventually they become stuck in unusual positions. Sometimes, if the arms are involved the person may develop carpal tunnel syndrome.

In another embodiment, specific diseases of disorders which may be treated and/or prevented by administering polymorphs or pharmaceutically acceptable salts, of Compound I herein described, include but are not limited to the following type of diseases involving inflammation, autoimmunity or fibrosis (i.e., fibrotic diseases):

urogenital system or kidney disorders: diabetic nephropathy; renal fibrosis and renal failure resulting from chronic kidney diseases or insufficiency; renal fibrosis and renal failure due to accumulation/deposition and tissue injury; renal sclerosis; progressive sclerosis; glomerulonephritis; focal segmental glomerulosclerosis; nephrotic syndrome; prostate hypertrophy; kidney fibrosis; interstitial renal fibrosis;

pulmonary system disorders: pulmonary fibrosis; idiopathic pulmonary fibrosis; cystic fibrosis; progressive massive fibrosis; progressive massive fibrosis that affects the lungs);

disorders affecting the heart: endomyocardial fibrosis; old myocardial infarction; atrial fibrosis; cardiac interstitial fibrosis; cardiac remodeling and fibrosis; cardiac hypertrophy;

disorders of the liver and related organs: liver sclerosis or cirrhosis; liver cirrhosis associated with chronic liver disease; hepatic fibrosis; hepatic stellate cell activation; NASH; hepatic fibrous collagen and total collagen accumulation; liver disease of necro-inflammatory and/or of immunological origin; primary biliary cirrhosis; primary sclerosing cholangitis; other cholestatic liver diseases: those associated with granulomatous liver diseases, liver malignancies, intrahepatic cholestasis of pregnancy, hepatitis, sepsis, drugs or toxins, graft-versus-host disease, post-liver transplantation, choledocholithiasis, bile duct tumors, pancreatic carcinoma, Mirizzi's syndrome, AIDS cholangiopathy or parasites; schistosomiasis; hepatocellular carcinoma;

digestive diseases or disorders: Crohn's disease; Ulcerative Colitis; sclerosis of the gastro-intestinal tract; achalasia;

diseases of the skin or the eyes: nephrogenic fibrosis; proliferative vitroretinopathy; diabetic retinopathy; eye fibrosis;

fibrotic topical or skin disorders or conditions; dermal fibrosis; scleroderma, skin fibrosis; morphea; hypertrophic scars; naevi; keloids; sarcoids; granulomas;

diseases affecting the nervous system: Amyotrophic Lateral Sclerosis (ALS); hippocampal sclerosis, multiple sclerosis (MS); focal sclerosis; primary lateral sclerosis;

diseases of the bones; osteosclerosis;

otosclerosis; other hearing diseases or disorders; hearing impairment, partial or total hearing loss; partial or total deafness; tinnitus; noise-induced hearing loss;

other diseases involving autoimmunity, inflammation or fibrosis: scleroderma; localized scleroderma or circumscribed scleroderma; mediastinal fibrosis; fibrosis mediastinitis; myelofibrosis; retroperitoneal fibrosis; arthrofibrosis; Peyronie's disease; Dupuytren's contracture; lichen sclerosus; some forms of adhesive capsulitis; atherosclerosis; tuberous sclerosis; systemic sclerosis; polymyositis; dermatomyositis; polychondritis; oesinophilic fasciitis; Systemic Lupus Erythematosus or lupus; bone marrow fibrosis, myelofibrosis or osteomyelofibrosis; sarcoidosis; uterine fibroids; endometriosis.

In another embodiment, specific diseases of disorders which may be treated and/or prevented by administering polymorphs or pharmaceutically acceptable salts of Compound I herein described, include but are not limited to: certain types of cancers; Sickle Cell Disease; Sickle Cell Anemia; cancer metastasis; osteoporosis; gastroparesis; functional dyspepsia; diabetic complications; alopecia or hair loss; diseases associated with endothelial dysfunction; neurologic disorders associated with decreased nitric oxide production; arginosuccinic aciduria; neuromuscular diseases: Duchenne muscular dystrophy (DMD), Becker muscular dystrophy (BMD), limb girdle muscular dystrophies, distal myopathies, type I and type II myotonic dystrophies, facio-scapulo-peroneal muscular dystrophy, autosomal and X-linked Emery-Dreifuss muscular dystrophy, oculopharyngeal muscular dystrophy, amyotrophic lateral sclerosis and spinal muscle atrophy (SMA).

In some embodiments, the invention relates to a method of treating a disease, health condition or disorder in a subject, comprising administering a therapeutically effective amount of a polymorph of or a pharmaceutically acceptable salt of Compound I herein described, to the subject in need of treatment, wherein the disease, health condition or disorder is selected from one of the diseases listed above.

In another embodiment, solid forms of the invention can be delivered in the form of implanted devices, such as stents. A stent is a mesh 'tube' inserted into a natural passage/conduit in the body to prevent or counteract a disease-induced, localized flow constriction. The term may also refer to a tube used to temporarily hold such a natural conduit open to allow access for surgery.

A drug-eluting stent (DES) is a peripheral or coronary stent (a scaffold) placed into narrowed, diseased peripheral or coronary arteries that slowly releases a drug to block cell proliferation, usually smooth muscle cell proliferation. This prevents fibrosis that, together with clots (thrombus), could otherwise block the stented artery, a process called restenosis. The stent is usually placed within the peripheral or coronary artery by an Interventional Cardiologist or Interventional Radiologist during an angioplasty procedure. Drugs commonly used in DES in order to block cell proliferation include paclitaxel or rapamycin analogues.

In some embodiments of the invention, a polymorph or pharmaceutically acceptable salt of Compound I of the invention, or a pharmaceutical composition thereof, can be delivered by means of a drug-eluting stent coated with the solid form or pharmaceutical composition. A drug-eluting stent coated with a solid form of Compound I of the invention (or pharmaceutical composition) may be useful in the prevention of stent restenosis and thrombosis during percutaneous coronary interventions. A drug-eluting stent coated with a solid form of Compound I of the invention (or pharmaceutical composition) may be able to prevent smooth cell proliferation as well as to assist re-vascularization and re-generation of the endothelial tissue of the artery in which the stent is inserted.

An alternative to percutaneous coronary intervention for the treatment of intractable angina due to coronary artery occlusive disease is the procedure named Coronary Artery Bypass Grafting (CABG). CABG provides only palliation of an ongoing process that is further complicated by the rapid development of graft atherosclerosis. The saphenous vein graft is the most commonly used conduit in CABG surgery. The long-term clinical success of venous CABG is hampered for three main reasons: accelerated graft atherosclerosis, incomplete endothelialization and thrombosis.

In some embodiments, a solid form of Compound I of the invention can be used for the prevention of saphenous graft failure during CABG. Solid forms of the invention may assist the process of endothelialization and help prevent thrombosis. In this indication, the solid form of Compound I is delivered locally in the form of a gel.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a polymorph or a pharmaceutically acceptable salt of Compound I to the subject in need of the treatment. Alternatively, the invention provides the use of a polymorph or a pharmaceutically acceptable salt of Compound I, in the treatment of one of these diseases, conditions and disorders in a subject in need of the treatment. The invention further provides a method of making or manufacturing a medicament useful for treating one of these diseases, conditions and disorders comprising using a polymorph or a pharmaceutically acceptable salt of Compound I.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

As used herein, the terms "treatment" or "treating" are used interchangeably. These terms refer to an approach for obtaining beneficial or desired results including, but not limited to, therapeutic benefit. Therapeutic benefit includes eradication or amelioration of the underlying disorder being treated; it also includes the eradication or amelioration of one or more of the symptoms associated with the underlying disorder such that an improvement is observed in the patient, notwithstanding that the patient may still be afflicted with the underlying disorder.

As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernible symptoms) of said condition (i.e., "managing" without "curing" the condition), resulting from the administration of one or more therapies (e.g., one or more therapeutic agents such as a polymorph or pharmaceutically acceptable salt of Compound I or a composition thereof of the invention). In specific embodiments, the terms "treat"; "treatment" and "treating" refer to the amelioration of at least one measurable physical parameter of an sGC, cGMP and/or NO mediated condition. In other embodiments, the terms "treat", "treatment" and "treating" refer to the inhibition of the progression of an sGC, cGMP and/or NO mediated condition, either physically by, e.g., stabilization of a discernible symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art, it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention", with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g., a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The solid forms and pharmaceutical compositions described herein can be used alone or in combination therapy for the treatment or prevention of a disease or disorder mediated, regulated or influenced by sGC, cGMP and/or NO.

Solid forms and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a solid form or composition of the invention. Use of a sGC stimulator in a biological sample is useful for a variety of purposes known to one of skill in the art. Examples of such purposes include, without limitation, biological assays and biological specimen storage.

Combination Therapies

The solid forms and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, solid forms described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a polymorph or a pharmaceutically acceptable salt of Compound I and a second amount of an additional suitable therapeutic agent.

In one embodiment of this invention, a polymorph or a pharmaceutically acceptable salt of Compound I, and the additional therapeutic agent are each administered in an effective amount (i.e., each in an amount which would be therapeutically effective if administered alone). In another embodiment, the polymorph or pharmaceutically acceptable salt of Compound I and the additional therapeutic agent are each administered in an amount which alone does not provide a therapeutic effect (a sub-therapeutic dose). In yet another embodiment, the polymorph or pharmaceutically acceptable salt of Compound I can be administered in an effective amount, while the additional therapeutic agent is administered in a sub-therapeutic dose. In still another embodiment, the polymorph or pharmaceutically acceptable salt of Compound I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a polymorph or pharmaceutically acceptable salt of Compound I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a polymorph or pharmaceutically acceptable salt of Compound I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic amount of a polymorph or pharmaceutically acceptable salt of Compound I described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a polymorph or pharmaceutically acceptable salt of Compound I, either administered separately or in the same pharmaceutical composition include, but are not limited to:

(1) Endothelium-derived releasing factor (EDRF);
(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a antifuroxan. Some examples of these types of compounds include: glyceryl trinitrate (also known as GTN, nitroglycerin, nitroglycerine, and trinitroglycerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CINOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), Sodium Nitroprusside, S-nitrosoglutathione mono-ethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650,442, 5,700,830, 5,632,981, 6,290,981, 5,691,423 5,721,365, 5,714,511, 6,511,911, and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin IX, arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schäfer et al., Journal of Thrombosis and Homeostasis 2005; Volume 3, Supplement 1: abstract number P 1487);

(6) NO independent heme-independent sGC activators, including, but not limited to: BAY 58-2667 (see patent publication DE19943635)

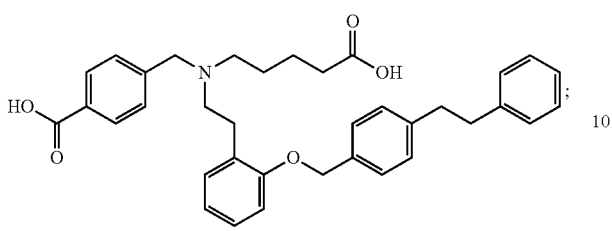

HMR-1766 (ataciguat sodium, see patent publication WO2000002851)

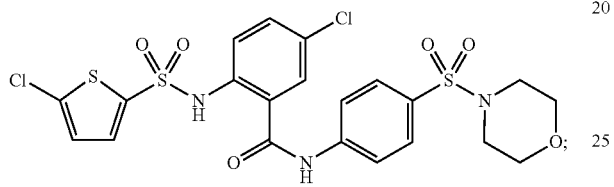

S 3448 (2-(4-chloro-phenylsulfonylamino)-4,5-dimethoxy-N-(4-(thiomorpholine-4-sulfonyl)-phenyl)-benzamide (see patent publications DE19830430 and WO2000002851)

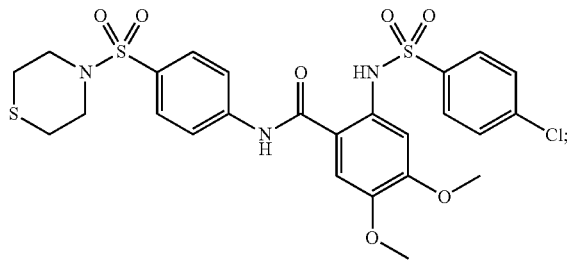 [SMILES: COc1cc(NS(=O)(=O)c2ccc(Cl)cc2)c(C(=O)Nc2ccc(S(=O)(=O)N3CCSCC3)cc2)cc1OC]

and HMR-1069 (Sanofi-Aventis).

(7) Heme-dependent sGC stimulators including, but not limited to:

YC-1 (see patent publications EP667345 and DE19744026)

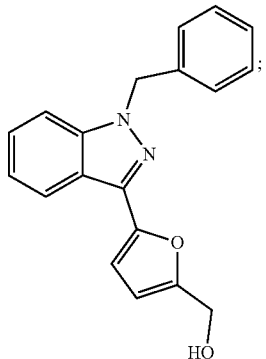 [SMILES: OCc1ccc(-c2nn(Cc3ccccc3)c3ccccc23)o1]

Riociguat (BAY 63-2521, Adempas, commercial product, described in DE19834044)

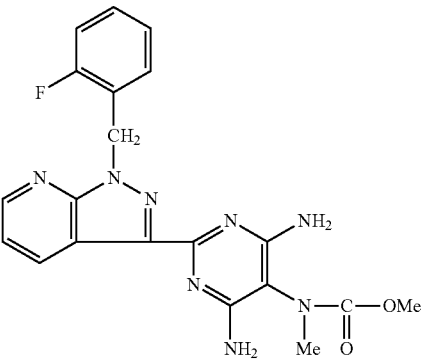 [SMILES: COC(=O)N(C)c1c(N)nc(-c2nn(Cc3ccccc3F)c3ncccc23)nc1N]

Neliciguat (BAY 60-4552, described in WO 2003095451)

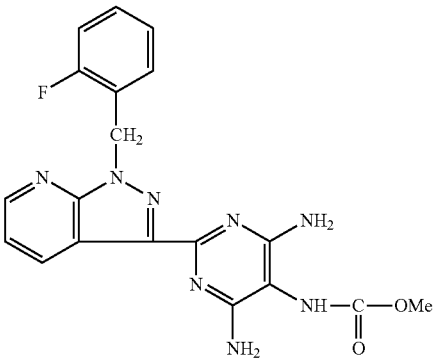 [SMILES: COC(=O)Nc1c(N)nc(-c2nn(Cc3ccccc3F)c3ncccc23)nc1N]

Vericiguat (BAY 1021189, clinical backup to Riociguat), BAY 41-2272 (described in DE19834047 and DE19942809)

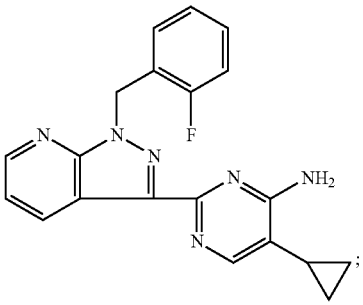 [SMILES: Nc1nc(-c2nn(Cc3ccccc3F)c3ncccc23)ncc1C1CC1]

BAY 41-8543 (described in DE19834044)

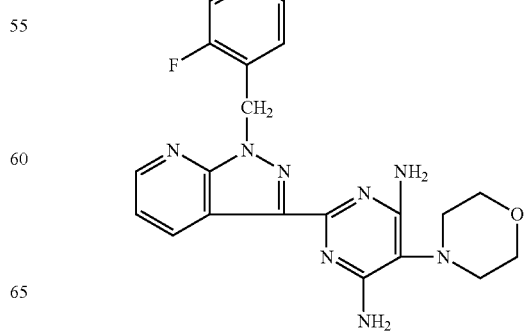

Etriciguat (described in WO 2003086407)

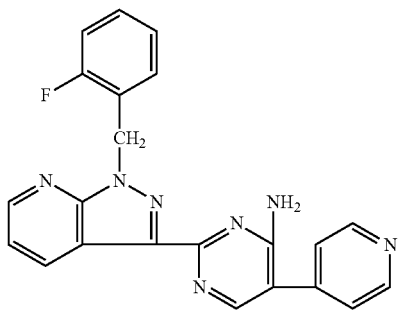 [SMILES: Nc1nc(-c2nn(Cc3ccccc3F)c3ncccc23)ncc1-c1ccncc1]

CFM-1571 (see patent publication WO2000027394)

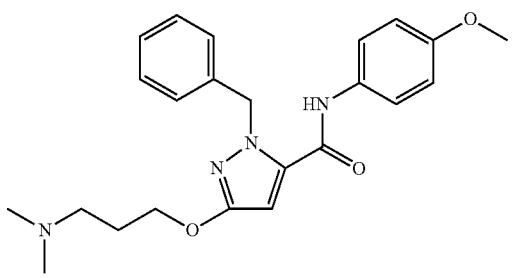

A-344905, its acrylamide analogue A-350619 and the aminopyrimidine analogue A-778935.

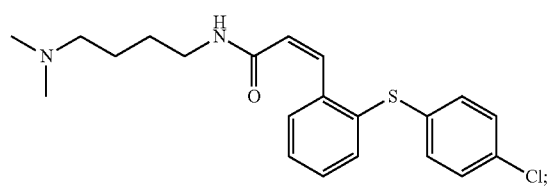

A350-619

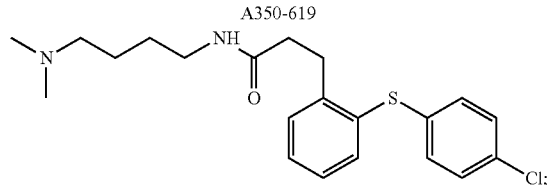

A-344905

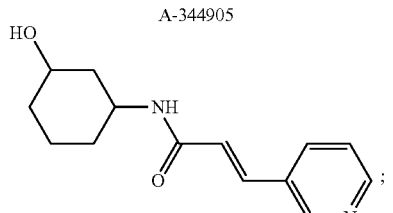

A-778935

Compounds disclosed in one of publications: US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds disclosed in Tetrahedron Letters (2003), 44(48): 8661-8663.

(8) Compounds that inhibit the degradation of cGMP, such as:

PDE5 inhibitors, such as, for example, Sildenafil (Viagra®) and other related agents such as Avanafil, Lodenafil, Mirodenafil, Sildenafil citrate (Revatio), Tadalafil (Cialis® or Adcirca®), Vardenafil (Levitra®) and Udenafil; Alprostadil; and Dipyridamole; PF-00489791

PDE9 inhibitors, such as, for example, PF-04447943;

(9) Calcium channel blockers such as:

Dihydropyridine calcium channel blockers: Amlodipine (Norvasc), Aranidipine (Sapresta), Azelnidipine (Calblock), Bamidipine (HypoCa), Benidipine (Coniel), Cilnidipine (Atelec, Cinalong, Siscard), Clevidipine (Cleviprex), Diltiazem, Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Isradipine (Lomir);

Phenylalkylamine calcium channel blockers: Verapamil (Calan, Isoptin)

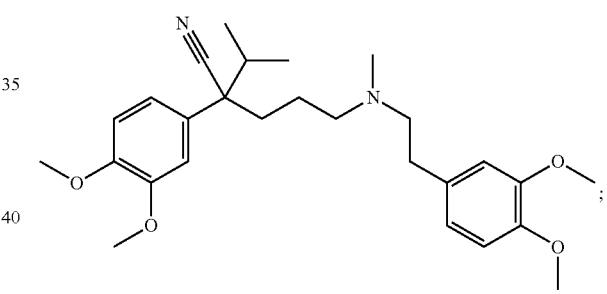

Gallopamil (Procorum, D600);

Benzothiazepines: Diltiazem (Cardizem);

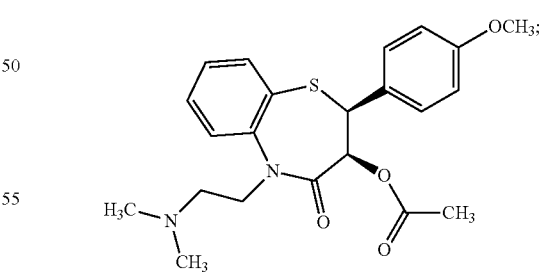

Nonselective calcium channel inhibitors such as: mibefradil, bepridil and fluspirilene, fendiline;

(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S.; dual/nonselective endothelin antagonist Actelion-1, that entered clinical trials in 2008;

(11) Prostacyclin derivatives or analogues: for instance prostacyclin (prostaglandin I$_2$), Epoprostenol (synthetic prostacyclin, marketed as Flolan®); Treprostinil (Remodulin®), Iloprost (Ilomedin), Iloprost (marketed as Ventavis®); oral and inhaled forms of Remodulin® that are under development; Beraprost, an oral prostanoid available in Japan and South Korea;

(12) Antihyperlipidemics such as: bile acid sequestrants (e.g., Cholestyramine, Colestipol, Colestilan and Colesevelam); statins such as Atorvastatin, Simvastatin, Lovastatin, Fluvastatin, Pitavastatin, Rosuvastatin and Pravastatin; cholesterol absorption inhibitors such as Ezetimibe; other lipid lowering agents such as Icosapent ethyl ester, Omega-3-acid ethyl esters, Reducol; fibric acid derivatives such as Clofibrate, Bezafibrate, Clinofibrate, Gemfibrozil, Ronifibrate, Binifibrate, Fenofirate, Ciprofibrate, Choline fenofibrate; nicotinic acid derivatives such as Acipimox and Niacin; also combinations of statins, niacin, intestinal cholesterol absorption-inhibiting supplements (ezetimibe and others) and fibrates; antiplatelet therapies such as Clopidogrel bisulfate;

(13) Anticoagulants, such as the following types:
  Coumarines (Vitamin K antagonists): Warfarin® (Coumadin) mostly used in the US and UK: Acenocoumarol® and Phenprocoumon®, mainly used in other countries; Phenindione®;
  Heparin and derivative substances such as: Heparin; low molecular weight heparin, Fondaparinux and Idraparinux;
  Direct thrombin inhibitors such as: Argatroban, Lepirudin, Bivalirudin and Dabigatran; Ximelagatran (Exanta®), not approved in the US;
  Tissue plasminogen activators, used to dissolve clots and unblock arteries, such as Alteplase;

(14) Antiplatelet drugs: for instance thienopyridines such as Lopidogrel and Ticlopidine; Dipyridamole; Aspirin;

(15) ACE inhibitors, for example the following types:
  Sulfhydryl-containing agents such as Captopril (trade name Capoten®), the first ACE inhibitor and Zofenopril;
  Dicarboxylate-containing agents such as Enalapril (Vasotec/Renitec®); Ramipril (Altace/Tritace/Ramace/Ramiwin®); Quinapril (Accupril®), Perindopril (Coversyl/Aceon®); Lisinopril (Lisodur/Lopril/Novatec/Prinivil/Zestril®) and Benazepril (Lotensin®);
  Phosphonate-containing agents such as: Fosinopril;
  Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;
  Other ACE inhibitors such as Alacepril, Delapril, Cilazapril, Imidapril, Trandolapril, Temocapril, Moexipril, Spirapril,

(16) Supplemental oxygen therapy;

(17) Beta blockers, such as the following types:
  Non-selective agents: Alprenolol®, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Oxprenonol, Acebutolol, Sotalol, Mepindolol, Celiprolol, Arotinolol, Tertatolol, Amosulalol, Nipradilol, Propranolol® and Timolol®;
  $β_1$-Selective agents: Acebutolol® (has intrinsic sympathomimetic activity), Atenolol®, Betaxolol®, Bisoprolol®, Celiprolol®, Dobutamine hydrochloride, Irsogladine maleate, Carvedilol, Talinolol, Esmolol®, Metoprolol® and Nebivolol®;
  $β_2$-Selective agents: Butaxamine® (weak α-adrenergic agonist activity);

(18) Antiarrhythmic agents such as the following types:
  Type I (sodium channel blockers): Quinidine, Lidocaine, Phenytoin, Propafenone
  Type III (potassium channel blockers): Amiodarone, Dofetilide, Sotalol
  Type V: Adenosine, Digoxin

(19) Diuretics such as: Thiazide diuretics, e.g., Chlorothiazide, Chlorthalidone, and Hydrochlorothiazide, Bendroflumethiazide, Cyclopenthiazide, Methyclothiazide, Polythiazide, Quinethazone, Xipamide, Metolazone, Indapamide, Cicletanine; Loop diuretics, such as Furosemide and Toresamide; potassium-sparing diuretics such as Amiloride, Spironolactone, Canrenoate potassium, Eplerenone and Triamterene; combinations of these agents; other diuretics such as Acetazolamid and Carperitide (20a) Direct-acting vasodilators such as Hydralazine hydrochloride, Diazoxide, Sodium nitroprusside, Cadralazine; other vasodilators such as Isosorbide dinitrate and Isosorbide 5-mononitrate;

(20b) Exogenous vasodilators such as:
  Adenocard®, an adenosine agonist, primarily used as an anti-arrhythmic;
  Alpha blockers (which block the vasoconstricting effect of adrenaline): Alpha-1-adrenoceptor antagonists such as Prazosin, Indoramin, Urapidil, Bunazosin, Terazosin, Doxazosin
  Atrial natriuretic peptide (ANP);
  Ethanol;
  Histamine-inducers, which complement proteins C3a, C4a and C5a work by triggering histamine release from mast cells and basophil granulocytes;
  Tetrahydrocannabinol (THC), major active chemical in marijuana which has minor vasodilatory effects;
  Papaverine, an alkaloid found in the opium poppy Papaver Somniferum;

(21) Bronchodilators: there are two major types of bronchodilator, $β_2$ agonists and anticholinergics, exemplified below:
  $β_2$ agonists: Salbutamol® or albuterol (common brand name: Ventolin) and Terbutaline® are short acting $β_2$ agonists for rapid relief of COPD symptoms. Long acting $β_2$ agonists (LABAs) such as Salmeterol® and Formoterol®;
  anticholinergics: Ipratropium® is the most widely prescribed short acting anticholinergic drug. Tiotropium® is the most commonly prescribed long-acting anticholinergic drug in COPD;
  Theophylline®, a bronchodilator and phosphodiesterase inhibitor;

(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide

(23) Dietary supplements such as, for example: omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Testosterone transdermal patch; Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;

(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WOO 178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY 1005);

(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(28) Cyclooxygenase-2 (COX-2) inhibitors such as celecoxib (Celebrex®), rofecoxib (Vioxx®), valdecoxib, etoricoxib, parecoxib and lumiracoxib;

(opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and

(29) Anti-diabetic agents such as insulin and insulin mimetics, sulfonylureas (e.g., Glyburide, Glybenclamide, Glipizide, Gliclazide, Gliquidone, Glimepiride, Meglinatide, Tolbutamide, Chlorpropamide, Acetohexamide, Tolazamide), biguanides, e.g., metformin (Glucophage®), α-glucosidase inhibitors (such as Acarbose, Epalrestat, Voglibose, Miglitol), thiazolidinone compounds, e.g., rosiglitazone (Avandia®), troglitazone (Rezulin®), ciglitazone, pioglitazone (Actos®) and englitazone; insulin sensitizers such as Pioglitazone and Rosiglitazone; Insulin secretagogues such as Repaglinide, Nateglinide and Mitiglinide; Incretin mimetics such as Exanatide and Liraglutide; Amylin analogues such as Pramlintide; glucose lowering agents such as Chromium picolinate (optionally combined with biotin); dipeptidyl peptidase IV inhibitors such as Sitagliptin, Vildagliptin, Saxagliptin, Alogliptin and Linagliptin; vaccines currently being developed for the treatment of diabetes; AVE-0277, Alum-GAD, BHT-3021, IBC-VSO1; cytokine targeted therapies in development for the treatment of diabetes such as Anakinra, Canakinumab, Diacerein, Gevokizumab, LY-2189102, MABP-1, GIT-027;

(30) HDL cholesterol-increasing agents such as Anacetrapib, MK-524A, CER-001, DRL-17822, Dalcetrapib, JTT-302, RVX-000222, TA-8995;

(31) Antiobesity drugs such as Methamphetamine hydrochloride, Amfepramone hydrochloride (Tenuate®), Phentermine (Ionamin®), Benzfetamine hydrochloride (Didrex®), Phendimetrazine tartrate (Bontril®, Prelu-2 ®, Plegine®), Mazindol (Sanorex®), Orlistat (Xenical®), Sibutramine hydrochloride monohydrate (Meridia®, Reductil®), Rimonabant (Acomplia®), Amfepramone, Chromium picolinate, RM-493, TZP-301; combination such as Phentermine/Topiramate, Bupropion/Naltrexone, Sibutramine/Metformin, Bupropion SR/Zonisamide SR, Salmeterol, xinafoate/fluticasone propionate; Lorcaserin hydrochloride, Phentermine/topiramate, Bupropion/naltrexone, Cetilistat, Exenatide, KI-0803, Liraglutide, Metformin hydrochloride, Sibutramine/Metformin, 876167, ALS-L-1023, Bupropion SR/Zonisamide SR, CORT-108297, Canagliflozin, Chromium picolinate, GSK-1521498, LY-377604, Metreleptin, Obinepitide, P-57AS3, PSN-821, Salmeterol xinafoate/fluticasone propionate, Sodium tungstate, Somatropin (recombinant), TM-30339, TTP-435, Tesamorelin, Tesofensine, Velneperit, Zonisamide, BMS-830216, ALB-127158, AP-1030, ATHX-105, AZD-2820, AZD-8329, Beloranib hemioxalate, CP-404, HPP-404, ISIS-FGFR4Rx, Insulinotropin, KD-3010PF, 05212389, PP-1420, PSN-842, Peptide YY3-36, Resveratrol, S-234462; S-234462, Sobetirome, TM-38837, Tetrahydrocannabivarin, ZYO-1, beta-Lapachone;

(32) Angiotensin receptor blockers such as Losartan, Valsartan, Candesartan cilexetil, Eprosaran, Irbesartan, Telmisartan, Olmesartran medoxomil, Azilsartan medoxomil;

(33) Renin inhibitors such as Aliskiren hemifumirate;

(34) Centrally acting alpha-2-adrenoceptor agonists such as Methyldopa, Clonidine, Guanfacine;

(35) Adrenergic neuron blockers such as Guanethidine, Guanadrel;

(36) Imidazoline I-1 receptor agonists such as Rimenidine dihydrogen phosphate and Moxonidine hydrochloride hydrate;

(37) Aldosterone antagonists such as Spironolactone and Eplerenone

(38) Potassium channel activators such as Pinacidil

(39) Dopamine D1 agonists such as Fenoldopam mesilate; Other dopamine agonists such as Ibopamine, Dopexamine and Docarpamine;

(40) 5-HT2 antagonists such as Ketanserin;

(42) Vasopressin antagonists such as Tolvaptan;

(43) Calcium channel sensitizers such as Levosimendan or activators such as Nicorandil;

(44) PDE-3 inhibitors such as Amrinone, Milrinone, Enoximone, Vesnarinone, Pimobendan, Olprinone;

(45) Adenylate cyclase activators such as Colforsin dapropate hydrochloride;

(46) Positive inotropic agents such as Digoxin and Metildigoxin; metabolic cardiotonic agents such as Ubidecarenone; brain naturetic peptides such as Nesiritide;

(47) Drugs used for the treatment of erectile dysfunction such as Alprostadil, Aviptadil, Phentolamine mesilate, Weige, Alprostadil;

(48) Antiobesity drugs:

| Antiobesity drugs: Drugs marketed for the treatment of obesity | | | |
|---|---|---|---|
| Methamphetamine hydrochloride (Desoxyn) | Abbott | Noradrenergic, alpha- and beta- adrenoceptor agonist | 1943 (U.S.) |
| Amfepramone hydrochloride (Tenuate) | Sanofi | Noradrenergic release stimulant | 1959 (U.S.) |
| Phentermine (Ionamin) | UCB Celltech | Noradrenergic release stimulant | 1959 (U.S.) |
| Benzfetamine hydrochloride (Didrex) | Pfizer | Noradrenergic release stimulant | 1960 (U.S.) |
| Phendimetrazine tartrate (Bontril, Prelu-2, Plegine) | Pfizer | Noradrenergic release stimulant | 1961 (U.S.) |
| Mazindol (Sanorex) | Novartis | Noradrenergic reuptake inhibitor | 1973 (U.S.) |
| Orlistat (Xenical) | Roche | Pancreatic lipase inhibitor | 1998 (New Zealand) |

(49) Drugs used for the treatment of Alzheimer's disease: e.g., cholinesterase inhibitors prescribed for mild to moderate Alzheimer's disease, including Razadyne® (galantamine), Exelon® (rivastigmine), and Aricept® (donepezil), Cognex® (tacrine); Namenda® (memantine), an N-methyl D-aspartate (NMDA) antagonist, and Aricept®, prescribed to treat moderate to severe Alzheimer's disease: vitamin E (an anti-oxidant).
(50) Antidepressants: tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citalopram (Celexa®); and others such as doxepin (Sinequan®) and trazodone (Desyrel®); SNRIs (e.g., venlafaxine and reboxetine); dopaminergic antidepressants (e.g., bupropion and aminepine).
(51) Neuroprotective agents: e.g., memantine, L-dopa, bromocriptine, pergolide, talipexol, pramipexol, cabergoline, neuroprotective agents currently under investigation including anti-apoptotic drugs (CEP 1347 and CTCT346), lazaroids, bioenergetics, antiglutamatergic agents and dopamine receptors. Other clinically evaluated neuroprotective agents are, e.g., the monoamine oxidase B inhibitors selegiline and rasagiline, dopamine agonists, and the complex I mitochondrial fortifier coenzyme Q10.
(52) Antipsychotic medications: e.g., ziprasidone (Geodon™), risperidone (Risperdal™), and olanzapine (Zyprexa™).
(53) NEP inhibitors such as Sacubitril, Omapatrilat.
(54) Methylene Blue (MB).

Kits

The solid forms and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

Example 1: Preparation of Crude Compound I i): Coupling of Compound (1') and N,O-Dimethylhydroxylamine to Provide N-methoxy-N-methyl-isoxazole-3-carboxamide (2')

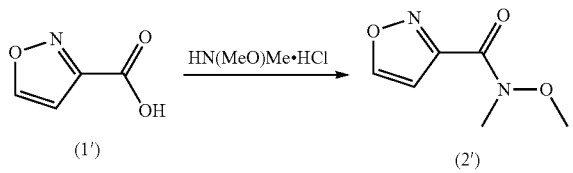

Isooxazole-3-carboxylic acid ((1'), 241.6 g, 2137 mmoles, 1.0 equiv.), toluene (1450 mL) and DMF (7.8 g, 107 mmoles, 0.05 equiv.) were charged to a suitable reaction vessel equipped with a mechanical stirrer and a digital thermometer. The resulting slurry was heated to 45-50° C. Oxalyl chloride (325 g, 2559 mmoles, 1.2 equiv.) was then charged via an addition funnel over the course of 2 h while maintaining the reaction temperature between 45 to 50° C. and a vigorous gas evolution was observed. A brown mixture was obtained after addition. The brown mixture was heated to 87 to 92° C. over 1 h and stirred at 87 to 92° C. for 1 h. The reaction was completed as shown by HPLC. During heating, the brown mixture turned into a dark solution. The reaction was monitored by quenching a portion of the reaction mixture into piperidine and monitoring the piperidine amide by HPLC. The dark mixture was cooled to 20-25° C. and then filtered through a sintered glass funnel to remove any insolubles. The dark filtrate was concentrated under reduced pressure to a volume of 400 mL dark oil.

Potassium carbonate (413 g, 2988 mmoles, 1.4 equiv.) and water (1000 mL) were charged to a suitable reaction vessel equipped with a mechanical stirrer and a digital thermometer. The reaction solution was cooled to −10 to −5° C. N,O-dimethylhydroxyamine hydrochloride (229 g, 2348 mmoles, 1.1 equiv.) was charged to a suitable reaction vessel and dissolved in water (1000 mL). The N,O-dimethylhydroxyamine solution and dichloromethane (2500 mL) were then charged to the potassium carbonate solution.

The above dark oil (400 mL) was then charged slowly via an addition funnel while maintaining the reaction temperature −10 to 0° C. The addition was slightly exothermic and a brown mixture was obtained after addition. The mixture was stirred at 0 to 5° C. over 20 min. and then warmed to 20 to 25° C. The bottom organic layer was collected and the top aq. layer was extracted with dichloromethane (400 mL). The combined organic layers were washed with 15% sodium chloride solution (1200 mL). The organic layer was dried over magnesium sulfate and then filtered. The filtrate was concentrated under reduced pressure to give intermediate (2') as a dark oil (261.9 g, 97 wt %, 76% yield, 3 wt % toluene by $^1$H-NMR, 0.04 wt % water content by KF).

$^1$H-NMR (500 MHz, CDCl$_3$) δ ppm 8.48 (s, 1H); 6.71 (s, 1H); 3.78 (s, 3H); 3.38 (s, 3H).

ii): Alkylation of Compound (2') and Ethyl Propiolate to Provide (E)-ethyl 4-(isoxazol-3-yl)-2-(methoxy(methyl)amino)-4-oxobut-2-enoate (3')

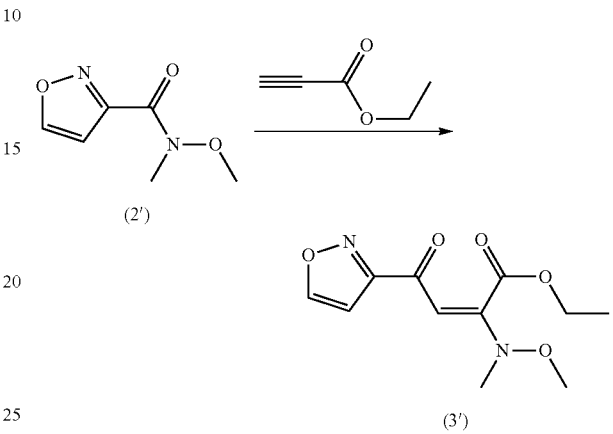

Intermediate (2') (72.2 g, 96 wt %, 444 mmoles, 1.0 equiv.), ethyl propiolate (65.7 g, 670 mmoles, 1.5 equiv.) and anhydrous THF (650 mL) were charged to a suitable reaction vessel equipped with a mechanical stirrer and a digital thermometer. The solution was cooled to −65 to −55° C. Sodium bis(trimethylsilyl)amide in THF (1 M, 650 mL, 650 mmoles, 1.46 equiv.) was then charged slowly via an addition funnel while maintaining the reaction temperature −65 to −55° C. The mixture was stirred below −55° C. over 10 min. after addition was complete. Then 1 N HCl (650 mL, 650 mmoles, 1.46 equiv.) was charged to quench the reaction while maintaining the reaction temperature below −20° C. followed immediately with the addition of ethyl acetate (1500 mL) and water (650 mL). The top ethyl acetate layer was collected and the bottom aqueous layer was extracted with ethyl acetate (800 mL). The combined organic layers were washed with 10% citric acid (1000 mL) and saturated sodium chloride solution (650 mL). The organic layer was concentrated under reduced pressure to give a dark oil.

The dark oil was dissolved in a solution of dichloromethane/ethyl acetate/heptane (150 mL/100 mL/100 mL). The solution was loaded on a silica pad (410 g) and the silica pad was eluted with ethyl acetate/heptane (1/1 v/v). The filtrate (~3000 mL) was collected and then concentrated under reduced pressure to a volume of 150 mL to give a slurry upon standing. Heptane (200 mL) was then added to the slurry and the slurry was concentrated under reduced pressure to a volume of 150 mL. The resulting slurry was filtered, and the filter cake was washed with heptane (150 mL). The filter cake was then air dried overnight to furnish intermediate (3') as a brown solid (63.4 g, 56% yield, >99% pure by HPLC). $^1$H-NMR (500 MHz, CDCl$_3$) δ ppm 8.42 (d, J=1.53 Hz, 1H); 6.76 (d, J=1.53 Hz, 1H); 6.18 (s, 1H); 4.47 (q, J=7.07 Hz, 2H); 3.75 (s, 3H); 3.21 (s, 3H); 1.41 (t, J=7.17 Hz, 3H).

iii): Cyclization of Compound 3' and 2-fluorobenzylhydrazine to Provide ethyl 1-(2-fluorobenzyl)-5-(isoxazol-3-yl)-1H-pyrazole-3-carboxylate (4')

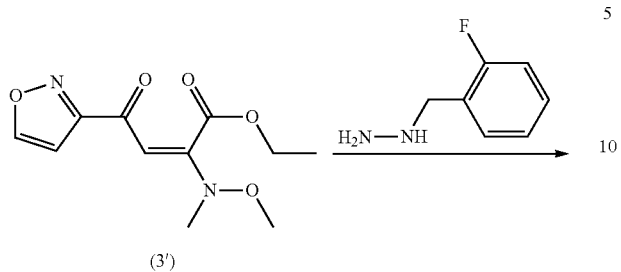

(3')

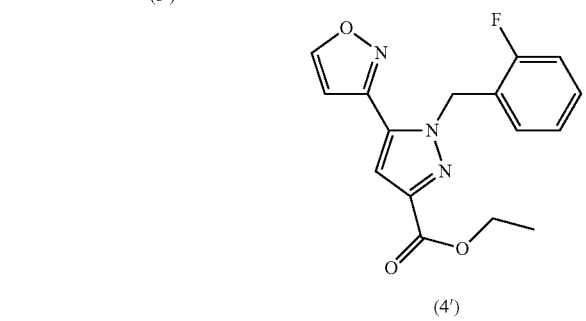

(4')

Intermediate (3') (72.9 g, 287 mmoles, 1.0 equiv.) and absolute ethanol (730 mL) were charged to a suitable reaction vessel equipped with a mechanical stirrer and a digital thermometer. The mixture was cooled to 0 to 5° C. 2-Fluorobenzylhydrazine (48.2 g, 344 mmoles, 1.2 equiv.) was then charged to the mixture. The mixture was stirred at 0 to 10° C. over 1 h and then warmed to 20 to 25° C. and stirred at 20 to 25° C. over 16 h. The reaction was completed by HPLC. Concentrated HCl (33.9 g, 37 wt %, 344 mmoles, 1.2 equiv.) was charged to the reaction mixture over 1 min and the batch temperature exothermed from 20° C. to 38° C. A slurry was obtained. The mixture was cooled to 0 to 10° C. over 1 h and stirred at 0-10° C. for 1 h. The resulting slurry was filtered, and the filter cake was washed with ethanol (200 mL). The filter cake was dried under vacuum at 30 to 40° C. over 16 h to furnish intermediate (4') as an off-white solid (81.3 g, 90% yield, >99% pure by HPLC). ¹H-NMR (500 MHz, CDCl₃) δ ppm 8.47 (d, J=1.68 Hz, 1H); 7.15-7.26 (m, 2H); 6.94-7.08 (m, 2H); 6.77-6.87 (m, 1H); 6.55 (d, J=1.68 Hz, 1H); 5.95 (s, 2H); 4.43 (q, J=7.02 Hz, 2H); 1.41 (t, J=7.17 Hz, 3H).

iv): Amination of Compound (4') to Provide 1-(2-fluorobenzyl)-5-(isoxazol-3-yl)-1H-pyrazole-3-carboximidamide hydrochloride (5'B)

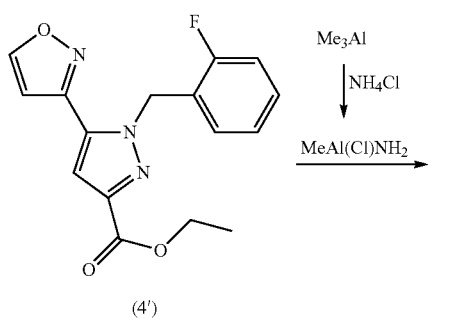

(4')

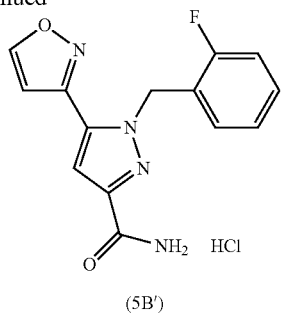

(5B')

Anhydrous ammonium chloride (267 g, 4991 mmoles, 5.0 equiv.) and toluene (5400 mL) were charged to a suitable reaction vessel equipped with a mechanical stirrer and a digital thermometer. Trimethylaluminum in toluene (2 M, 2400 mL, 4800 mmoles, 4.8 equiv.) was charged slowly via an addition funnel while maintaining the reaction temperature at 20 to 40° C. (Note: Methane gas evolution was observed during addition). Then the mixture was heated to 75 to 80° C. over 30 min. and a clear white solution was obtained. Intermediate (4') (315 g, 999 mmoles, 1.0 equiv.) was charged to reaction mixture in four equal portions over 1 h at 75 to 90° C. The reaction was stirred at 80 to 90° C. over 30 min. and then heated to 100 to 110° C. and stirred at 100 to 110° C. over 3 h. The reaction was completed by HPLC. The reaction mixture was cooled to 10 to 20° C. and methanol (461 g, 14.4 moles, 14.4 equiv.) was charged slowly via an addition funnel while maintaining the reaction temperature 10-40° C. Note the quenching was very exothermic and a lot gas evolution was observed. A thick slurry was obtained. A 3N HCl (6400 mL, 3 N, 19.2 moles, 19.2 equiv.) was then charged slowly via an addition funnel while maintaining the reaction temperature at 20 to 45° C. The mixture was heated to 80 to 85° C. and stirred at 80 to 85° C. over 10 min. to obtain a clear biphasic mixture. The mixture was cooled to 0 to 5° C. over 3 h and stirred at 0 to 5° C. over 1 h. The resulting slurry was filtered, and the filter cake was washed with water (3000 mL). The filter cake was dried under vacuum at 40 to 50° C. over 24 h to furnish intermediate (5'B) as an off-white solid (292 g, 91% yield, >99% pure by HPLC). ¹H-NMR (500 MHz, DMSO-d₆) δ ppm 9.52 (s, 2H); 9.33 (s, 2H); 9.18 (d, J=1.53 Hz, 1H); 7.88 (s, 1H); 7.29-7.38 (m, 1H); 7.19-7.25 (m, 1H); 7.10-7.16 (m, 1H); 7.03 (d, J=1.53 Hz, 1H); 6.92-6.98 (m, 1H); 5.91 (s, 2H). M.P. 180-185° C.

v): Cyclization of Compound (5'B) and Diethyl Fluoromalonate to Provide 5-fluoro-2-(1-(2-fluorobenzyl)-5-(isoxazol-3-yl)-1H-pyrazol-3-yl)pyrimidine-4,6-diol (6')

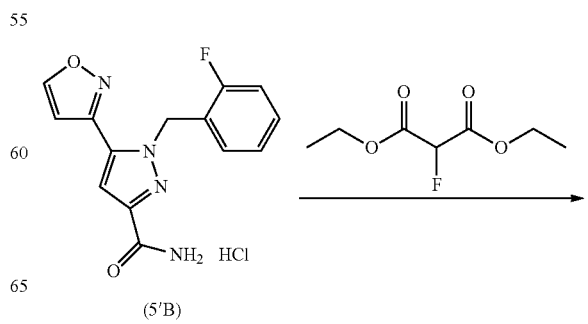

(5'B)

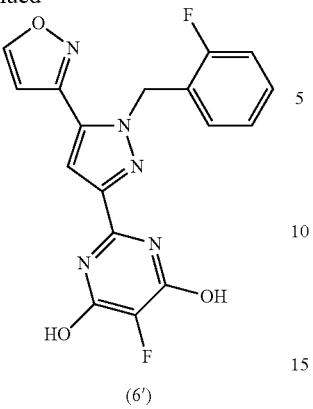

(6')

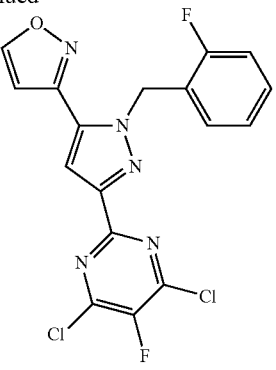

(7')

Intermediate (5'B) (224.6 g, 698 mmoles, 1.0 equiv.), methanol (2250 mL) and diethyl fluoromalonate (187 g, 1050 mmoles, 1.5 equiv.) were charged to a suitable reaction vessel equipped with a mechanical stirrer and a digital thermometer. Then sodium methoxide in methanol solution (567 g, 30 wt %, 3149 mmoles, 4.5 equiv.) was charged via an addition funnel while maintaining the reaction temperature 20 to 35° C. The mixture was stirred at 20 to 35° C. over 30 min. and a light suspension was obtained. The reaction was completed by HPLC. A solution of 1.5 N HCl (2300 mL, 3450 mmoles, 4.9 equiv.) was charged via an addition funnel over 1 h while maintaining the reaction temperature 20 to 30° C. A white suspension was obtained. The pH of the reaction mixture was to be ~1 by pH paper. The slurry was stirred at 20 to 30° C. over 30 min. The resulting slurry was filtered, and the filter cake was washed with a pre-mixed solution of methanol and water (500 mL/500 mL), and then with water (1000 mL). The filter cake was dried under vacuum at 50 to 60° C. over 16 h to furnish intermediate (6') as an off-white solid (264 g, 97% yield, >99% pure by HPLC). $^1$H-NMR (500 MHz, DMSO-$d_6$) δ ppm 12.82 (br. s., 1H); 12.31 (br. s., 1H); 9.14 (d, J=1.53 Hz, 1H); 7.55 (s, 1H); 7.31-7.37 (m, 1H); 7.18-7.25 (m, 1H); 7.10-7.15 (m, 2H); 6.97-7.02 (t, J=7.55 Hz, 1H); 5.88 (s, 2H).

vi): Chlorination of Compound (6') to Provide 3-(3-(4,6-dichloro-5-fluoropyrimidin-2-yl)-1-(2-fluorobenzyl)-1H-pyrazol-5-yl)isoxazole (7')

Intermediate (6') (264 g, 711 mmoles, 1.0 equiv.), acetonitrile (4000 mL) and N,N-dimethylaniline (138 g, 1137 mmoles, 1.6 equiv.) were charged to a suitable reaction vessel equipped with a mechanical stirrer and a digital thermometer. The slurry mixture was heated to 70-80° C. Then phosphorous oxychloride (655 g, 4270 mmoles, 6.0 equiv.) was charged via an addition funnel over 1 h while maintaining the reaction temperature 70 to 80° C. The mixture was stirred at 75 to 80° C. over 22 h and a brown solution was obtained. The reaction was completed by HPLC. Then the mixture was cooled to between 0 and 5° C. and cotton like solids precipitated out at 25° C. Water (3000 mL) was charged slowly via an addition funnel while maintaining the reaction temperature at 0 to 10° C. The slurry was stirred at 0 to 10° C. over 30 min. The resulting slurry was filtered, and the filter cake was washed with a pre-mixed solution of acetonitrile and water (500 mL/500 mL). The filter cake was dried under vacuum at 35 to 45° C. over 16 h to furnish intermediate (7') as an off-white solid (283 g, 98% yield, >99% pure by HPLC). $^1$H-NMR (500 MHz, CDCl$_3$) δ ppm 8.48 (d, J=1.68 Hz, 1H); 7.44 (s, 1H); 7.19-7.25 (m, 1H); 6.96-7.08 (m, 2H); 6.81-6.88 (m, 1H); 6.60 (d, J=1.68 Hz, 1H); 6.03 (s, 2H).

vii): Substitution of Compound (7') with Methoxide to Provide 3-(3-(4-chloro-5-fluoro-6-methoxypyrimidin-2-yl)-1-(2-fluorobenzyl)-1H-pyrazol-5-yl)isoxazole (8')

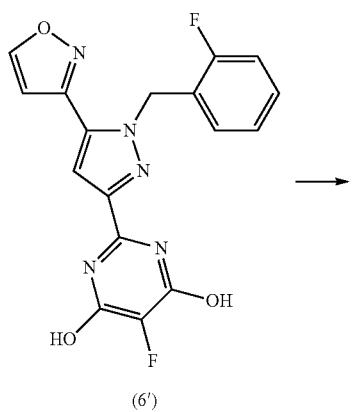

(6')

→

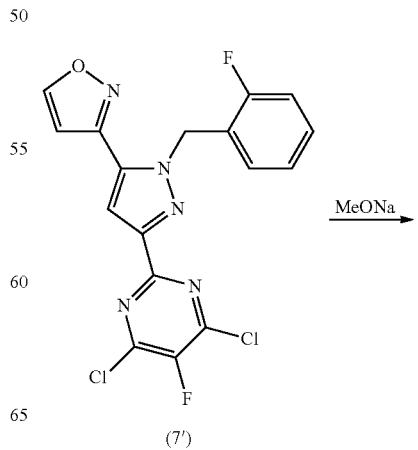

(7')

MeONa→

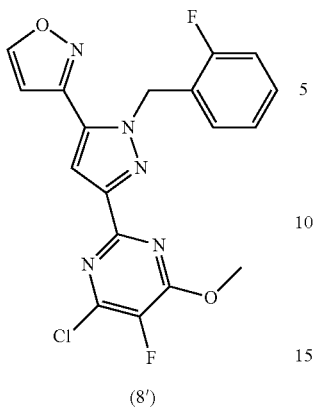

(8')

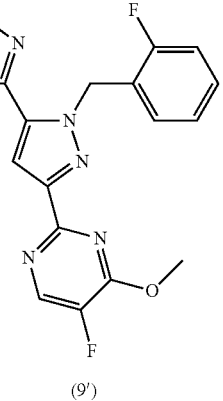

(9')

Methanol (3400 mL) and sodium methoxide in methanol (154 mL, 5.4 M, 832 mmoles, 1.2 equiv.) were charged to a suitable reaction vessel equipped with a mechanical stirrer and a digital thermometer. The reaction mixture was heated to 23 to 27° C. Intermediate (7') (283 g, 693 mmoles, 1.0 equiv.) was charged to the mixture in small portions (5-10 g each portion) over 40 min while maintaining the reaction temperature 23 to 27° C. The slurry was stirred at 23 to 27° C. over 30 min. The reaction was completed by HPLC. The resulting slurry was filtered, and the filter cake was washed with methanol (850 mL) and then water (850 mL). The filter cake was dried under vacuum at 35 to 45° C. over 16 h to furnish intermediate (8') as an off-white solid (277 g, 99% yield, 97% pure by HPLC). $^1$H-NMR (500 MHz, CDCl$_3$) δ ppm 8.47 (d, J=1.83 Hz, 1H); 7.38 (s, 1H); 7.18-7.25 (m, 1H); 7.01-7.08 (m, 1H); 6.94-7.00 (m, 1H); 6.81-6.88 (m, 1H); 6.60 (d, J=1.68 Hz, 1H); 6.00 (s, 2H); 4.21 (s, 3H).

viii): Hydrogenation of Compound (8') to Provide 3-(3-(5-fluoro-4-methoxypyrimidin-2-yl)-1-(2-fluorobenzyl)-1H-pyrazol-5-yl)isoxazole (9')

Intermediate (8') (226 g, 560 mmoles, 1.0 equiv.), palladium (10% on activated carbon, nominally 50% water wet, 22.6 g, 0.01 moles, 0.018 equiv), tetrahydrofuran (3400 mL) and triethylamine (91 g, 897 mmoles, 1.6 equiv.) were charged to a suitable reaction vessel equipped with a mechanical stirrer and a digital thermometer. Nitrogen was bubbled into the reaction mixture via teflon tubing over 10 min. at 20 to 30° C. Then the mixture was heated to 40 to 50° C. and hydrogen gas was bubbled into the reaction mixture via teflon tubing over 6 h while maintaining the reaction temperature 40 to 50° C. The reaction was completed by HPLC. Nitrogen was then bubbled into the reaction mixture via teflon tubing over 10 min. at 40 to 50° C. The reaction mixture was hot filtered through Hypo Supercel™ and the filter cake was washed with tetrahydrofuran (2000 mL). The filtrate was concentrated under reduced pressure to a volume of ~1300 mL to give a slurry. Tetrahydrofuran was then solvent exchanged to methanol under reduced pressure via continuously feeding methanol (3000 mL). The final volume after solvent exchange was 1300 mL. The resulting slurry was filtered, and the filter cake was washed with methanol (500 mL). The filter cake was dried under vacuum at 20 to 25° C. over 16 h to furnish intermediate (9') as a white solid (192 g, 93% yield, 98% pure by HPLC). $^1$H-NMR (500 MHz, CDCl$_3$) δ ppm 8.47 (d, J=1.68 Hz, 1H); 8.41 (d, J=2.59 Hz, 1H); 7.36 (s, 1H); 7.17-7.24 (m, 1H); 6.95-7.07 (m, 2H); 6.83-6.90 (m, 1H); 6.60 (d, J=1.68 Hz, 1H); 5.99 (s, 2H); 4.19 (s, 3H).

ix: Demethylation of Compound (9') to Provide 5-fluoro-2-(1-(2-fluorobenzyl)-5-(isoxazol-3-yl)-1H-pyrazol-3-yl)pyrimidin-4-ol (10')

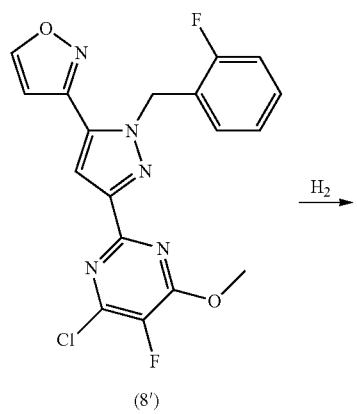

(8')

H$_2$ →

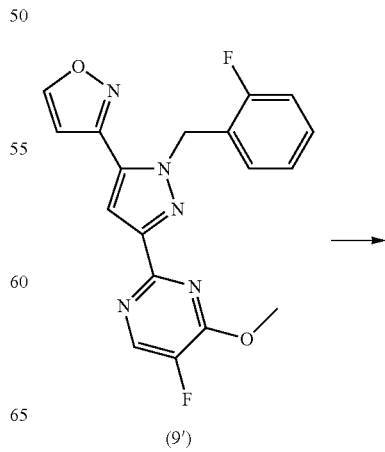

(9')

→

-continued

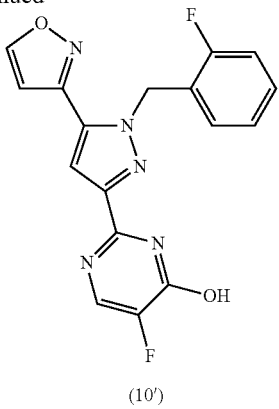

(10')

Intermediate (9') (230 g, 623 mmoles, 1.0 equiv.), MeOH (3450 mL) and conc. HCl (307 g, 37 wt %, 3117 mmoles, 5.0 equiv.) were charged to a suitable reaction vessel equipped with a mechanical stirrer and a digital thermometer. The mixture was heated to 60 to 65° C. and a solution was obtained. The mixture was then stirred at 60 to 65° C. over 17 h and a slurry was obtained. The reaction was completed by HPLC. The slurry was cooled to 20 to 25° C. over 2 h and stirred at 20 to 25° C. over 30 min. The resulting slurry was filtered, and the filter cake was washed with methanol (1000 mL). The filter cake was dried under vacuum at 35 to 45° C. over 16 h to furnish intermediate (10') as a white solid (214 g, 97% yield, >99% pure by HPLC). $^1$H-NMR (500 MHz, DMSO-$d_6$) δ ppm 12.90-13.61 (br. s., 1H); 9.11 (d, J=1.68 Hz, 1H); 8.16 (s, 1H); 7.64 (s, 1H); 7.29-7.42 (m, 1H); 7.17-7.28 (m, 2H); 7.08-7.15 (m, 1H); 6.97 (s, 1H); 5.91 (s, 3H).

x): Chlorination of Compound (10') to Provide 3-(3-(4-chloro-5-fluoropyrimidin-2-yl)-1-(2-fluorobenzyl)-1H-pyrazol-5-yl)isoxazole (Formula IV)

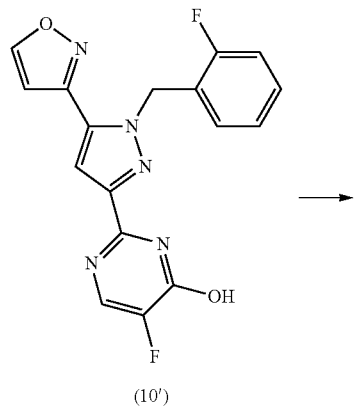

(10')

→

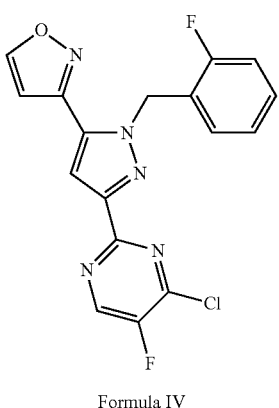

Formula IV

Intermediate (10') (214 g, 602 mmoles, 1.0 equiv.), acetonitrile (3000 mL) and N,N-dimethylaniline (109 g, 899 mmoles, 1.5 equiv.) were charged to a suitable reaction vessel equipped with a mechanical stirrer and a digital thermometer. The slurry mixture was heated to 70 to 80° C. Then phosphorous oxychloride (276 g, 1802 mmoles, 3.0 equiv.) was charged via an addition funnel over 30 min. while maintaining the reaction temperature 70-80° C. The mixture was stirred at 75 to 80° C. over 2 h and a green solution was obtained. The reaction was completed by HPLC. Then the mixture was cooled to 0 to 5° C. Water (1500 mL) was charged slowly via an addition funnel while maintaining the reaction temperature at 0 to 10° C. The slurry was stirred at 0 to 10° C. over 30 min. The resulting slurry was filtered, and the filter cake was washed with a pre-mixed solution of acetonitrile and water (500 mL/500 mL) and water (500 mL). The filter cake was dried under vacuum at 30 to 40° C. over 16 h to furnish intermediate of Formula IV as an off-white to pink solid (214 g, 95% yield, >99% pure by HPLC). $^1$H NMR (500 MHz, CDCl$_3$) δ ppm 8.65 (s, 1H); 8.48 (d, J=1.68 Hz, 1H); 7.44 (s, 1H); 7.21-7.25 (m, 1H); 6.97-7.06 (m, 2H); 6.83-6.87 (m, 1H); 6.61 (d, J=1.68 Hz, 1H); 6.03 (s, 2H).

a): Cyanation of Intermediate (15) to Provide 2-(bromomethyl)-3,3,3-trifluoro-2-((trimethylsilyl)oxy)propanenitrile (16)

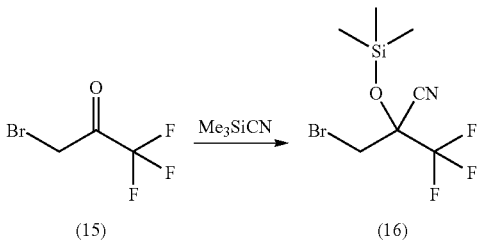

(15)     (16)

Trimethylsilanecarbonitrile (153 g, 1.54 moles, 0.97 equiv) and triethylamine (4.44 mL, 3.22 g, 0.032 mole, 0.02 equiv) were charged to a suitable reaction vessel equipped with a mechanical stirrer and a digital thermometer. The mixture was cooled to 5° C. 3-Bromo-1,1,1-trifluoropropan-2-one ((15), 304 g, 1.59 moles, 1.0 equiv) was charged via an addition funnel over 35 min, while maintaining the reaction temperature between 10 to 20° C. The mixture was stirred at 20 to 30° C. over 3 h after the addition to furnish intermediate (16) as a dense oil which was used directly in the next step. $^1$H-NMR (500 MHz, CDCl$_3$) δ ppm 3.68 (d, J=11.14 Hz, 1H); 3.57 (d, J=11.14 Hz, 1H), 0.34-0.37 (m, 9H).

b): Conversion of Nitrile Compound (16) to Amide to Provide 2-(bromomethyl)-3,3,3-trifluoro-2-hydroxypropanamide (17)

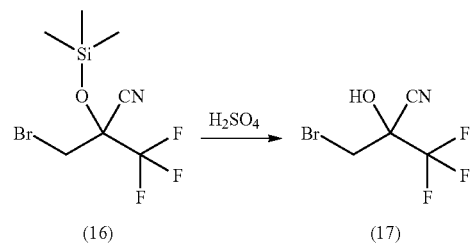

(16)     (17)

Concentrated sulfuric acid (339 mL, 6.37 moles, 4.0 equiv) was stirred in a suitable reaction vessel equipped with a mechanical stirrer, digital thermometer and an addition funnel. The sulfuric acid was heated to 45° C. The above intermediate (16) was added via an addition funnel over 50 min, while keeping the temperature below 75° C. The reaction mixture was stirred at 75° C. for 2 h and then allowed to cool to room temperature. ¹H-NMR indicated reaction complete. The reaction mixture was cooled to −15° C. and diluted with ethyl acetate (1824 mL) via an addition funnel over 45 min (very exothermic), while keeping the temperature between −15 to 5° C. Water (1520 mL) was added slowly via an addition funnel for 1 h 20 min. (very exothermic) between −10 to 0° C. The layers were separated and the organic layer was washed with 15% aqueous sodium chloride solution (1520 mL), 25% aqueous sodium carbonate solution (911 mL) followed by 15% aqueous sodium chloride solution (911 mL). The organic layer was filtered and concentrated under reduced pressure to get 348 g of intermediate (17) as light yellow oil. This oil was dissolved in methanol (1200 mL) and concentrated to furnish 380 g of intermediate (17). (296 g adjusted weight, 79% yield). ¹H-NMR (500 MHz, CDCl₃) δ 6.61-6.94 (m, 1H); 5.92-6.26 (m, 1H); 3.93-4.00 (m, 1H); 3.68 (d, J=11.14 Hz, 1H).

c): N-Alkylation of Compound (17) to Provide of 2-(aminomethyl)-3,3,3-trifluoro-2-hydroxypropanamide (14)

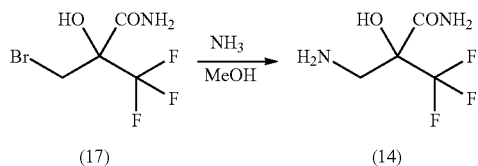

A 7 N solution of ammonia in methanol (600 mL, 4.28 moles, 10 equiv) was charged to a suitable reaction vessel equipped with a mechanical stirrer and a digital thermometer. The solution was cooled to 0 to 5° C. Then the intermediate (17) (102 g, 0.432 moles, 1 equiv) was added via an addition funnel over 30 min at 0 to 5° C. The reaction mixture was warmed to 20 to 25° C. over 1 h and held for 72 h. The reaction was completed by HPLC. The reaction mixture was cooled to 0 to 5° C. and sodium methoxide (78 mL, 5.4 M, 0.421 moles, 0.97 equiv) was added over 2 min. The reaction mixture was then concentrated under reduced pressure to a volume of 300 mL. 2 L of ethyl acetate was added and concentration was continued under reduced pressure to a volume to 700 mL to get a slurry. 700 mL of ethyl acetate was added to the slurry to make the final volume to 1400 mL. 102 mL of water was added and stirred for 2 min to get a biphasic solution. The layers were separated. The ethyl acetate layer was concentrated under reduced pressure to a volume of 600 mL. Then the ethyl acetate layer was heated to >60° C. and heptane (600 mL) was added slowly between 55 to 60° C. The mixture was cooled to 15 to 20° C. to give a slurry. The slurry was stirred at 15 to 20° C. for 2 h and filtered. The solids were dried under vacuum at 25° C. for 16 h to furnish amine (14) as white solid (48 g, 64% yield). ¹H-NMR (500 MHz, MeOH-d₄) δ ppm 2.94 (d, J=13.73 Hz, 1H); 3.24 (d, J=13.58 Hz, 1H).

d): Chiral Resolution of Amine (14) as the 1:1 Salt of (R)-2,2-dimethyl-5-(trifluoromethyl)oxazolidine-5-carboxamide (R)-2-hydroxysuccinate (18A) and (D)-malic acid

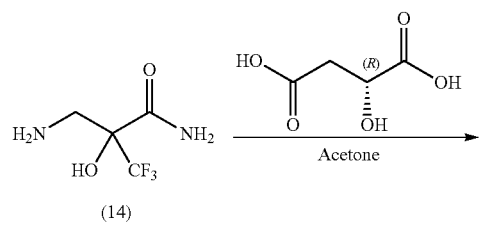

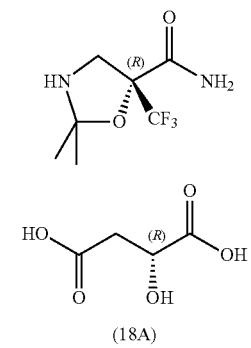

Amine (14) (105 g, 0.608 moles, 1.0 equiv.), (D)-Malic acid (82 g, 0.608 moles, 1.0 equiv.) and acetone (1571 mL) were charged to a suitable reaction vessel equipped with a mechanical stirrer and a digital thermometer. The reaction mixture was stirred at 20 to 25° C. for 16 h. The resulting slurry was filtered, and the wet cake was washed with acetone (300 mL). The wet cake was charged back to the reaction vessel, and acetone (625 mL) was charged. The slurry was heated to 53° C. and held for 6 h. The slurry was cooled to 20 to 25° C. and held at this temperature for 16 h. The slurry was filtered, and the wet cake was washed with acetone (200 mL). The wet cake was dried under vacuum at 40° C. for 4 h to furnish 82.4 g of the 1:1 salt of (18A) and (D)-malic acid as a white solid (82.4 g, 39% yield, 97% ee). ¹H-NMR (500 MHz, D₂O) δ ppm 4.33 (br, s, 1H); 3.61 (br, d, J=13.58 Hz, 1H); 3.40-3.47 (m, 1H); 2.76 (br, d, J=15.87 Hz, 1H); 2.53-2.63 (m, 1H); 2.16 (br, s, 4H).

e): Coupling of the 1:1 (D)-Malic Acid Salt of Intermediate (18A) and Formula IV to Provide (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Compound I)

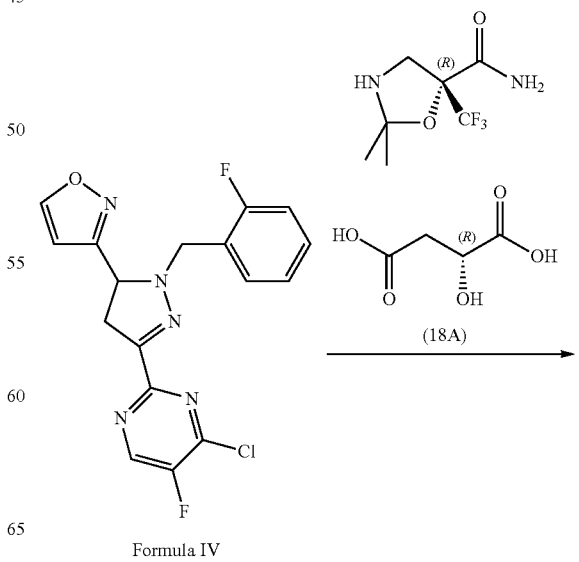

-continued

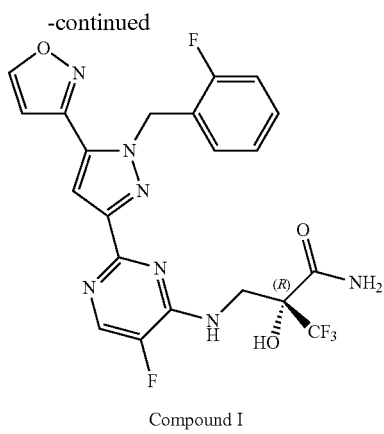

Compound I

The 1:1 salt of intermediate (18A) and (D)-malic acid (74.1 g, 0.214 moles, 2.5 equiv) and water (44.8 mL) were charged to a suitable reaction vessel equipped with a mechanical stirrer and a digital thermometer. The reaction mixture was heated to 70° C. and stirred for 20 min. Acetone generated during the reaction was removed by blowing with nitrogen. The reaction mixture was cooled to 30 to 40° C. and Formula IV (32 g, 0.086 moles, 1.0 equiv), DMSO (448 mL) and Hunig's base (44.7 mL, 0.257 moles, 3.0 equiv) were charged. The reaction mixture was heated to 90° C. and stirred at 90° C. over 17 h. The reaction was complete by HPLC. Then the mixture was cooled to 60° C. Another portion of Hunig's base (104 mL, 0.599 moles, 7.0 equiv) was charged followed by water (224 mL) at 55 to 62° C. The reaction mixture was stirred for 15 min at 55 to 60° C. to form the seed bed. Water (320 mL) was added via addition funnel at 55 to 62° C. over the course of 30 min, and the resultant slurry was stirred for 1 h at 55 to 60° C. The resulting slurry was filtered, and the filter cake was washed with a pre-mixed solution of methanol and water (320 mL/320 mL) followed by water (640 mL). The filter cake was then dried under vacuum at 40° C. over 16 h to furnish Compound I as an off-white solid (40 g, 92% yield, 99% pure by HPLC, 98% ee). $^1$H-NMR (500 MHz, DMSO-d$_6$) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Figure 12:
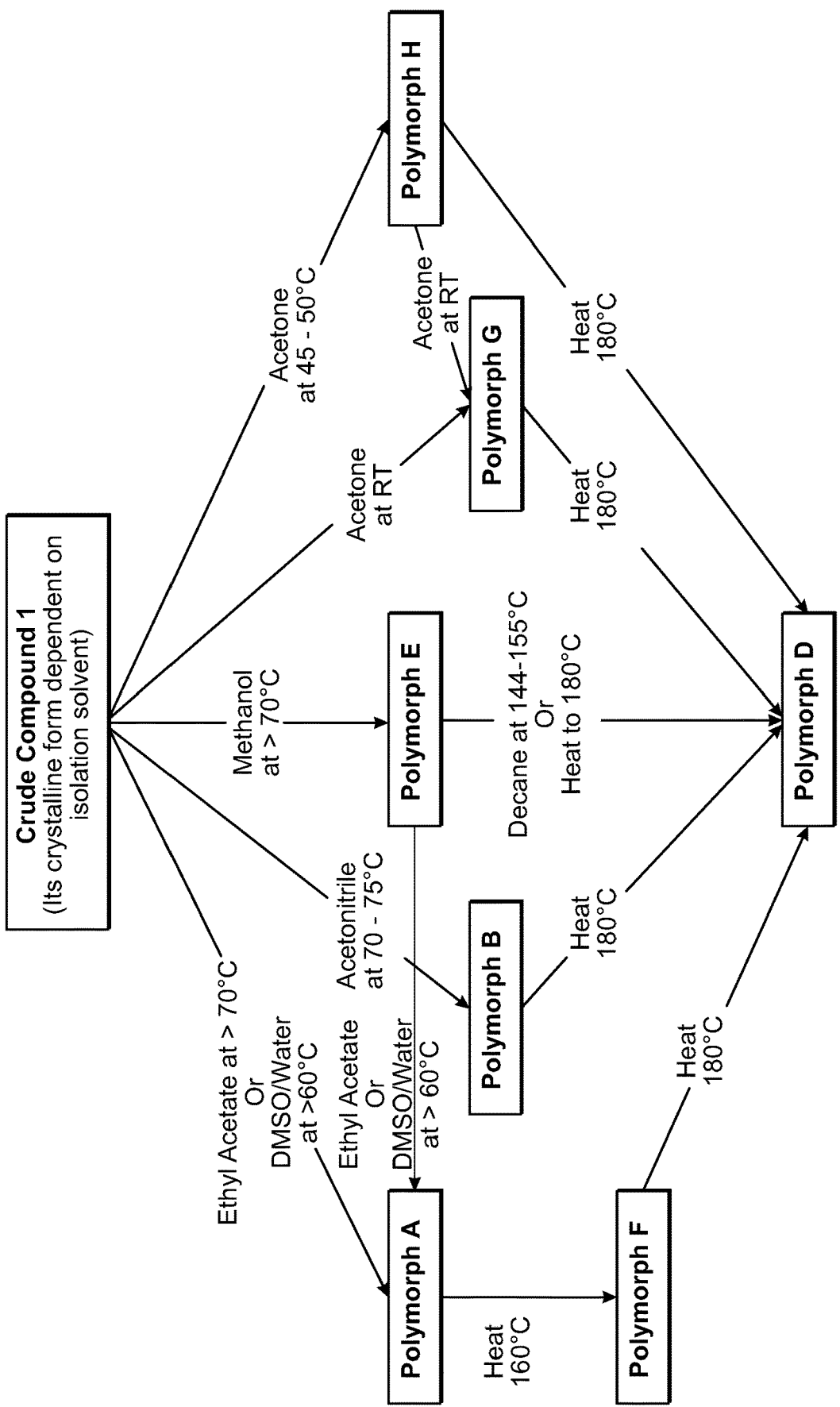
FIG. 12: Shows the relationships between crude Compound I, polymorphs Form A, Form B, Form D, Form E, Form F, Form G and Form H.

The interrelationship between crude Compound I, and its polymorphic forms Form A, Form B, Form D, Form E, Form F, Form G and Form H, are illustrated in FIG. 12.

Example 2: Recrystallization of Crude (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Crude Compound I) to Polymorph Form B Crude Compound I (0.68 kg, 1.33 mol) and acetonitrile (20.4 L) were charged to a 30 L jacketed reaction vessel. The reaction mixture was stirred at low speed and heated to 70 to 75° C. until most solids dissolved. The solution in 30 L jacketed reaction vessel was in-line filtered via gas dispersion tube (coarse frit) into a 100 L jacketed reaction vessel. The reaction mixture was then heated to 70-75° C. and water (20.4 L) was charged while maintaining batch temperature>65° C. over 1 h. The reaction mixture was cooled to 52-62° C. and stirred over a minimum of 1 h at 52 to 62° C. to form the seed bed. The resulting slurry was cooled to 0-5° C. over a minimum of 4 h and held at 0-5° C. over a minimum of 1 h. The slurry was filtered and the filter cake was washed with a pre-mixed solution of acetonitrile and water (3.4 L/3.4 L). The filter cake was then dried under vacuum at 90-100° C. over a minimum of 30 h to furnish Compound I as polymorph Form B as a white solid (0.58 kg, 85% yield). $^1$H-NMR (500 MHz, DMSO-d$_6$) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Example 3: Recrystallization of Crude (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Compound I) to Polymorph Form E To a 5 L 4 neck round-bottomed flask equipped with a mechanical stirrer, a condenser, a dropping funnel, a nitrogen inlet-outlet, a thermocouple and a heating-cooling capacity was charged crude Compound I (67.4 g, 132 mmol) and methanol (2500 mL). The mixture was heated to >60° C. (e.g., higher than 70° C.) to obtain a solution. The solution was filtered and the filtrate was heated to >60° C. Water (1500 mL) was added to the mixture while maintaining temperature>60° C. The mixture was allowed to cool to room temperature over 1 h and held at this temperature over 1 h. The slurry was filtered and the filter cake was rinsed with methanol/water (600 mL, 1/1 v/v). The filter cake was collected and dried under vacuum at 80° C. over 72 h to give compound I as polymorph Form E as a white solid (59.5 g, 88% yield).

Example 4A: Recrystallization of Polymorph form E of (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide to Polymorph Form A To a 1 L 4 neck round bottomed flask equipped with a mechanical stirrer, a condenser, a dropping funnel, a nitrogen inlet-outlet, a thermocouple and a heating-cooling capacity, was charged Compound I as polymorph Form E (19.3 g, 38 mmol) and ethyl acetate (600 mL). The mixture was heated to >70° C. to obtain a solution. The solution was filtered and the filtrate was stirred at 20 to 25° C. over 16 h to give a slurry. The slurry was concentrated under vacuum to a final volume of ~150 mL. Heptane (300 mL) was added to the slurry over 20 min and the mixture was concentrated under vacuum to a final volume of ~350 mL. The slurry was filtered and the filter cake was rinsed with heptane (50 mL). The filter cake was collected and dried under vacuum at 100° C. over 3 h to give polymorph Form A as a white solid (19.1 g, 99% yield).

Example 4B: Recrystallization of Crude (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Compound I) to Polymorph Form A Polymorph Form A was also obtained directly from crude Compound I by isolating from Ethyl acetate by a process analogous to that described in Example 4A, using crude Compound I instead of Form E as the starting material.

Polymorph Form A was also obtained directly from crude Compound I by isolating from DMSO/water after heating at higher than 60° C.

Polymorph Form A was also isolated when the crude Compound I was slurried in any of the solvents heptane, (isopropylacetate) IPAC, ethanol, ethyl acetate or decane at room temperature and allowed to stir for 14 to 30 hours. The samples were filtered and the residual solids analyzed by XRPD.

Example 5A: Recrystallization of Polymorph Form E of (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide to Polymorph Form D To a 2 L 4 neck round bottomed flask equipped with a mechanical stirrer, a condenser, a dropping funnel, a nitrogen inlet-outlet, a thermocouple and a heating-cooling capacity was charged Compound I as polymorph Form E (14.0 g, 28 mmol) and n-decane (560 mL). The mixture was heated to 145 to 155° C. and held at 145 to 155° C. for 45 min. The resulting slurry was cooled to 20 to 30° C. over 1 h and then filtered. The filter cake was rinsed with heptane (280 mL). The filter cake was collected and dried under vacuum at 80° C. over 72 h to give compound I as Form D as a white solid (12.9 g, 92% yield).

Example 5B: Other Methods of Obtaining Polymorph Form D

Polymorph form D was also obtained by heating many of the other polymorphic forms (neat) at 180° C. as summarized in FIG. 12 and described below. In some embodiments, Compound I was heated to obtain polymorph Form D. In some embodiments, polymorph Form F was heated to obtain polymorph Form D. In some embodiments, polymorph Form B was heated to obtain polymorph Form D. In some embodiments, polymorph Form E was heated to obtain polymorph Form D. In some embodiments, polymorph Form G was heated to obtain polymorph Form D. In some embodiments, polymorph Form H was heated to obtain polymorph Form D.

A 100 mL round bottom flask was charged Compound I, Form F, Form B, Form E, Form G or Form H (5 g). The solid was heated to 180° C. and held at 180° C. over 5 min. All Compound I solid slowly melted and resolidified to give a solid. The solid was grinded with mortar and pestle to give ~4.8 g of powder. HPLC showed 99.8% purity. XRPD showed it was Form D. DSC showed a sharp peak at 196° C.

Example 6: Preparation of Form F

A new polymorph Form F was obtained when Form A was heated neat at 160° C. This form appears to be unstable at rt and has not been isolated pure.

Example 7: Recrystallization of Crude (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Compound I) to Polymorph Form G To a flask equipped with a stirrer was charged crude Compound I (2.0 g) and acetone (15.0 mL). The mixture was stirred at room temperature (22 to 25° C.) for two hours. The resulting slurry was then filtered. The filter cake was rinsed with acetone (5 mL). The filter cake was collected and dried under vacuum at 40° C. for over 15 h to give polymorph Form G as a white solid.

Polymorph Form G was also obtained by stirring polymorph Form H obtained as described below in acetone at room temperature, followed by filtration and drying under vacuum at 30 to 40° C.

Example 8: Recrystallization of Crude (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide to Polymorph Form H To a flask equipped with a stirrer was charged crude Compound I (2.0 g) and acetone (15.0 mL). The mixture was heated to 45-50° C. and stirred until a solution is formed. The hot solution is then filtered and slowly cooled to room temperature while stirring. Stirred for an additional 15 hours and the resulting slurry was then filtered. The filter cake was rinsed with acetone (5 mL). The filter cake was collected and dried under vacuum at 40° C. over 15 h to give polymorph Form H as a white solid.

Example 9: Polymorph Characterization

X-Ray Powder Diffraction (XRPD):
X-Ray Powder Diffraction traces were obtained using a D8 Advance, Bruker apparatus; using one of two Methods:
Scan 5-45° 2-theta, 0.02° step size, 1 sec per step; or
Scan 3-40° 2-theta, 0.037° step size, 1.5 sec per step
Fourier Transform Infrared Spectroscopy (FTIR):
FTIR traces were obtained using a Nicolet iS 10 FTIR apparatus from ThermoFisher Scientific
Method: Analyzed by attenuated total reflectance with 32 scans and a resolution of 4 over a wavenumber range of 525-4000 $cm^{-1}$ with a background obtained before each measurement Example 10: HCl Salt Preparation Protocol 1:
50.5 mg of Compound I, as its polymorph Form D and 98.2 mL of 1M HCl were suspended in 2 mL of i-PrOH. The suspension was stirred with a temperature cycling between 20° C. and 40° C. A heating rate of 40° C./h and a cooling rate of 5° C./h were used. After 8 days the suspension was filtered and the solid was dried under vacuum (approximately 5 mbar, 1 h).
Protocol 2:
299.9 mg of Compound I as its polymorph Form D and a few crystals of the above obtained hydrochloric acid salt (from Protocol 1) were suspended in 5 mL of i-PrOH. 589 mL of 1 M HCl and 5 mL of i-PrOH were then added, and the suspension was stirred with a temperature cycling between 20° C. and 40° C. A heating rate of 40° C./h and a cooling rate of 5° C./h were used. After 6 days, the suspension was filtered and the solid was dried under vacuum (approximately 5 mbar, 1 h).

Example 11: HCl Salt Characterization

The HCl salt of Compound I is characterized by the XRPD pattern of FIG. 11.

The HCl salt of Compound I was characterized by elemental analysis, giving the measured and calculated values for a 1:1 ratio (Form D:HCl) displayed in the below table:

| Element | Measured values | Calculated values of FD:HCl = 1:1 |
|---|---|---|
| C | 45.8 wt-% | 46.2 wt-% |
| H | 3.3 wt-% | 3.1 wt-% |
| N | 18.0 wt-% | 18.0 wt-% |
| O | 8.8 wt-% | 8.8 wt-% |
| Cl | 6.3 wt-% | 6.5 wt-% |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:
1. A crystalline solid form of Compound I:

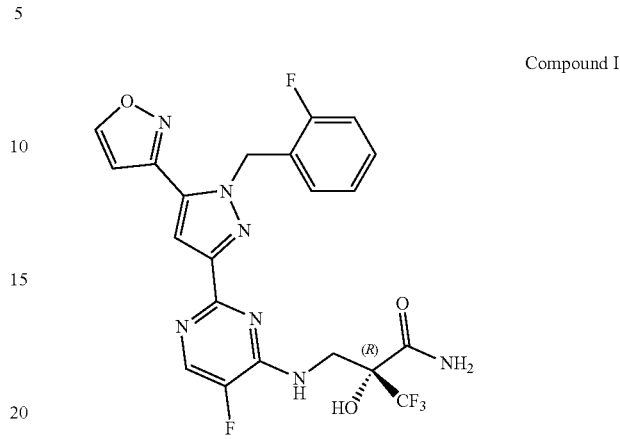

Compound I wherein:
(1) the crystalline solid form is crystalline free form Form E characterized by (i) peaks in the XRPD spectrum comprising: 7.4, 18.8-19.3, 21.1, 24.8 and 25.5 °2θ; (ii) peaks in the XRPD spectrum comprising: 7.4, 13.9, 15.1, 16.3, 17.6, 18.8-19.3, 21.1, 22.3-22.5, 24.8, 25.5 and 27.1 °2θ; (iii) an XRPD spectrum substantially similar to that shown in FIG. 2 or FIG. 6; (iv) a FT-Raman spectrum substantially similar to that shown in FIG. 10; (v) an IR spectrum that exhibits a peak maximum at 1690 cm$^{-1}$; (vi) an IR spectrum that exhibits a peak maximum at 1515 cm$^{-1}$; or (vii) an IR spectrum that exhibits band maxima at 1690 and 1515 cm$^{-1}$;
(2) the crystalline solid form is crystalline free form Form A characterized by (i) peaks in the XRPD spectrum comprising: 6.0, 18.3, 19.3, 20.2 and 22.0 °2θ; (ii) peaks in the XRPD spectrum comprising: 6.0, 8.5, 9.5, 12.4-12.9, 13.4, 17.1, 18.3, 19.3, 20.2, 22.0, 30.1 and 34.1 °2θ; (iii) peaks in the XRPD spectrum comprising: 6.0, 6.7, 8.5, 9.5, 10.9, 12.4-12.9, 13.4, 16.2, 17.1, 18.3, 19.3, 20.2, 22.0, 23.0, 24.1 to 24.8, 25.8, 30.1 and 34.1 °2θ; (iv) an XRPD spectrum substantially similar to that shown in FIG. 2 or in FIG. 3A; (v) peaks in the XRPD spectrum comprising: 6.1 (80.81% rel int), 9.6 (40.35%), 12.6 (41.26%), 13.6 (43.19%), 18.4 (53.57%), 19.4 (100.00%), 20.3 (57.01%) and 22.0 (56.64) °2θ; (vi) an XRPD spectrum substantially similar to that shown in FIG. 3C; (vii) a FT-Raman spectrum substantially similar to that shown in FIG. 10; or (viii) an IR spectrum that exhibits a band maximum at 1730 cm$^{-1}$;
(3) the crystalline solid form is crystalline free form Form D characterized by (i) peaks in the XRPD spectrum comprising: 17.1, 18.1, 18.8 and 25.0 °2θ; (ii) peaks in the XRPD spectrum comprising: 8.8, 17.1, 18.1, 18.8, and 25.0 °2θ; (iii) an XRPD spectrum substantially similar to that shown in FIG. 2 or FIG. 5A; (iv) peaks in the XRPD spectrum comprising: 4.7 (97.11% rel int), 8.3 (64.04%), 18.1 (80.97%), 18.6 (100.00%), and 26.8 (65.25) °2θ; (v) an XRPD spectrum substantially similar to that shown in FIG. 5C; (vi) a FT-Raman spectrum substantially similar to that shown in FIG. 10; (vii) an IR spectrum that exhibits a band maximum at 1665 cm$^{-1}$; (viii) an IR spectrum that exhibits a band maximum at 1639 cm$^{-1}$; (ix) an IR spectrum that exhibits a band maximum at 968 cm$^{-1}$; or (x) an IR spectrum that exhibits band maxima at 1665, 1639 and 968 cm$^{-1}$;
(4) the crystalline solid form is crystalline free form Form B characterized by (i) peaks in the XRPD spectrum comprising: 8.8, 16.4, 17.2, 18.8-19.1, 20.1, and 21.1-21.6°2θ; (ii) peaks in the XRPD spectrum comprising: 8.8, 10.6, 12.6-13.0, 14.6, 16.4, 17.2, 18.8-19.1, 20.1, 21.1-21.6, 24.5, 25.3, 27.0-27.5, 28.9, 29.8 and 30.5°2θ; (iii) an XRPD spectrum substantially similar to that shown in FIG. 2 or FIG. 4A; (iv) an XRPD spectrum substantially similar to that shown in FIG. 4C; (v) peaks in the XRPD spectrum comprising: 7.0 (44.44% rel int), 8.9 (76.55%), 17.4 (57.67%), 19.1 (100.00%), 20.3 (49.78%), 21.8 (36.16%), and 25.5 (52.26) °2θ; (vi) a FT-Raman spectrum substantially similar to that shown in FIG. 10; or (vii) an IR spectrum that exhibits a peak maximum at 1200 cm$^{-1}$;

(5) the crystalline solid form is crystalline free form Form F characterized by peaks in the XRPD spectrum comprising: 5.3 (100.00% rel int), 8.6 (58.80%), 16.4 (62.95%), and 19.0 (48.51%) °2θ; or an XRPD spectrum substantially similar to that shown in FIG. 7;

(6) the crystalline solid form is crystalline free form Form G characterized by peaks in the XRPD spectrum comprising: 10.7 (55.47% rel int), 13.9 (42.47%), 18.33 (100.00% %), and 21.6 (40.73%) °2θ; or an XRPD spectrum substantially similar to that shown in FIG. 8; or (7) the crystalline solid form is crystalline free form Form H characterized by (i) peaks in the XRPD spectrum comprising: 5.77 (89.22% rel int), 6.39 (100.00% %), 9.1 (84.17%), and 18.5 (67.04%) °2θ; (ii) characterized by peaks in the XRPD spectrum comprising: 5.77 (89.22% rel int), 6.39 (100.00% %), 9.1 (84.17%), 18.5 (67.04%), and 18.83 (67.04%) °2θ, or (iii) an XRPD spectrum substantially similar to that shown in FIG. 9.

2. The crystalline solid form of Compound I according to claim 1, wherein the crystalline solid form is crystalline free form Form E characterized by (i) peaks in the XRPD spectrum comprising: 7.4, 18.8-19.3, 21.1, 24.8 and 25.5 °2θ; (ii) peaks in the XRPD spectrum comprising: 7.4, 13.9, 15.1, 16.3, 17.6, 18.8-19.3, 21.1, 22.3-22.5, 24.8, 25.5 and 27.1°2θ; (iii) an XRPD spectrum substantially similar to that shown in FIG. 2 or FIG. 6; (iv) a FT-Raman spectrum substantially similar to that shown in FIG. 10; (v) an IR spectrum that exhibits a peak maximum at 1690 cm$^{-1}$; (vi) an IR spectrum that exhibits a peak maximum at 1515 cm$^{-1}$; or (vii) an IR spectrum that exhibits band maxima at 1690 and 1515 cm$^{-1}$.

3. The crystalline solid form of Compound I according to claim 1, wherein the crystalline solid form is crystalline free form Form A characterized by (i) peaks in the XRPD spectrum comprising: 6.0, 18.3, 19.3, 20.2 and 22.0 °2θ; (ii) peaks in the XRPD spectrum comprising: 6.0, 8.5, 9.5, 12.4-12.9, 13.4, 17.1, 18.3, 19.3, 20.2, 22.0, 30.1 and 34.1 °2θ; (iii) one or more peaks in the XRPD spectrum comprising: 6.0, 6.7, 8.5, 9.5, 10.9, 12.4-12.9, 13.4, 16.2, 17.1, 18.3, 19.3, 20.2, 22.0, 23.0, 24.1 to 24.8, 25.8, 30.1 and 34.1 °2θ; (iv) an XRPD spectrum substantially similar to that shown in FIG. 2 or in FIG. 3A; (v) peaks in the XRPD spectrum comprising: 6.1 (80.81% rel int), 9.6 (40.35%), 12.6 (41.26%), 13.6 (43.19%), 18.4 (53.57%), 19.4 (100.00%), 20.3 (57.01%) and 22.0 (56.64) °2θ; (vi) an XRPD spectrum substantially similar to that shown in FIG. 3C; (vii) a FT-Raman spectrum substantially similar to that shown in FIG. 10; or (viii) an IR spectrum that exhibits a band maximum at 1730 cm$^{-1}$.

4. The crystalline solid form of Compound I according to claim 1, wherein the crystalline solid form is crystalline free form Form D characterized by (i) peaks in the XRPD spectrum comprising: 17.1, 18.1, 18.8 and 25.0 °2θ; (ii) peaks in the XRPD spectrum comprising: 8.8, 17.1, 18.1, 18.8, and 25.0 °2θ; (iii) an XRPD spectrum substantially similar to that shown in FIG. 2 or FIG. 5A; (iv) peaks in the XRPD spectrum comprising: 4.7 (97.11% rel int), 8.3 (64.04%), 18.1 (80.97%), 18.6 (100.00%), and 26.8 (65.25) °2θ; (v) an XRPD spectrum substantially similar to that shown in FIG. 5C; (vi) a FT-Raman spectrum substantially similar to that shown in FIG. 10; (vii) an IR spectrum that exhibits a band maximum at 1665 cm$^{-1}$; (viii) an IR spectrum that exhibits a band maximum at 1639 cm$^{-1}$; (ix) an IR spectrum that exhibits a band maximum at 968 cm$^{-1}$; or (x) an IR spectrum that exhibits band maxima at 1665, 1639 and 968 cm$^{-1}$.

5. The crystalline solid form of Compound I according to claim 1, wherein the crystalline solid form is crystalline free form Form B characterized by (i) peaks in the XRPD spectrum comprising: 8.8, 16.4, 17.2, 18.8-19.1, 20.1, and 21.1-21.6 °2θ; (ii) peaks in the XRPD spectrum comprising: 8.8, 10.6, 12.6-13.0, 14.6, 16.4, 17.2, 18.8-19.1, 20.1, 21.1-21.6, 24.5, 25.3, 27.0-27.5, 28.9, 29.8 and 30.5 °2θ; (iii) an XRPD spectrum substantially similar to that shown in FIG. 2 or FIG. 4A; (iv) an XRPD spectrum substantially similar to that shown in FIG. 4C; (v) peaks in the XRPD spectrum comprising: 7.0 (44.44% rel int), 8.9 (76.55%), 17.4 (57.67%), 19.1 (100.00%), 20.3 (49.78%), 21.8 (36.16%), and 25.5 (52.26) °2θ; (vi) a FT-Raman spectrum substantially similar to that shown in FIG. 10; or (vii) an IR spectrum that exhibits a peak maximum at 1200 cm$^{-1}$.

6. The crystalline solid form of Compound I according to claim 1, wherein the crystalline solid form is crystalline free form Form F characterized by peaks in the XRPD spectrum comprising: 5.3 (100.00% rel int), 8.6 (58.80%), 16.4 (62.95%), and 19.0 (48.51%) °2θ; or an XRPD spectrum substantially similar to that shown in FIG. 7.

7. The crystalline solid form of Compound I according to claim 1, wherein the crystalline solid form is crystalline free form Form G characterized by peaks in the XRPD spectrum comprising: 10.7 (55.47% rel int), 13.9 (42.47%), 18.33 (100.00% %), and 21.6 (40.73%) °2θ; or an XRPD spectrum substantially similar to that shown in FIG. 8.

8. The crystalline solid form of Compound I according to claim 1, wherein the crystalline solid form is crystalline free form Form H characterized by (i) peaks in the XRPD spectrum comprising: 5.77 (89.22% rel int), 6.39 (100.00% %), 9.1 (84.17%), and 18.5 (67.04%) °2θ; (ii) characterized by peaks in the XRPD spectrum comprising: 5.77 (89.22% rel int), 6.39 (100.00% %), 9.1 (84.17%), 18.5 (67.04%), and 18.83 (67.04%) °2θ; or (iii) an XRPD spectrum substantially similar to that shown in FIG. 9.

9. A process for preparing crystalline free form Form E of Compound I according to claim 2, comprising:
  a. dissolving crude Compound I in MeOH at a minimum of 60° C. to obtain a solution;
  b. filtering said solution and heating the filtrate at a minimum of 60° C.;
  c. adding water to said filtrate to form an aqueous solution and cooling said aqueous solution to room temperature (rt);
  d. filtering said aqueous solution and drying the filtrate under vacuum.

10. A process for preparing crystalline free form Form A of Compound I according to claim 3, comprising:
  (i) the steps of:
    a. dissolving crystalline free form Form E in ethyl acetate at a minimum of 70° C. to obtain a solution;
    b. filtering said solution and stirring the resulting filtrate at 20 to 25° C. over 16 hours to form a slurry;
    c. concentrating and filtering, and drying said slurry under vacuum; or (ii) the steps of:
  a. dissolving crude Compound I in ethyl acetate at a minimum of 70° C. to obtain a solution;
  b. filtering said solution and stirring the resulting filtrate at 20 to 25° C. over 16 hours to form a slurry;
  c. concentrating and filtering, and drying said slurry under vacuum; or
(iii) the steps of:
  a. heating crude Compound I in DMSO at a minimum of 60° C. to form a solution;
  b. adding water to form a slurry and
  c. filtering said slurry to isolate crystalline free form Form A; or
(iv) the steps of:
  a. slurrying crude Compound I in a solvent selected from heptane, IPAC, ethanol, ethyl acetate, or decane or a mixture thereof;
  b. stirring for 14 to 30 hours at rt; and
  c. filtering to said slurry and drying under vacuum.

11. A process for preparing crystalline free form Form D of Compound I according to claim 4, comprising
(i) the steps of:
  a. mixing crystalline free form Form E with n-decane at 145-155° C. to obtain a slurry;
  b. cooling the slurry to 20 to 30° C. over 1 hour; and
  c. filtering said slurry and drying under vacuum; or
(ii) heating any one of crystalline free forms Form F, Form B, Form E, Form G, or Form H, or mixtures thereof, neat at 180° C.

12. A process for preparing crystalline free form Form B of Compound I according to claim 5, comprising:
  a. mixing crude Compound I with acetonitrile to form a solution;
  b. filtering said solution to form a filtrate and heating said filtrate at 70 to 75° C.;
  c. adding water to said heated filtrate;
  d. cooling to 52-62° C. to form a slurry;
  e. further cooling said slurry to 0-5° C. for at least 4 hours; and
  f. filtering the cooled slurry and drying the resulting filtrate under vacuum.

13. A process for preparing crystalline free form Form F of Compound I according to claim 6, comprising heating Form A neat at 160° C.

14. A process for preparing crystalline free form Form G of Compound I according to claim 7, comprising
(i) the steps of:
  a. mixing crude Compound I in acetone at room temperature for about 2 hours to form a slurry; and
  b. filtering said slurry and drying under vacuum; or
(ii) the steps of:
  a. stirring Form H in acetone at room temperature for about 2 hours to form a slurry; and
  b. filtering said slurry and drying under vacuum.

15. A process for preparing crystalline free form Form H of Compound I according to claim 8, comprising:
  a. mixing crude Compound I with acetone at 45-50° C. to obtain a solution;
  b. filtering and cooling to form a slurry; and
  c. stirring and filtering said slurry and drying under vacuum.

16. A pharmaceutical composition comprising a crystalline solid form of Compound I according to claim 1, and at least one pharmaceutically acceptable excipient or carrier.

17. A method of treating sickle cell disease in a subject in need of treatment, comprising administering a therapeutically effective amount of the crystalline solid form of Compound I of claim 1 to the subject in need of treatment.

18. The crystalline solid form of Compound I according to claim 2, wherein the crystalline solid form is crystalline free form Form E characterized by peaks in the XRPD spectrum comprising: 7.4, 18.8-19.3, 21.1, 24.8 and 25.5°2θ.

19. The crystalline solid form of Compound I according to claim 3, wherein the crystalline solid form is crystalline free form Form A characterized by peaks in the XRPD spectrum comprising: 6.0, 18.3, 19.3, 20.2 and 22.0°2θ.

20. The crystalline solid form of Compound I according to claim 4, wherein the crystalline solid form is crystalline free form Form D characterized by peaks in the XRPD spectrum comprising: 17.1, 18.1, 18.8 and 25°2θ.

21. The crystalline solid form of Compound I according to claim 5, wherein the crystalline solid form is crystalline free form Form B characterized by peaks in the XRPD spectrum comprising: 8.8, 16.4, 17.2, 18.8-19.1, 20.1, and 21.1-21.6° 2θ.

22. The crystalline solid form of Compound I according to claim 6, wherein the crystalline solid form is crystalline free form Form F characterized by peaks in the XRPD spectrum comprising: 5.3(100.00% rel int), 8.6(58.80%), 16.4(62.95%), and 19.0(48.51%) °2θ.

23. The crystalline solid form of Compound I according to claim 7, wherein the crystalline solid form is crystalline free form Form G characterized by peaks in the XRPD spectrum comprising: 10.7(55.47% rel int), 13.9(42.47%), 18.33(100.00% %), and 21.6(40.73%) ° 2θ.

24. The crystalline solid form of Compound I according to claim 8, wherein the crystalline solid form is crystalline free form Form H characterized by peaks in the XRPD spectrum comprising: 5.77(89.22% rel int), 6.39(100.00% %), 9.1(84.17%), and 18.5(67.04%) ° 2θ.

* * * * *

UNITED STATES PATENT AND TRADEMARK OFFICE
CERTIFICATE OF CORRECTION

PATENT NO. : 10,889,577 B2
APPLICATION NO. : 16/315226
DATED : January 12, 2021
INVENTOR(S) : Vasu Sethuraman et al.

Page 1 of 1

It is certified that error appears in the above-identified patent and that said Letters Patent is hereby corrected as shown below:

In the Claims

Column 68, Claim 1, Line 46, delete "56.64" and replace with -- 56.64% --.

Column 68, Claim 1, Line 58, delete "65.25" and replace with -- 65.25% --.

Column 69, Claim 1, Line 10, delete "52.26" and replace with -- 52.26% --.

Column 69, Claim 1, Line 20, 25 and 28, delete "100.00% %" and replace with -- 100.00% --.

Column 69, Claim 3, Line 50, delete "one or more".

Column 70, Claim 7, Line 37, delete "100.00% %" and replace with -- 100.00% --.

Column 70, Claim 8, Line 45, delete "100.00% %" and replace with -- 100.00% --.

Column 72, Claim 23, Line 45, delete "100.00% %" and replace with -- 100.00% --.

Column 72, Claim 24, Line 49, delete "100.00% %" and replace with -- 100.00% --.

Signed and Sealed this
Fourth Day of January, 2022

Drew Hirshfeld
*Performing the Functions and Duties of the
Under Secretary of Commerce for Intellectual Property and
Director of the United States Patent and Trademark Office*